United States Patent [19]

Li et al.

[11] Patent Number: 4,552,898

[45] Date of Patent: * Nov. 12, 1985

[54] [3.2.0]BICYCLOHEPTANONE OXIME ETHERS WITH VALUABLE THERAPEUTIC PROPERTIES

[75] Inventors: Tsung-Tee Li, Los Altos Hills; Michael Marx, Mountain View, both of Calif.

[73] Assignee: Syntex (U.S.A.) Inc., Palo Alto, Calif.

[*] Notice: The portion of the term of this patent subsequent to Dec. 27, 2000 has been disclaimed.

[21] Appl. No.: 524,711

[22] Filed: Aug. 19, 1983

Related U.S. Application Data

[63] Continuation-in-part of Ser. No. 397,951, Jul. 14, 1982, Pat. No. 4,423,068.

[51] Int. Cl.$^4$ .................. A61K 31/19; A61K 31/215; C07C 131/02
[52] U.S. Cl. ..................... 514/561; 514/510; 514/567; 560/35; 560/116; 560/119; 562/440; 562/498; 562/501
[58] Field of Search ................... 560/35, 119, 116; 562/435, 440, 501, 498; 424/305, 308, 317, 319, 309; 514/510, 561, 567

[56] References Cited

U.S. PATENT DOCUMENTS

| | | | |
|---|---|---|---|
| 4,235,930 | 11/1980 | Skuballa et al. | 424/305 |
| 4,250,183 | 2/1981 | Krastinat | 424/305 |
| 4,254,278 | 3/1981 | Floyd, Jr. | 424/305 |
| 4,258,057 | 3/1981 | Bartmann et al. | 424/305 |
| 4,272,512 | 6/1981 | Gaffar | 424/305 |
| 4,322,435 | 3/1982 | Kojima et al. | 562/501 |
| 4,423,068 | 12/1983 | Li et al. | 562/501 |

OTHER PUBLICATIONS

*The Merck Index*, 9th Ed., Merck and Co., Inc., Rahway, N.J., 1976, pp. 1292-1293.

*Primary Examiner*—Michael L. Shippen
*Assistant Examiner*—Patricia M. Scott
*Attorney, Agent, or Firm*—Grant D. Green; Tom M. Moran; Alan M. Krubiner

[57] ABSTRACT

Compounds useful in treating cardiovascular disorders are the carboxylic acids depicted in formulas (1) and (2)

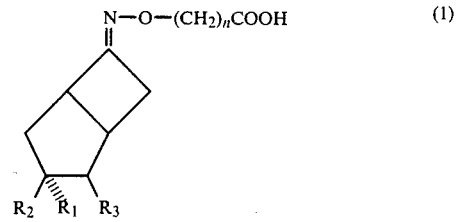

(1)

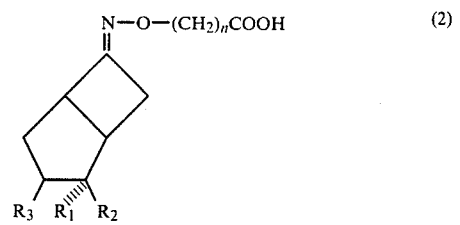

(2)

as well as their pharmaceutically acceptable, non-toxic salts and esters, wherein:
  n is an integer from one to four;
  $R_1$ is hydroxy;
  $R_2$ is hydrogen; or
  $R_1$ and $R_2$ together are an oxo group;
  $R_3$ is

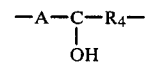

wherein
  A is —$CH_2$—$CH_2$—; trans—CH═CH—; —C≡C—; and
  $R_4$ is linear or branched alkyl of one to twelve carbons, preferably 1-10 carbons, most preferably 3-8 carbons, cycloalkyl of three to eight carbons; phenyl optionally substituted with one or two identical substituents selected from the group consisting of lower alkyl, lower alkoxy, hydroxy, trifluoromethyl, and halo; or phenyl-loweralkyl optionally substituted with one or two identical substituents selected from the group consisting of lower alkyl, lower alkoxy, hydroxy, trifluoromethyl, and halo.

49 Claims, No Drawings

[3.2.0]BICYCLOHEPTANONE OXIME ETHERS WITH VALUABLE THERAPEUTIC PROPERTIES

This application is a continuation-in-part of Ser. No. 397,951, filed July 14, 1982, now U.S. Pat. No. 4,423,068.

BACKGROUND OF THE INVENTION

1. Field of the Invention

This invention concerns novel oxime ether derivatives of certain bicyclo[3.2.0.]heptan-6-ones and pharmaceutically acceptable salts and esters thereof, their use in treating cardiovascular disorders, pharmaceutical compositions containing these compounds, and methods of preparing such compounds.

2. Related Disclosures

Bicyclo[3.2.0]hept-2-en-6-one is readily prepared from cyclopentadiene. (*J. Org. Chem.*, 37: 2363, 1972). This and related cycloheptanones are key intermediates in various prostaglandin syntheses. Bindra and Bindra, *Prostaglandin Synthesis*, Acad. Press, N.Y. (1977). They are also known to be used in the manufacture of fragrant compounds (Belgium Pat. No. BE-862-775 to Allen and Hanburys, Ltd.; and Russian Pat. No. SU-639-854 to Zelinskii of Org. Chem. Institute, USSR).

Synthetic prostaglandin analogues with a bicyclo [2.2.1]heptane skeleton which incorporate an oxime ether moiety in the ω-side chain are described in U.S. Pat. No. 3,872,169 to Bellina of E.I. du Pont de Nemours.

Oxyimino-substituted (1R,cis)-cyclopropanecarboxylate and oxyimino-substituted (1R,trans)-cyclopropanecarboxylates are useful as pesticides (U.S. Pat. Nos. 4,211,789 and 4,211,792 to Roman et al of Shell Oil Company, and 4,219,563 to Powel of Shell Oil Company).

Compounds structurally related to those of the present invention are bicyclo[2.2.1]heptanes or heptanones which are substituted at the 5-position by a 6-carboxyhex-2-enyl group and at the 6-position by an aldoxime or ketoxime group which is O-substituted by an aliphatic or aromatic hydrocarbon residue or aliphatic hydrocarbon residue substituted directly or through an oxygen or sulfur atom by an aromatic residue. (PCT International Application No. PCT/GB80/00001, PCT International Publication No. WO 80/01381).

SUMMARY OF THE PRESENT INVENTION

One aspect of the present invention relates to compounds of the formula (1) and (2)

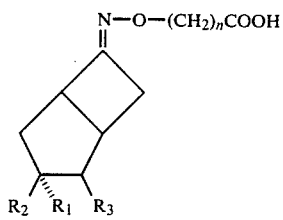
(1)

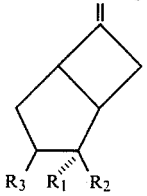
(2)

and their pharmaceutically acceptable, non-toxic salts or esters wherein:

n is an integer from one to four;
$R_1$ is hydroxy;
$R_2$ is hydrogen; or
$R_1$ and $R_2$ together are an oxo group;
$R_3$ is

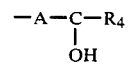

wherein
A is $-CH_2-CH_2-$, trans$-CH=CH-$, or $-C\equiv C-$; and
$R_4$ is linear or branched alkyl of one to twelve carbons, preferably 1–10 carbons, most preferably 3–8 carbons, cycloalkyl of three to eight carbons, phenyl optionally substituted with one or two identical substituents selected from the group consisting of lower alkyl, lower alkoxy, hydroxy, trifluoromethyl, halo, or phenyllower-alkyl optionally substituted with one or two identical substituents selected from the group consisting of lower alkyl, lower alkoxy, hydroxy, trifluoromethyl, and halo.

Another aspect of this invention is a method of treating cardiovascular disorders in a mammal by administering a therapeutically effective amount of a compound of formula (1) or (2) or their pharmaceutically acceptable salts or esters as defined above.

Still another aspect of the invention is a pharmaceutical composition containing a suitable pharmaceutical excipient and a compound of formula (1) or (2) or its pharmaceutically acceptable salts and esters.

Lastly, another aspect of the invention is a process for preparing compounds of formulas (1) and (2), and their corresponding pharmaceutically acceptable, non-toxic salts and esters, as discussed below.

DETAILED DESCRIPTION OF THE INVENTION

Definitions

As used herein the pharmaceutically acceptable, non-toxic salt derivatives of the compounds of formula (1) and formula (2) are carboxylic acid salts obtained by reaction of the COOH moiety in formula (1) or (2) with a suitable amine or inorganic base. Specific preparations are discussed hereinafter.

The pharmaceutically acceptable carboxylic esters corresponding to the acids of formula (1) or (2) are prepared by conventional methods from the acid, e.g. by reaction with the appropriate diazoalkane, or an activated derivative optionally employing a condensing agent such as dicyclohexyl carbodiimide, by reaction of a salt with an appropriate active alkylating agent, or by ester exchange from an existing ester. Specific preparations are described in the procedures and examples below.

"Oxo group" as used herein means an oxygen attached to a carbon atom by a double bond.

The term "alkyl" refers to and includes saturated branched and straight chain hydrocarbon radicals containing the number of carbons indicated. Typical alkyl groups include methyl, ethyl, propyl, isopropyl, butyl, tertiary butyl, neopentyl, isopentyl, hexyl, octyl, nonyl, isodecyl, 6-methyldecyl.

"Cycloalkyl" as used herein means a saturated monocyclic hydrocarbon radical containing 3-8 carbon atoms, such as cyclopropyl, cyclobutyl, cyclopentyl, cyclohexyl, cycloheptyl and cyclooctyl.

The term, "lower alkyl" refers to a branched or unbranched saturated hydrocarbon chain of 1-4 carbons, such as, for example, methyl, ethyl, n-propyl, i-butyl and the like.

The term "alkoxy" refers to the radical -O-alkyl wherein "alkyl" is as defined above. This includes radicals such as methoxy, ethoxy, 2-propoxy, butoxy, 3-pentoxy and the like.

"Lower alkoxy" means the group -OR wherein R is lower alkyl as herein defined.

"Halo" as used herein denotes fluorine, chlorine, bromine, or iodine.

"Substituted phenyl" as used herein encompasses all possible isomeric phenyl radicals mono- or disubstituted with a substituent selected from the group consisting of lower alkyl, lower alkoxy, hydroxy, trifluoromethyl and halo, with the proviso that in the disubstituted case both substituents must be the same.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution.

"Inhibitor" as used herein means a chemical entity which has the capability to restrain, stop or retard a physiologic, chemical or enzymatic action. To be an effective inhibitor, the chemical entity must be effective in low concentration. The effectiveness of the inhibitor is determined by establishing the minimum concentration required to produce a specified degree of inhibition of the target chemical or other reaction. The lower the effective concentration, the stronger the inhibitor.

"Inhibitors of platelet aggregation" as used herein are chemical entities which are effective in preventing a normally caused (by bleeding or damage of endothelium of a blood vessel) or artificially caused (by appropriate inducer) platelet aggregation. Inhibitory effect of the claimed compounds is expressed as inhibitory concentration IC$_{50}$ and as the potency of an inhibitor.

"Inhibitory concentration (IC$_{50}$)" as used herein is the concentration of the inhibitor which is necessary to effect a 50% reduction of the aggregatory response to a standard dose of a stimulant of platelet aggregation inducer.

"Potency of inhibitor" as used herein is expressed relative to the potent natural inhibitor PGE$_1$. Thus for a test compound A, $$\text{Potency}_A = \frac{(IC_{50})PGE_1}{(IC_{50})_A}$$

The designation "ω" as used hereinafter to denote the position of a substituent in a straight chain carboxylic acid, identifies the most remote atom, i.e. the terminus of the chain. Thus ω-aminocaproic acid = 6-aminocaproic acid, while ω-bromo dodecanoic acid = 12-bromododecanoic acid.

The numbering system for the bicyclo [3.2.0] heptane system is shown in the scheme illustration and is used in naming the intermediates and product compounds of the invention.

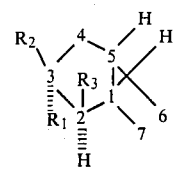

The prefixes exo- and endo- are used in their conventional fashion to denote the stereochemistry (cis- and trans-, respectively) of substituents with reference to the ring junction hydrogens (H-1, H-5). When a particular stereochemistry is implied in the structural drawings, exo- bonds are shown by solid lines, while broken lines indicate endo-substituents. Thus in the scheme illustration above, R$^1$ = 3-endo
R$^2$ = 3-exo
R$^3$ = 2-exo and the stereochemical designations α and β are applied to a hydroxyl substituent in R$_3$ and these terms designate a broken line bond and a solid line bond to the hydroxyl respectively. Classical nomenclature is used to name a compound having a triple bond as alkynyl; a double bond as alkenyl; a single bond as alkyl; and two bonds emanating from the same atom as -ylidene. Exemplary names are given in the "Preferred Embodiments" section of this application.

PREFERRED EMBODIMENTS OF THE INVENTION

One subclass of compounds of the invention is represented by formula (1) wherein n is 1, 2, or 3.

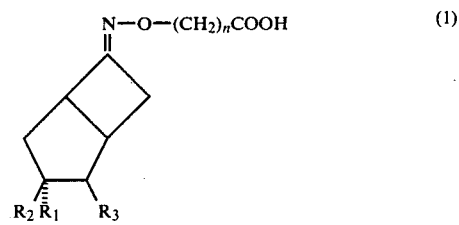

One preferred subgroup includes the compounds of formula (1) wherein n is 3 or 1; R$_1$ is hydroxy; R$_2$ is hydrogen, R$_3$ is

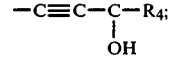

$R_4$ is alkyl of 1 to 12 carbons, preferably 1–10 carbons, most preferably 3–8 carbons; and the pharmaceutically acceptable, non-toxic salts and esters thereof. Compounds representative of this subgroup are N-[3-endo-hydroxy-2-exo-(3-hydroxy-alk-1-ynyl)bicyclo[3.2.0]hept-6-ylidene]-4-aminooxybutyric acid and N-[3-endo-hydroxy-2-exo-(3-hydroxy-alk-1-ynyl)bicyclo[3.2.0]hept-6-ylidene]-aminooxyacetic acid.

A more preferred subclass of compounds are those represented by formula (2) wherein n is 1, 2 or 3.

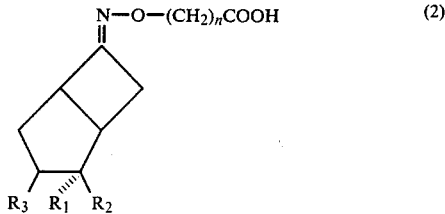

and a most particularly preferred subgroup of compounds are those represented by formula (2) wherein n is 1 or 2; $R_1$ is hydroxy; $R_2$ is hydrogen; $R_3$ is

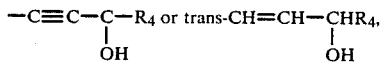

with those compounds wherein $R_4$ is alkyl of 1–10 carbons, in particular, alkyl of 3–8 carbons such as n-pentyl, cyclopentyl or cyclohexyl being of the highest preference, and their pharmaceutically acceptable, non-toxic salts and esters. This class encompasses but is not limited to the following compounds:

N-[2-endo-hydroxy-3-exo-(3-hydroxy-but-1-ynyl)bicyclo[3.2.0]hept-6-ylidene]-3-aminooxypropionic acid;

N-[2-endo-hydroxy-3-exo-(3-hydroxy-pent-1-ynyl)-bicyclo[3.2.0]hept-6-ylidene]-3-aminooxypropionic acid;

N-[2-endo-hydroxy-3-exo-(3-hydroxy-hex-1-ynyl)bicyclo[3.2.0]hept-6-ylidene]-3-aminooxypropionic acid;

N-[2-endo-hydroxy-3-exo-(3-hydroxy-hept-1-ynyl)-bicyclo[3.2.0]hept-6-ylidene]-3-aminooxypropionic acid;

N-[2-endo-hydroxy-3-exo-(3-hydroxy-oct-1-ynyl)bicyclo[3.2.0]hept-6-ylidene]-3-aminooxypropionic acid;

N-[2-endo-hydroxy-3-exo-(3-hydroxy-non-1-ynyl)bicyclo[3.2.0]hept-6-ylidene]-3-aminooxypropionic acid;

N-[2-endo-hydroxy-3-exo-(3-hydroxy-dec-1-ynyl)bicyclo[3.2.0]hept-6-ylidene]-3-aminooxypropionic acid;

N-[2-endo-hydroxy-3-exo-(3-hydroxy-undec-1-ynyl)-bicyclo[3.2.0]hept-6-ylidene]-3-aminooxypropionic acid;

N-[2-endo-hydroxy-3-exo-(3-hydroxy-dodec-1-ynyl)-bicyclo[3.2.0]hept-6-ylidene]-3-aminooxypropionic acid;

N-[2-endo-hydroxy-3-exo-(3-hydroxy-3-cyclopentyl-prop-1-ynyl)-bicyclo[3.2.0]hept-6-ylidene]-3-aminooxypropionic acid;

N-[2-endo-hydroxy-3-exo-(3-hydroxy-3-cyclohexyl-prop-0-ynyl)-bicyclo[3.2.0]hept-6-ylidene]-3-aminooxypropionic acid;

N-[2-endo-hydroxy-3-exo-(3-hydroxy-3-phenylprop-1ynyl)bicyclo[3.2.0]hept-6-ylidene]-3-aminooxypropionic acid; and N-[2-endo-hydroxy-3-exo-(3-hydroxy-3-(2-trifluoromethyl)phenylprop-1-ynyl)bicyclo[3.2.0]hept-6-ylidene]-3-aminooxypropionic acid.

N-[2-endo-hydroxy-3-exo-(3-hydroxy-but-1-ynyl)bicyclo[3.2.0]hept-6-ylidene]aminooxyacetic acid;

N-[2-endo-hydroxy-3-exo-(3-hydroxy-pent-1-ynyl)-bicyclo[3.2.0]hept-6-ylidene]aminooxyacetic acid;

N-[2-endo-hydroxy-3-exo-(3-hydroxy-hex-1-ynyl)bicyclo[3.2.0]hept-6-ylidene]aminooxyacetic acid;

N-[2-endo-hydroxy-3-exo-(3-hydroxy-hept-1-ynyl)-bicyclo[3.2.0]hept-6-ylidene]aminooxyacetic acid;

N-[2-endo-hydroxy-3-exo-(3-hydroxy-oct-1-ynyl)bicyclo[3.2.0]hept-6-ylidene]aminooxyacetic acid;

N-[2-endo-hydroxy-3-exo-(3-hydroxy-non-1-ynyl)bicyclo[3.2.0]hept-6-ylidene]aminooxyacetic acid;

N-[2-endo-hydroxy-3-exo-(3-hydroxy-dec-1-ynyl)bicyclo[3.2.0]hept-6-ylidene]aminooxyacetic acid;

N-[2-endo-hydroxy-3-exo-(3-hydroxy-undec-1-ynyl)-bicyclo[3.2.0]hept-6-ylidene]aminooxyacetic acid;

N-[2-endo-hydroxy-3-exo-(3-hydroxy-dodec-1-ynyl)-bicyclo[3.2.0]hept-6-ylidene]aminooxyacetic acid;

N-[2-endo-hydroxy-3-exo-(3-hydroxy-3-cyclopentyl-prop-1-ynyl)-bicyclo[3.2.0]hept-6-ylidene]aminooxyacetic acid;

N-[2-endo-hydroxy-3-exo-(3-hydroxy-3-cyclohexyl-prop-1-ynyl)-bicyclo[3.2.0]hept-6-ylidene]aminooxyacetic acid;

N-[2-endo-hydroxy-3-exo-(3-hydroxy-3-phenylprop-1-ynyl)bicyclo[3.2.0]hept-6-ylidene]aminooxyacetic acid; and N-[2-endo-hydroxy-3-exo-(3-hydroxy-3-(2-trifluoromethyl)phenylprop-1-ynyl)bicyclo[3.2.0]hept-6-ylidene]-aminooxyacetic acid.

N-[2-endo-hydroxy-3-exo-(3-hydroxy-but-1-transenyl)bicyclo[3.2.0]hept-6-ylidene]-3-aminooxypropionic acid;

N-[2-endo-hydroxy-3-exo-(3-hydroxy-pent-1-transenyl)bicyclo[3.2.0]hept-6-ylidene]-3-aminooxypropionic acid;

N-[2-endo-hydroxy-3-exo-(3-hydroxy-hex-1-transenyl)bicyclo[3.2.0]hept-6-ylidene]-3-aminooxypropionic acid;

N-[2-endo-hydroxy-3-exo-(3-hydroxy-hept-1-transenyl)bicyclo[3.2.0]hept-6-ylidene]-3-aminooxypropionic acid;

N-[2-endo-hydroxy-3-exo-(3-hydroxy-oct-1-transenyl)bicyclo[3.2.0]hept-6-ylidene]-3-aminooxypropionic acid;

N-[2-endo-hydroxy-3-exo-(3-hydroxy-non-1-transenyl)bicyclo[3.2.0]hept-6-ylidene]-3-aminooxypropionic acid;

N-[2-endo-hydroxy-3-exo-(3-hydroxy-dec-1-transenyl)bicyclo[3.2.0]hept-6-ylidene]-3-aminooxypropionic acid;

N-[2-endo-hydroxy-3-exo-(3-hydroxy-undec-1-transenyl)bicyclo[3.2.0]hept-6-ylidene]-3-aminooxypropionic N-[2-endo-hydroxy-3-exo-(3-hydroxy-dodec-1-transenyl)-bicyclo[3.2.0]hept-6-ylidene]-3-aminooxypropionic N-[2-endo-hydroxy-3-exo-(3-hydroxy-3-cyclopentyl-prop-1-trans-enyl)-bicyclo[3.2.0]hept-6-ylidene]-3-aminooxypropionic acid;

N-[2-endo-hydroxy-3-exo-(3-hydroxy-3-cyclohexyl-prop-1-trans-enyl)-bicyclo[3.2.0]hept-6-ylidene]-3-aminooxypropionic acid;

N-[2-endo-hydroxy-3-exo-(3-hydroxy-3-phenylprop-1-trans-enyl)bicyclo[3.2.0]hept-6-ylidene]-3-aminooxypropionic acid; and N-[2-endo-hydroxy-3-exo-(3-hydroxy-3-(2-trifluoromethyl)phenylprop-1-trans-enyl)bicyclo[3.2.0]hept-6ylidene]-3-aminooxypropionic acid.

N-[2-endo-hydroxy-3-exo-(3-hydroxy-but-1-trans-enyl)bicyclo[3.2.0]hept-6-ylidene]aminooxyacetic acid;

N-[2-endo-hydroxy-3-exo-(3-hydroxy-pent-1-trans-enyl)bicyclo[3.2.0]hept-6-ylidene]aminooxyacetic acid;

N-[2-endo-hydroxy-3-exo-(3-hydroxy-hex-1-trans-enyl)bicyclo[3.2.0]hept-6-ylidene]aminooxyacetic acid;

N-[2-endo-hydroxy-3-exo-(3-hydroxy-hept-1-trans-enyl)bicyclo[3.2.0]hept-6-ylidene]aminooxyacetic acid;

N-[2-endo-hydroxy-3-exo-(3-hydroxy-oct-1-trans-enyl)bicyclo[3.2.0]hept-6-ylidene]aminooxyacetic acid;

N-[2-endo-hydroxy-3-exo-(3-hydroxy-non-1-trans-enyl)bicyclo[3.2.0]hept-6-ylidene]aminooxyacetic acid;

N-[2-endo-hydroxy-3-exo-(3-hydroxy-dec-1-trans-enyl)bicyclo[3.2.0]hept-6-ylidene]aminooxyacetic acid;

N-[2-endo-hydroxy-3-exo-(3-hydroxy-undec-1-trans-enyl)bicyclo[3.2.0]hept-6-ylidene]aminooxyacetic acid;

N-[2-endo-hydroxy-3-exo-(3-hydroxy-dodec-1-trans-enyl)bicyclo[3.2.0]hept-6-ylidene]aminooxyacetic acid;

N-[2-endo-hydroxy-3-exo-(3-hydroxy-3-cyclopentyl-prop-1-trans-enyl)-bicyclo[3.2.0]hept-6-ylidene]aminooxyacetic acid;

N-[2-endo-hydroxy-3-exo-(3-hydroxy-3-cyclohexyl-prop-1-trans-enyl)-bicyclo[3.2.0]hept-6-ylidene]aminooxyacetic acid;

N-[2-endo-hydroxy-3-exo-(3-hydroxy-3-phenylprop-1-trans-enyl)bicyclo[3.2.0]hept-6-ylidene]aminooxyacetic acid; and N-[2-endo-hydroxy-3-exo-(3-hydroxy-3-(2-trifluoromethyl)phenylprop-1-trans-enyl)bicyclo[3.2.0]hept-6-ylidene]aminooxyacetic acid.

PREPARATION PROCEDURES

Compounds wherein $R_1$ is hydroxy and $R_2$ is hydrogen are prepared according to the Reaction Scheme 1.

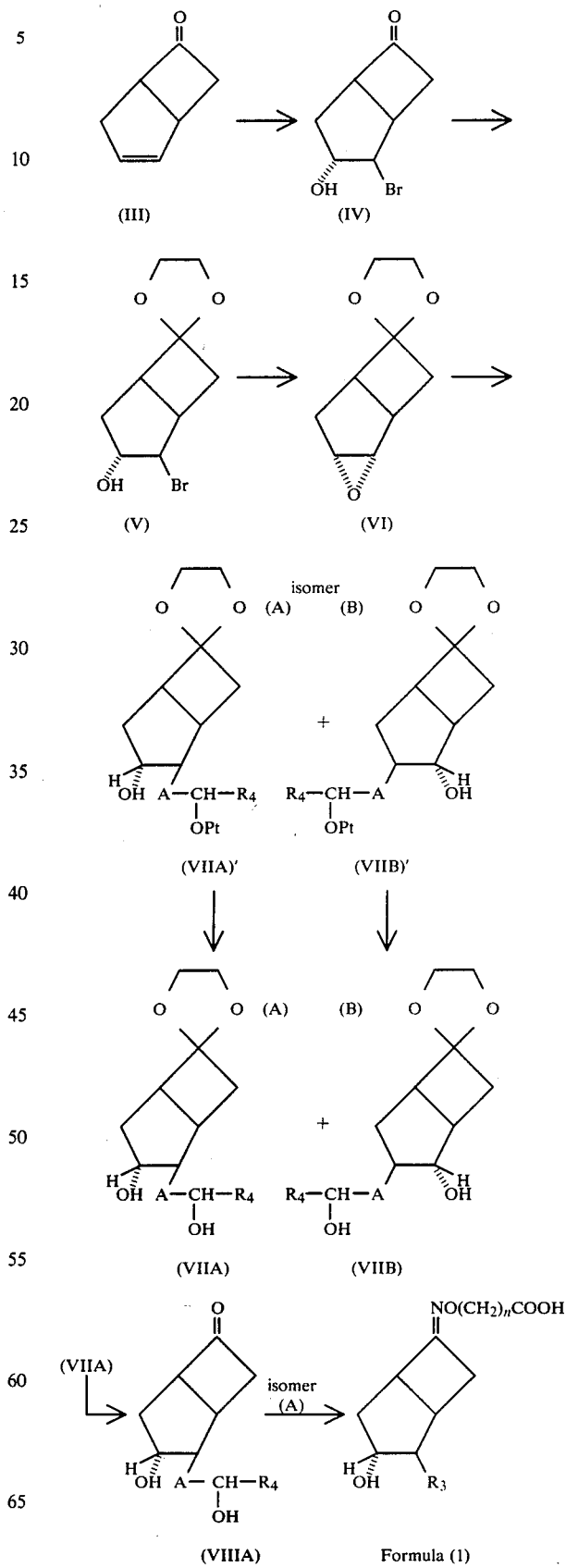

-continued
REACTION SCHEME I

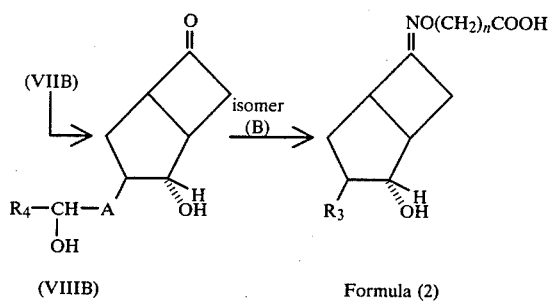

(VIIIB)  Formula (2)

In the detailed description, the Roman numerals in parentheses show the steps in the reaction scheme.

Synthesis of compounds (I) through (VI) is described in detail in U.S. Pat. No. 4,272,629 to Roberts.

The synthesis of the compounds of formula (1) and (2) begins with reaction of cyclopentadiene (I) with dichloroacetyl chloride forming 7,7-dichlorobicyclo[3.2.0]hept-2-en-6-one (II) which, when reacted with zinc dust, results in formation of bicyclo[3.2.0]hept-2-en-6-one (III). *J. Org. Chem.*, 37:2363 (1972).

Bicyclo[3.2.0]hept-2-en-6-one is reacted with 1,3-dibromo-5,5-dimethylhydantoin in the presence of aqueous acid to form the bromohydrin (IV) which, in turn, is reacted with ethylene glycol to give the acetal (V). The acetal is subsequently reacted with sodium hydroxide in methanol to form the epoxy acetal (VI). Cave et al, *J.C.S.* Perkin I.:2955 (1979).

The bicyclic epoxy acetal (VI) can be reacted with a variety of metal-organic reagents of general structure M—R$_3'$ to give the regioisomeric products of epoxide cleavage, VIIA' and VIIB', where

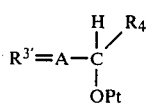

in which A and R$_4$ are as previously defined and Pt is a protecting group for the side chain hydroxyl function. Suitable protecting groups include, but are not limited to, silyl ethers, tertiary alkyl ethers, e.g. tert-butyl, (optionally substituted) triphenylmethyl ethers, acetals such as tetrahydropyranyl ethers, and the like. Usually trialkyl silyl ethers are preferred, and particularly preferred are the tert-butyldimethylsilyl derivatives. These ethers are prepared from the corresponding carbinols by standard procedures well known to those skilled in the art; the tert-butyldimethylsilyl ethers in particular enjoy obiquitous use in prostaglandin chemistry and can be conveniently prepared by reaction of the appropriate carbinol with tert-butyldimethylsilyl chloride in N,N-dimethylformamide solution in the presence of imidazole, which functions in the dual capacities of specific catalyst for the silylation and as base, to neutralize the hydrochloric acid which constitutes the other reaction product. Representative procedures for preparing the silyloxy and other protected carbinols are given in the references for preparation of the various types of organometallic reagents that can be employed to effect alkylative opening of the epoxy acetal (VI).

Organometallic reagents of the alkynyl type are prepared from the corresponding 1-alkyn-3-ols, which in turn can be readily obtained by reaction of an acetylenic Grignard reagent, i.e. ethynyl magnesium halide, or lithium acetylide, with aldehydes

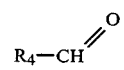

furnishing ethynyl carbinols

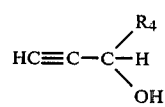

Protection of the hydroxyl group gives the corresponding ethers

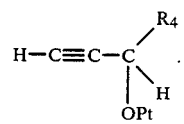

Conversion to an organometallic reagent can now be effected, usually by exchange reaction with a stoichiometric quantity of a more reactive organometallic, e.g. an alkyl Grignard reagent RMgCl to give the acetylene Grignard reagent

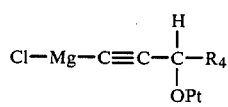

or with an alkyl lithium reagent R Li to furnish the corresponding lithium acetylide. Reaction of the latter with, e.g., dimethyl aluminum chloride furnishes an alane

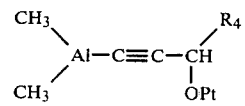

This species may be further reacted with an alkyl lithium reagent, e.g. CH$_3$Li, to give yet another organometallic reagent useful for effecting alkylative epoxide opening, namely the alanate

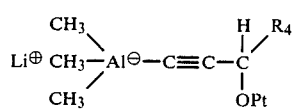

Detailed descriptions of alane preparations and their reaction with cyclopentene-derived epoxides are given in *Tetrahedron Lett.*;3899 (1973); of alanate preparations and acetylenic Grignards (U.S. Pat. 4,197,295) and of lithium alkynyl species, inter alia by Stork et al, *J. Amer. Chem. Soc.*, 96, 7114 (1974); ibid., 97, 4745 (1975).

The novel products of our invention in which A is a trans-olefinic linkage can be prepared according to the Scheme from the acetylenic carbinol products of epoxide opening

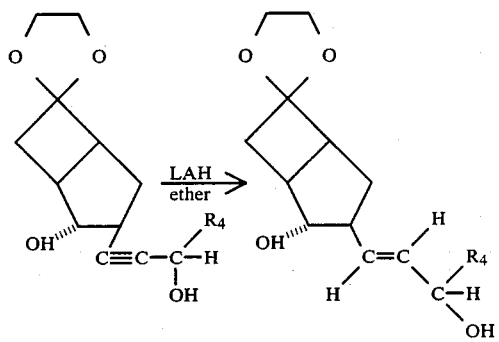

by reduction, e.g. with lithium aluminum hydride, to furnish the trans-olefinic carbinols (see 1975 Stork and Isobe ref. above for an example utilizing this LAH reduction in a total synthesis of prostaglandins). A convenient and general method for preparation of the olefinic species involves preparation of organocopper reagents containing the desired olefinic moiety. These can be prepared easily from the vinyl lithium derivatives, which in turn are obtained by reaction of the appropriate trans-vinyl halide, preferably iodide, with an alkyl lithium reagent or with lithium metal. Detailed descriptions of the preparation of various olefinic organocuprate reagents representing both hetero- and homocuprate structure types, and their reactions with compound VI and related bicyclic epoxy acetals are given in U.S. Pat. No. 4,272,629 to Roberts and references therein.

The products of our invention in which the chain is fully saturated (A=—CH$_2$CH$_2$—) may be prepared by direct introduction of the saturated side chain via the corresponding organometallic reagent

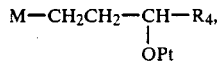

which can be prepared by standard methods from the corresponding halides

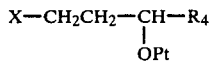

by reaction in an ethereal solvent, preferably tetrahydrofuran, with a metal, e.g. Mg or Li, or by exchange with a more reactive organometallic reagent, e.g. an aryl lithium derivative. The saturated side chain species may also, and preferably, be prepared by catalytic hydrogenation, using noble metal catalysts (palladium on carbon, rhodium on carbon, rhodium on alumina, platinum), of either the alkynyl or alkenyl side chain products. These hydrogenations proceed with facility by stirring a solution of the substrate at ambient temperature and low hydrogen pressures (1-4 atm.) in the presence of 1-10% (w/w) of a catalyst. A variety of solvents may be employed, alcohols such as methanol and ethanol being particularly useful. Reaction times vary from less than 1 to 24 hours depending on the solvent, the nature and quantity of the catalyst employed, and the structure of the substrate being reduced, but can be conveniently monitored since when the stoichiometric quantity of hydrogen has been taken up (1 mole equiv. for alkene, 2 mole equiv. for alkyne starting materials) the reduction to saturated alkylene side chain is essentially complete. Catalyst is removed from the hydrogenation mixture by filtration, preferably through a pad of diatomaceous earth. Evaporation of the filtrates under reduced pressure then furnishes a residue of the desired 2- or 3-exo-alkylidene bicycloheptan-6-one derivative, typically requiring no further purification. When desired, final purification is readily effected by preparative layer or column chromatography on silica gel. When the ω-chain being hydrogenated terminates in a phenyl ring, a palladium/carbon catalyst is preferred, and when said phenyl ring carries 1-2 halogen substituents, in particular Br or I, reduction of the C—C multiple bond(s) may be accompanied by some degree of reductive dehalogenation. Such dehalogenated by products can usually be separated by chromatography but, if this proves tedious, those particular functionalized chains can be introduced directly in their saturated form (see above) by reaction of the corresponding terminal Grignard or organolithium reagents with epoxyacetal VI.

An organometallic reagent may react with epoxyacetal VI at either terminus of the oxirane ring to furnish two regioisomeric alcohols, and in fact both regioisomers are obtained. For example, reaction of VI with 3-(tert-butyldimethylsilyloxy)oct-1-ynyl dimethyl alane furnishes the regioisomeric alkynyl carbinols VIIA—3-endo-hydroxy-2-exo-(3-hydroxyoct-1-ynyl)spiro[bicyclo-[3.2.0]heptan-6,2'-[1.3]dioxolan]; and VIIB—2-endo-hydroxy-3-exo-(3-hydroxyoct-1-ynyl)spiro[bicyclo-[3.2.0]heptan-6,2'-[1,3]dioxolan].

The two isomers are separated chromatographically, and the alkynol acetals VIIA and VIIB are each reacted with sulfuric acid to effect acetal hydrolysis furnishing 3-endo-hydroxy-2-exo-(3-hydroxy-oct-1-ynyl)bicyclo[3.2.0]heptan-6-one (VIIIA) and 2-endo-hydroxy-3-exo-(3-hydroxy-oct-1-ynyl)bicyclo[3.2.0]heptan-6-one (VIIIB), respectively. (J. Chem. Soc., Perkin I, 852, (1980)).

For the preparation of 3-aminooxypropionic acid the methods described in J. Am. Chem. Soc., 77, page 2345 (1955), in U.S. Pat. No. 2,762,815, and in Zhur. Obshchei Khim. 31, 1992 (1961) were modified as follows. Acetone oxime in dioxane is reacted with sodium methoxide and methyl acrylate, acidified and distilled to provide the acetone oxime of 3-aminoxypropionic acid, which is subsequently hydrolyzed to form 3-aminooxypropionic acid hydrochloric acid salt.

In carrying out this reaction, as set forth above, typically acetone oxime dissolved in dioxane is added to sodium methoxide and the mixture is stirred from 15 minutes to about 2 hours, preferably 30 minutes, then cooled to 0° C. with an ice bath for about 1 hour or until 0° C. temperature of the mixture is achieved. After methyl acrylate is added, the resulting mixture is warmed to room temperature and stirred for about 2 to 5 hours, preferably 3 hours. After acidifying and purifying by distillation, the oxime adduct is heated in the presence of an acid catalyst, preferably 5N hydrochloric acid, at 40° to about 80° C., preferably to 60° C., until the reaction is complete.

The synthesis of 4-aminooxybutyric acid and 5-aminooxyvaleric acid are described in Tetrahedron, 23, 4441 (1967). Benzophenone oxime in N-methylpyrrolidone is reacted first with sodium then with γ-butyrolactone to provide N-diphenylmethylidene-4-aminooxybutyric acid which is subsequently hydrolyzed to form 4-aminooxybutyric acid. 5-aminooxyvaleric acid hydrochloric acid salt is prepared similarly by substituting γ-butyrolactone with σ-valerolactone. Aminooxyacetic acid is available as the hemihydrochloride from a commercial source.

Bicycloheptanone alkynol formula (VIIIB) is reacted with ω-aminooxy carboxylic acids having 2-5 carbon atom chain length to result in formation of the corresponding N-[2-endo-hydroxy-3-exo-(3-hydroxy-oct-1-ynyl)bicyclo[3.2.0]hept-6-ylidene]-ω-aminooxy alkanoic acids. Bicycloheptanone alkynol formula (VIIIA) is reacted with ω-aminoxy acids of 2-5 carbon atoms to form the isomeric N-[3-endo-hydroxy-2-exo-(3-hydroxy-oct-1-ynyl)bicyclo-[3.2.0]hept -6-ylidene]-ω-aminooxy alkanoic acids.

In carrying out this reaction, as set forth supra, typically one equivalent of bicycloheptanone and 2 equivalents of sodium acetate are dissolved in alcohol, preferably methanol and added to a salt, preferably hydrochloride, of the aminooxy acid also dissolved in stirred at ambient temperature for 0.5 to 7 hours until the reaction is determined to be complete. After removing the alcohol, the residue is extracted several times with an organic solvent such as ethyl acetate, methylene chloride and the like. Combined extracts are washed with aqueous salt solution, dried, e.g. over $MgSO_4$, and evaporated under reduced pressure. The residue is purified by recrystallization from a suitable organic solvent or mixture of solvents, e.g. ethyl acetate-heptane, to furnish the pure oximino acid.

REACTION SCHEME 2

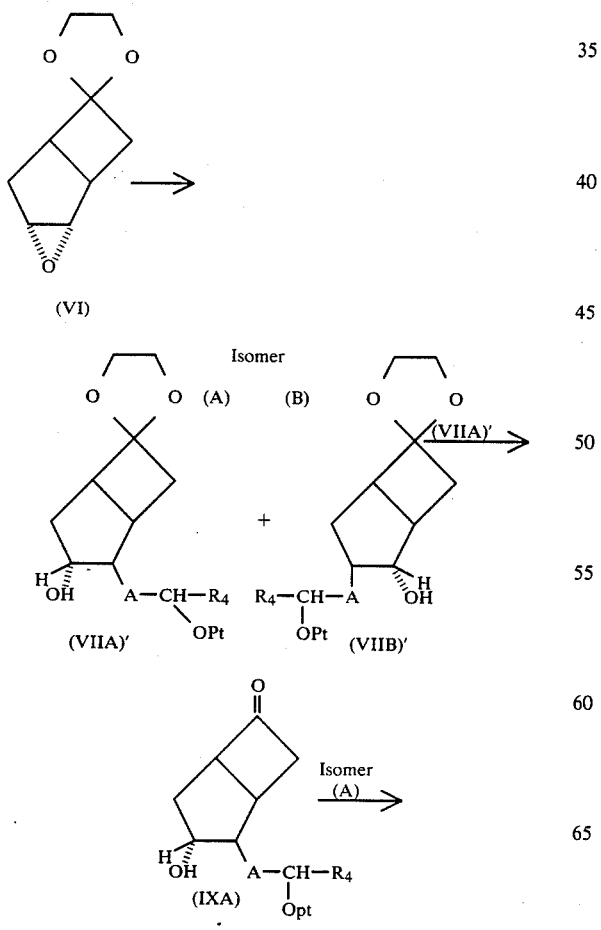

-continued
REACTION SCHEME 2

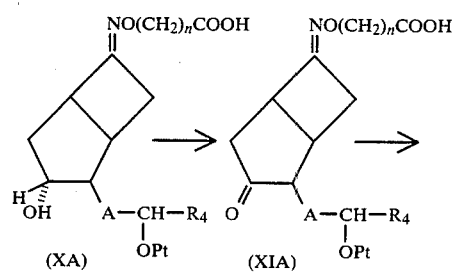

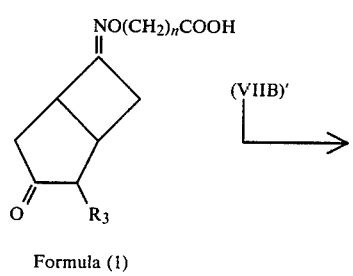

Formula (1)

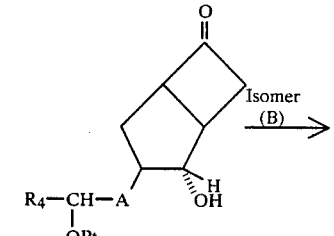

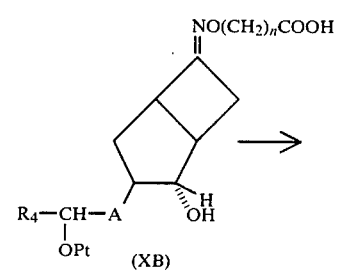

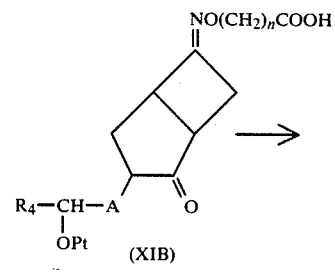

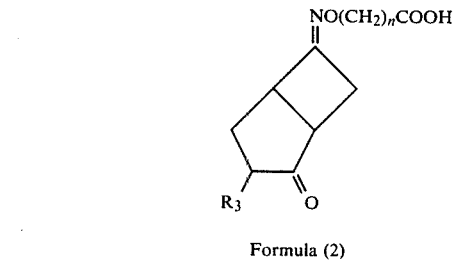

Formula (2)

The novel compounds of our invention wherein the groups $R_1$ and $R_2$ taken together denote a carbonyl group are readily prepared according to the Reaction Scheme by judicious selection of a protecting group for the 3-hydroxyl function in the organometallic reagent used to open epoxy acetal VI such that it will be sufficiently stable to remain intact during hydrolytic cleavage of the cyclic acetal, i.e. VIIA' IXA or VIIB' IXB in the reaction flow sheet.

The resulting ketone is then reacted with the appropriate ω-aminoxycarboxylic acid (IXA XA) or (IXB XB) as described above, and the free ring hydroxyl group in the product is then oxidized, e.g., with a chromium trioxide reagent such as that of Jones or Collins, or with a dimethyl sulfoxide reagent (the Moffatt reagent, or various modifications thereof), or a dimethyl sulfonium species such as that described by Corey and Kim in *J. Am. Chem. Soc.*, 94:7586 (1972) to furnish the corresponding ring ketone XIA or XIB, respectively. Hydrolysis of the remaining protecting group in the ω-side chain then furnishes the compounds of our invention of formula (1) or (2) wherein $R_1$ and $R_2$ taken together are a carbonyl group.

A useful protecting group for this sequence of reactions is the tert-butyldimethylsilyloxy group. Employment of this group in the metallorganic reagent used to open epoxide (VI) furnishes a silyloxy hydroxyacetals VIIA' and VIIB'. Selective hydrolysis of the ketal function can now be effected by exchange ketalization. Thus, when a solution of the protected ketal VII' in a ketonic solvent, preferably acetone, is allowed to stand at temperatures between −30 and 20° C. in the presence of a catalytic amount of a mineral acid or strong organic acid, the ketal function is transferred to the solvent to give as the predominant reaction product the silyloxy-hydroxyketone (IX) which is isolated, after neutralization of the reaction mixture, by conventional means. The exchange reaction is conveniently carried out at about 0° C., and p-toluenesulfonic acid is a preferred acid catalyst. Progress of the ketal exchange is conveniently monitored by T.L.C.

Preparation of the oxime products results in an equilibrium mixture of syn- and anti- oxime isomers, which can be separated by chromatography over silica gel. While only one geoisomer may be depicted in the accompanying structural diagrams, this invention encompasses both syn- and anti- oxime geoisomers and mixtures thereof in any proportions.

The structures depicted herein, including the novel compounds of our invention, have multiple chiral centers and are optically active. While for illustrative purposes only one optical isomer is depicted, our invention encompasses all optical isomers and mixtures thereof, said mixtures including racemates and diastereomeric mixtures in all proportions. If the product compounds of our invention are prepared from optically inactive starting materials and without employment of chiral reagents, the products will be obtained as (optically inactive) racemic mixtures. Enantiomerically pure materials can be obtained, e.g., by resolution of the final product acids via their salts with optically active amines according to methods well-known in organic chemistry and specifically in the chemistry of prostaglandins.

An alternative route to optically active products proceeds via chiral intermediates. An efficient synthesis of both bicyclo [3.2.0]hept-2-en-6-one enantiomers, involving enantioselective reduction by fermenting baker's yeast of the racemic bicycloheptenone, has been described (Davis et al., *J. Chem. Soc.*, Chem. Commun., 1317, 1981). Both enantiomeric ω-side chain alcohols, e.g. (R)- and (S)-1-octyn-3-ols, are also readily available (J. Fried et al., *Ann. N.Y. Acad. Sci.*, 180, 39, (1971)). Thus, condensation of an organometallic derived from optically active side chain alcohol with one optical isomer of bicycloheptanone expoxy acetal (VI) will lead to a single optical isomer product (VII) and eventually to the corresponding pure optical isomer products of our invention. Reaction of optically active side chain with racemic bicycloheptanone acetal epoxide, or racemic side chain with optically active bicycloheptanone acetal epoxide, will lead to mixtures of diastereomeric products which can be employed per se or can be separated e.g. by chromatographic methods to furnish enantiomerically pure materials.

This method is shown in Reaction Scheme 3 wherein a diastereisomeric mixture of 3-exo-(3S-t-butyldimethylsilyloxyalk-1-ynyl)spiro[bicyclo(3.2.0)heptan-6,2'-(1,3-dioxolan]-2-endo-ols (VIIB' in Reaction Scheme 1) is converted through reaction with dicobalt octacarbonyl in diethyl ether into their dicobalthexacarbonyl complexes (αS-XIIB and βS-XIIB), which are separated chromatographically. The isolated complexes are converted with ceric ammonium nitrate back into their parent enantiomeric 3-exo-(3βS-t-butyldimethylsilyloxyalk-1-ynyl)spiro[bicyclo(3.2.0)heptan-6,2'-(1,3)dioxolan]-2-endo-ols and 3-exo-(3βS-t-butyldimethylsilyloxyalk-1-ynyl)spiro[bicyclo(3.2.0)heptan-6,2'-(1,3)chromatographically. The isolated complexes are converted with ceric ammonium nitrate back into their parent enantiomeric 3-exo-(3βS-t-butyldimethylsilyloxyalk-1-ynyl)spiro[bicyclo(3.2.0)heptan-6,2'-(1,3)dioxolan]-2-endo-ols and 3-exo-(3αS-t-butyldimethylsilyloxyalk-1-ynyl)spiro[bicyclo(3.2.0)heptan-6,2'-(1,3)dioxolan]-2-endo-ols. These are converted into the corresponding 2-endo-hydroxy-3-exo-(3βS-hydroxyalk-1-ynyl)bicyclo[3.2.0]heptan-6-one (βS-VIIIB) and 2-endo-hydroxy-3-exo-(3αS-hydroxyalk-1-ynyl)bicyclo[3.2.0]heptan-6-one (αS-VIIIB) through hydrolysis with dilute aqueous acid. These compounds are converted into their N-[2-endo-hydroxy-3-exo-(3βS-hydroxyalk-1-ynyl)bicyclo[3.2.0]hept-6-ylidene]aminooxyalkanoic acid (βS-Formula 2) and N-[2-endo-hydroxy-3-exo-(3αS-hydroxyalk-1-ynyl)-bicyclo[3.2.0]hept-6-ylidene]aminooxyalkanoic acid (αS-Formula 2).

REACTION SCHEME 3
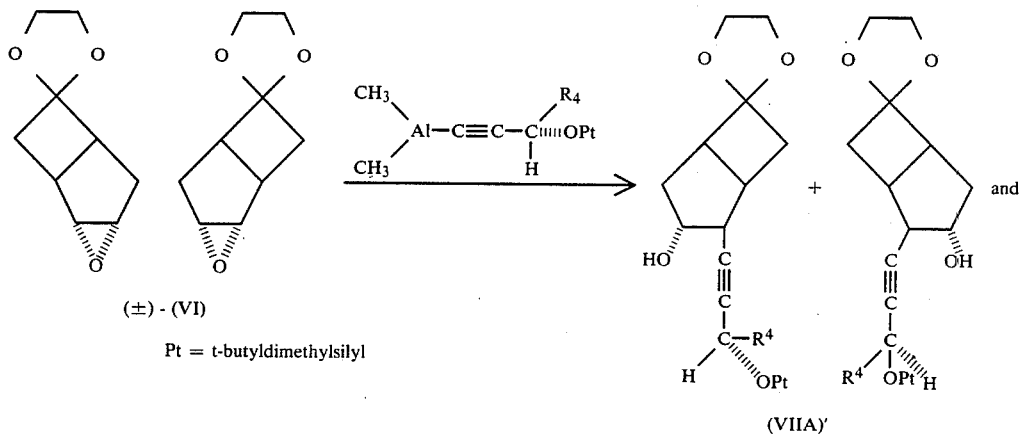
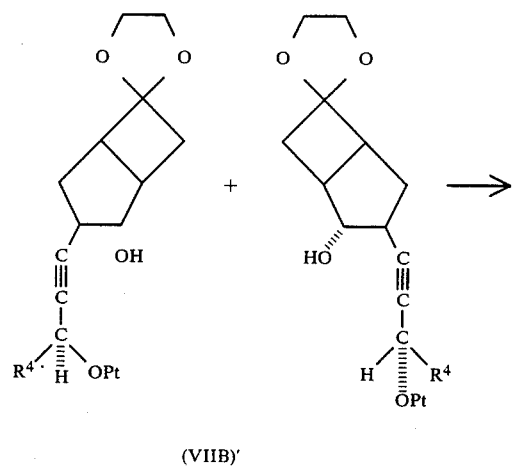
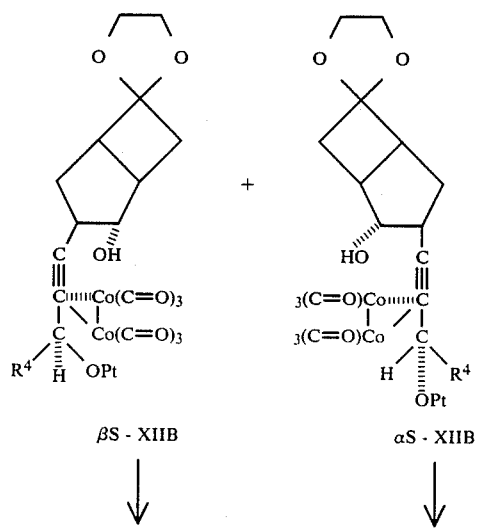

-continued
REACTION SCHEME 3

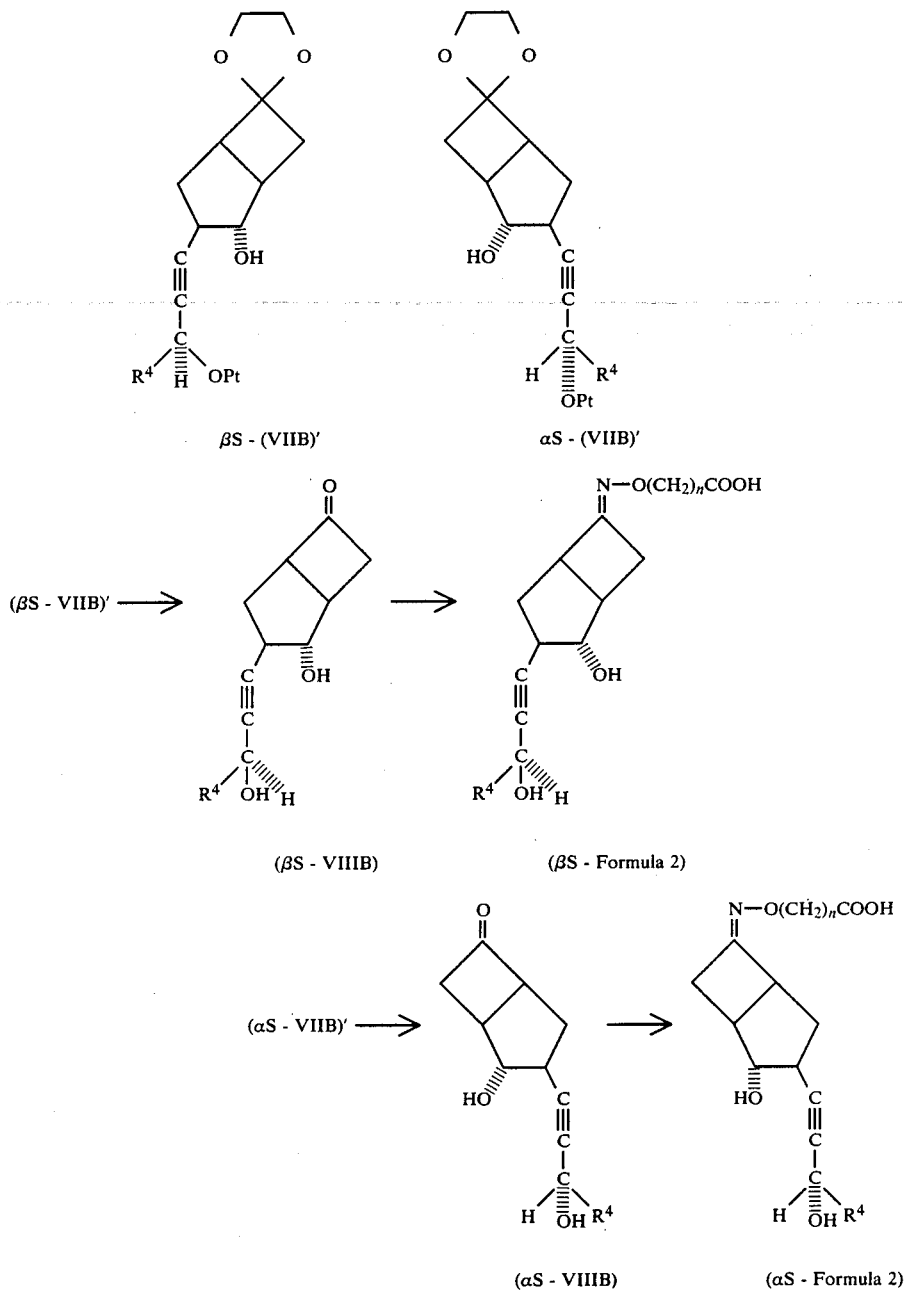

As used herein the pharmaceutically acceptable nontoxic salt derivatives of the compounds of formula (1) and formula (2) are prepared by treating the free acids with an appropriate amount of pharmaceutically acceptable base. Representative pharmaceutically acceptable bases are sodium hydroxide, potassium hydroxide, lithium hydroxide, ammonium hydroxide, calcium hydroxide, magnesium hydroxide, ferrous hydroxide, zinc hydroxide, copper hydroxide, manganous hydroxide, aluminum hydroxide, ferric hydroxide, manganic hydroxide, isopropylamine, trimethylamine, diethylamine, triethylamine, tripropylamine, ethanolamine, 2-dimethylaminoethanol, 2-diethylaminoethanol, lysine, arginine, histidine, procaine, choline, betaine, ethylenediamine, glucosamine, methylglucamine, theobromine, purines, piperazine, piperidine, N-ethylpiperidine, polyamine resins and the like. The reaction is conducted in water, alone or in combination with an inert, water-miscible organic solvent, at a temperature of from about 0° C. to about 100° C., preferably at room temperature. Typical inert, water-miscible organic solvents include methanol, ethanol, isopropanol, butanol, acetone, dioxane or tetrahydrofuran. The molar ratio of compounds of formula (1) or (2) to base used are chosen to provide the ratio desired for any particular salt. For preparing, for example, divalent cation salts such as the calcium or magnesium salts the free acid starting material of formula (1) or (2) is treated with at least one-half molar equivalent of pharmaceutically acceptable base to yield a neutral salt. Similarly, for the trivalent cation aluminum salts, at least one-third molar equivalent of the aluminum base is employed if a neutral salt product is desired.

The novel free carboxylic acids (1) and (2) of our invention can be reliberated from their respective salts by treating said salts with at least stoichiometric quantities of a strong acid, preferably an inorganic acid, e.g., hydrochloric acid, sulfuric acid, and the like, at temperatures ranging from about 0° C. to about 50° C., preferably at room temperature.

The pharmaceutically acceptable non-toxic esters of the novel acids (1) and (2) of our invention can be prepared, e.g. by esterifying the corresponding free acids with a solution of the appropriate diazoalkane in a suitable inert solvent such as diethyl ether. An alternative and general method for producing the esterified acids of our invention comprises reaction of a benzene solution of the carboxylic acid with an alkyl halide in the presence of the organic base diazabicycloundecane (DBU) at temperatures from about 20° C.–80° C., and for about 1–12 hours. These conditions are particularly useful for esterifying acids containing labile functionality in the molecule, such as the prostaglandins and their synthetic analogues, since they avoid the use of acid catalysts and in fact involve no harsh reagents. (N. Ono et al, *Bull. Chem. Soc. Japan*, 51, 2401–2404 (1978)).

Typical esters are those esters derived from methyl alcohol, ethyl alcohol, propyl alcohol, isopropyl alcohol, butyl alcohol, 2-butyl alcohol, 2-pentyl alcohol, isopentyl alcohol, 2-hexyl alcohol, and the like.

Alternatively, the alkyl esters can be prepared by transesterification, catalyzed by the corresponding alkoxide according to methods known in the art. It is preferred in preparing the esters via transesterification to go from a lower ester to a higher ester, e.g., from the methyl ester to the isoamyl ester. However, by using a substantial excess of a lower alcohol, a higher ester can be transesterified to a lower ester; thus, for example, by using a substantial excess of ethanol, the hexyl ester is converted by transesterification to the ethyl ester.

Salts of the compounds of formula (1) and (2) may be interchanged by taking advantage of differential solubilities of the salts volatilities or activities of the acids, or by treating with the appropriately loaded ion exchange resin. For example, the interchange is effected by the reaction of a salt of the compounds of formula (1) or (2) with a slight stoichiometric excess of an acid of a lower pKa than the acid component of the starting salt. This conversion is carried out at a temperature between about 0° C. and the boiling point of the solvent being used as the medium for the procedure.

UTILITY AND ADMINISTRATION

The compounds of the present invention are synthetic prostaglandin analogs and display the spectrum of biological activities associated with prostacyclin (PGI$_2$). They are useful for the treatment of cardiovascular disorders; in particular they are potent platelet aggregation inhibitors. Accordingly, these compounds are useful in treating cardiovascular disorders with thrombotic complications. They also are useful as vasodilatory, antisecretory and antihypertensive agents.

Because these compounds are synthetic prostaglandin analogs and specifically analogs of prostacyclin PGI$_2$ they display the spectrum of activities associated with prostaglandin. However, in contrast to prostacyclin, whose therapeutic potential is severely compromised by its extreme chemical instability, the compounds of our invention retain high biological activity while displaying much greater chemical stability, a combination of attributes identifying them as promising agents for prophylactic and/or therapeutic use particularly in the treatment of cardiovascular dysfunction and disease.

Administration of the active compounds in the pharmaceutical composition described hereinafter can be via any of the accepted modes of administration for agents which affect the cardiovascular system. These methods include oral, parenteral and otherwise systemic administration. Depending on the intended mode, the composition may be in the form of solid, semi-solid or liquid dosage forms, such as, for example, tablets, suppositories, pills, capsules, powders, liquids, suspension, or the like, preferably in unit dosage forms suitable for single administration of precise dosages. The composition will include a conventional pharmaceutical carrier or excipient and an active compound of formula (1) or (2) and/or the pharmaceutically acceptable salts thereof and, in addition, may include other medicinal agents, pharmaceutical agents, carriers, adjuvants, etc.

The present invention further relates to a method for treating symptoms associated with cardiovascular disorders in mammals, which method comprises administering to a subject in need thereof an effective amount of a compound selected from those represented by formulas (1) and (2) or their pharmaceutically acceptable non-toxic salts or esters, or a pharmaceutical composition incorporating such compound(s) as an active ingredient.

The present invention still further relates to pharmaceutical compositions useful for treating cardiovascular disorders. These compositions comprise an effective amount of a compound selected from those represented by formulas (1) and (2) or their pharmaceutically acceptable non-toxic salts or esters in acceptable, non-toxic carrier.

The amount of active compound administered will of course, be dependent on the subject being treated, the severity of the affliction, the manner of administration and the judgment of the prescribing physician. However, an effective dosage will be in the range of 0.001–15 mg/kg/day, preferably 0.01–3 mg/kg/day. For an average 70 kg human, this would amount to 0.07–1000 mg per day, or preferably 0.7–210 mg/day.

The novel compounds of this invention may be formulated with suitable pharmaceutical vehicles known in the art to form particularly effective cardiovascular composition. Generally, an effective amount of active ingredient is about 0.001% w to about 10% w of the total formulated composition. The rest of the formulated composition will be about 90% w to about 99.999% w of a suitable excipient.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound(s) in an amount effective to alleviate the symptoms of the subject being treated.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795.

For systemic administration via suppository, traditional binders and carriers include, e.g. polyalkylene glycols or triglycerides. Such suppositories may be formed from mixtures containing active ingredient in the range of 0.5%–10%; preferably 1–2%.

The following Preparations and Examples serve to illustrate the invention and make the invention enabling. They should not be construed as narrowing it or limiting its scope in any way.

In the Preparations and Examples, the use of Roman numerals refers to the reaction steps on Reaction Scheme.

PREPARATION PROCEDURES FOR COMPOUNDS OF THE FORMULA VIII

Preparation 1

Preparation of 7,7-dichlorobicyclo(3.2.0)hept-2-en-6-one

Over a period of 1.5 hr 21.7 g of dry triethylamine in 200 ml of hexane was added to a vigorously stirred solution mixture of 27.2 g of freshly distilled cyclopentadiene (I), 30.5 g of dichloroacetyl chloride, and 200 ml of hexane (dried over molecular sieves). After stirring for 15 hours under an atmosphere of nitrogen, the reaction mixture was filtered and the filter cake was washed with hexane. The solvent was removed under vacuum, yielding a 35.2 g of liquid, which, when redistilled under vacuum, afforded 30 g of 7,7-dichlorobicyclo(3.2.0)hept-2-en-6-one (II).

Preparation of bicyclo(3.2.0)hept-2-en-6-one 5.00 g (0.028 mol) of 7,7-dichlorobicyclo(3.2.0) hept-2-en-6-one in 5 ml of glacial acetic acid was added dropwise to a vigorously stirred suspension of 11.0 g of zinc dust in 15 ml of glacial acetic acid at room temperature. After addition was completed, the temperature was raised to and maintained at 70° C. for 40 minutes. A thin layer chromatography (TLC) analysis performed at that time indicated no remaining starting material. The reaction mixture was then cooled and treated with ether. Zinc residue was filtered. The ethereal layer was washed with saturated solution of $Na_2CO_3$ to remove remaining acetic acid and subsequently dried over the magnesium sulfate. The solvent was then evaporated and the product, bicyclo(3.2.0)hept-2-en-6-one (III), was isolated by distillation. The total yield of the product was 2.99 g (95%). The homogeneity of the product was determined by TLC.

Preparation 2

Conversion of bicyclo(3.2.0)hept-2-en-6-one into the epoxyacetal of Formula (VI)

To 1 g of bicycloheptenone (III) dissolved in the mixture of 20 ml of acetone and 5 ml of water, 1.5 g of 1,3-dibromo-5,5-dimethyl-hydantoin was added in portions under constant stirring. After 16 hours at room temperature the solvent was evaporated under reduced pressure. The residue was dissolved in 10 ml of water and extracted several times with dichloromethane. Obtained organic extracts were washed with brine, dried over magnesium sulfate and evaporated. A residuum in the form of a yellow oil was then separated by silica-gel column chromatography with solvent mixture of 20% ethyl acetate in light petroleum to obtain 2-bromo-3-hydroxybicyclo[3.2.0]heptan-6-one (IV) (U.S. Pat. No. 4,272,629).

A mixture of 17.5 g of this bromohydrin, 8.0 g of ethylene glycol and 0.17 g of toluene-p-sulfonic acid monohydrate was heated under reflux in 175 ml of benzene under nitrogen. Water was removed using a Dean-Stark trap, and after 6 hours the solution was cooled and washed with an 8% (weight/volume) solution of sodium bicarbonate-water and water. The dried (over $MgSO_4$) solution was decolorized with charcoal and the solvent was evaporated to give a residue of bromohydrin-acetal represented by formula (V).

10.6 g of the bromohydrin-acetal was dissolved in 25 ml of sodium hydroxide in 75 ml of methanol. The whole solution was incubated for 20 hours at 20° C., then 200 ml of water was added prior to extraction with 30 ml of dichloromethane. Extraction was repeated four times, extracts were combined, washed with water, dried and evaporated. Evaporated oily residuum was distilled and the product of distillation slowly crystalized into the epoxyacetal represented by Formula (VI).

Preparation 3

Preparation of 3-OH Alkynes and 3-OH Alkenes

3.A. Preparation of 1-yn-3-ols

A rapid stream of acetylene was passed through a solution of 2M methyl magnesium bromide (100 ml) in THF until no more methane evolution was observed. 10 g of hexanal was added at 0° C., stirred for ½ h and a saturated solution of $NH_4Cl$ was added. The organic product was isolated by extraction with ether. The ether solution was washed with water, brine, dried over $MgSO_4$ and evaporated to give a liquid which was purified by distillation.

3.B. Preparation of 1-Iodo-trans-1-octen-3-ol

Step 1

To 400 ml of distilled methylene chloride 44 g of aluminum trichloride and 40 g of hexanoyl chloride is added. The reaction mixture is maintained at 15° C. with an external cooling bath. Over the period of ¼ hours 27 ml of dry acetylene is delivered. The temperature is kept at about 15° C. The progress of the reaction is followed by I.R (disappearance of acid chloride carbonyl). Upon completion of the reaction, the reaction solution is transferred to 800 ml of water at 5° C. with vigorous stirring. 500 ml of methylene chloride is added and methylene chloride layer is separated. The aqueous phase is extracted with 100 ml of methylene chloride. Combined methylene chloride extracts are washed 3 times with 100 ml of water, dried over anhydrous sodium sulphate, and the solvent evaporated in vacuo. The crude oil is purified by distillation under high vacuum.

Step 2

30 g of sodium iodide is stirred with 80 ml of distilled acetone. 20.4 g of crude oil (obtained during Step 1) in acetone is added. The resulting mixture is kept under constant reflux for approximately 8 hours. The mixture is filtered through a Buchner funnel, the filter cake washed with 20 ml of acetone, and the combined filtrates concentrated under reduced pressure at a temperature below 40° C., ca. 50 ml of benzene being added to displace all the acetone. The aqueous phase is extracted twice with 20 ml of benzene. The benzene layer is washed to neutrality with water, then dried over anhydrous sodium sulphate. The solvent is removed in vacuo to give approximately 30 g of oil. The oil is dissolved in 50 ml of diethyl ether/hexane (25:75, v:v) and filtered through 20 g of silica gel. The resulting oil is distilled under high vacuum to give 26.8 g of product.

Step 3

32 g of iodoketone in 50 ml of benzene is under nitrogen to 0°-5° C. 28 ml of 65% Vitrid TM is added dropwise with constant stirring. The reaction is followed by TLC employing a solvent system ether/hexane (25:75, v:v). 9.3 ml of sulfuric acid in 50 ml of water is added dropwise under constant stirring maintaining the temperature below 20° C. The agueous phase is separated and extracted twice with 20 ml of benzene. The benzene layer is washed to neutrality with water, then brine and dried over anhydrous sodium sulphate. The solvent is removed in vacuo to give approximately 30 g of oil. 12.3 g portion of the oil is dissolved in 50 ml of 20% diethyl ether/80% hexane and filtered through 200 g of silica gel. Evaporation of the appropriate fractions yields 11 g. Distillation of 10 g of the obtained oil under high vacuum furnishes 8.2 g of pure 1-iodo-trans-1-octen-3-ol.

3.C. Preparation of Silyl Ethers

Resulting compounds of both Preparations 3.A and 3.B. are then submitted to Preparation 3.C. to obtain final compounds used in Preparation 4.

To a solution of 3-hydroxyoct-1-yne (see Preparation 3.A.) (2.89 g, 0.02 mol), in N,N-dimethylformamide (DMF), cooled to 0° C., was added imidazole (2.1 g), followed by tert-butyldimethylchlorosilane (3.1 g, 0.02 mol), and the mixture was stirred for 3 h. Water (80 ml) and hexane (80 ml) were added; the organic layer was separated and combined with 2×80 ml of hexane extractions of the aqueous layer. The solvent was removed (in vacuo), after drying over sodium sulfate, to give a crude residue (4.3 g) which was chromatographed on silica gel (80 g), eluting with ethyl acetate-hexane (2:1, v/v) to afford 3-tert-butyldimethylsilyloxyoct-1-yne. *JACS*, 94, 6190, (1972).

Preparation 4

Preparation of Alkynyl, Alkenyl and Alkyl Acetals of Formula (VII)

4.A. Alkynyl Acetals

4.A.1. Octynyl Acetals 31.25 ml of n-butyl-lithium in hexane was added over 10 minutes to a stirred solution of 9.9 g of 3-(t-butyldimethylsilyloxy)oct-1-yne in 30 ml of toluene at 0° C. under nitrogen. After 15 minutes a 25% solution of dimethylchloroalane in hexane (14.8 ml) was added over 0 minutes, followed, after stirring for one hour, by addition of 3.36 grams of 2,3-endo-epoxyspiro[bicyclo[3.2.0]-heptane-6,2'-[1,3]dioxolan] (VI) in 10 ml of toluene. The mixture was heated at 80° C. under constant stirring for 8 hours, then cooled to 0° C. and the reaction was quenched by addition of 100 ml of saturated aqueous sodium sulfate. The mixture was clarified by filtration and the layers separated. The aqueous layer was extracted with ether and combined organic layers washed with water, dried with magnesium sulfate and evaporated to yield 15.15 g of an oily mixture of regioisomeric hydroxysilyoxyacetals. The oil was dissolved in 100 ml of a mixture of 3:1:1 acetic acid-water-tetrahydrofuran and stirred at room temperature until TLC indicated the reaction was complete. The solution was neutralized with diluted NaOH, the bulk of the solvent was removed by evaporation, and the residue was extracted with ether. The dried extracts were evaporated to an oily mixture of 2 products in approximately 2:1 ratio, which was subsequently separated by short column silica-gel chromatography (elution with 3% ethanol-chloroform solvent). The major component (isomer A) was identified as 2-exo-(3-hydroxyoct-1-ynyl)spiro[bicyclo(3.2.0)heptane-6,2'-(1,3)dioxolan]-3-endo-ol (VIIA), while the minor product (isomer B) is the regioisomer resulting from alane attack at C-3, namely 3-exo-(3-hydroxyoct-1-ynyl)spiro-[bicyclo(3.2.0)heptane-6,2'-(1,3)dioxolan]-2-endo-ol (VIIB).

4.A.2. Other Alkynyl Acetals

Similarly, using the same procedure described in Preparation 4.A.1., other alkynyl acetals are prepared by substituting for 3-(t-butyldimethylsilyloxy)oct-1-yne the 3-silyloxy derivative of an appropriate 3-hydroxyalk-1-yne wherein said alk-1-yne has 4–15 carbon atoms.

In this manner, there are respectively obtained:

4.A.2.a.

2-exo(3-hydroxybut-1-ynyl)spiro[bicyclo(3.2.0)-heptane-6,2'-(1,3)dioxolan]-3-endo-ol;

2-exo(3-hydroxypent-1-ynyl)spiro[bicyclo(3.2.0)heptane-6,2'-(1,3)dioxolan]-3-endo-ol;

2-exo(3-hydroxyhex-1-ynyl)spiro[bicyclo(3.2.0)heptane-6,2'-(1,3)dioxolan]-3-endo-ol;

2-exo(3-hydroxyhept-1-ynyl)spiro[bicyclo(3.2.0)heptane-6,2'-(1,3)dioxolan]-3-endo-ol;

2-exo(3-hydroxynon-1-ynyl)spiro[bicyclo(3.2.0)heptane-6,2'-(1,3)dioxolan]-3-endo-ol;
2-exo(3-hydroxydec-1-ynyl)spiro[bicyclo(3.2.0)heptane-6,2'-(1,3)dioxolan]-3-endo-ol;
2-exo(3-hydroxyundec-1-ynyl)spiro[bicyclo(3.2.0)heptane-6,2'-(1,3)dioxolan]-3-endo-ol;
2-exo(3-hydroxydodec-1-ynyl)spiro[bicyclo(3.2.0)heptane-6,2'-(1,3)dioxolan]-3-endo-ol; or
2-exo(3-hydroxypentadec-1-ynyl)spiro[bicyclo(3.2.0)-heptane-6,2'-(1,3)dioxolan]-3-endo-ol; or 4.A.2.b.

3-exo(3-hydroxybut-1-ynyl)spiro[bicyclo(3.2.0)-heptane-6,2'-(1,3)dioxolan]-2-endo-ol;
3-exo(3-hydroxypent-1-ynyl)spiro[bicyclo(3.2.0)heptane-6,2'-(1,3)dioxolan]-2-endo-ol;
3-exo(3-hydroxyhex-1-ynyl)spiro[bicyclo(3.2.0)heptane-6,2'-(1,3)dioxolan]-2-endo-ol;
3-exo(3-hydroxyhept-1-ynyl)spiro[bicyclo(3.2.0)heptane-6,2'-(1,3)dioxolan]-2-endo-ol;
3-exo(3-hydroxynon-1-ynyl)spiro[bicyclo(3.2.0)heptane-6,2'-(1,3)dioxolan]-2-endo-ol;
3-exo(3-hydroxydec-1-ynyl)spiro[bicyclo(3.2.0)heptane-6,2'-(1,3)dioxolan]-2-endo-ol;
3-exo(3-hydroxyundec-1-ynyl)spiro[bicyclo(3.2.0)heptane-6,2'-(1,3)dioxolan]-2-endo-ol;
3-exo(3-hydroxydodec-1-ynyl)spiro[bicyclo(3.2.0)heptane-6,2'-(1,3)dioxolan]-2-endo-ol;
3-exo(3-hydroxypentadec-1-ynyl)spiro[bicyclo(3.2.0)-heptane-6,2'-(1,3)dioxolan]-2-endo-ol;

4.A.3. Alkynyl Acetals with Side Chains Containing Branched Alkyl, Cycloalkyl, Phenyl or Substituted Phenyl Groups.

In a similar manner, but substituting 3-(t-butyldimethylsilyloxy)alk-1-yne by
3-(t-butyldimethylsilyloxy)-6-ethyloct-1-yne,
3-(t-butyldimethylsilyloxy)-3-cyclopentylprop-1-yne,
3-(t-butyldimethylsilyloxy)-3-cyclohexylprop-1-yne,
3-(t-butyldimethylsilyloxy)-3-phenylprop-1-yne,
3-(t-butyldimethylsilyloxy)3-(4-chlorophenyl)prop-1-yne,
3-(t-butyldimethylsilyloxy)-3-(2,4-dimethylphenyl)-prop-1-ynyl,
3-(t-butyldimethylsilyloxy)-4-phenylbut-1-yne,
3-(t-butyldimethylsilyloxy)-4-(4-methoxyphenylbut)-1-yne, and
3-(t-butyldimethyl-silyloxy)-3-(3-trifluoromethylphenyl)prop-1-yne, the following representative compounds are prepared:

4.A.3.a.

2-exo(3-hydroxy-6-ethyloct-1-ynyl)spiro[bicyclo(3.2.0)-heptane-6,2'-(1,3)dioxolan]-3-endo-ol;
2-exo(3-hydroxy-3-cyclopentylprop-1-ynyl))spiro[bicyclo(3.2.0)-heptane-6,2'-(1,3)dioxolan]-3-endo-ol;
2-exo(3-hydroxy-3-cyclohexylprop-1-ynyl)spiro[bicyclo-(3.2.0)heptane-6,2'-(1,3)dioxolan]-3-endo-ol;
2-exo(3-hydroxy-3-phenylprop-1-ynyl)spiro[bicyclo-(3.2.0)heptane-6,2'-(1,3)dioxolan]-3-endo-ol;
2-exo(3-hydroxy-3-(4-chlorophenyl)prop-1-ynyl) spiro[bicyclo(3.2.0)heptane-6,2'-(1,3)dioxolan]-3-endo-ol;
2-exo(3-hydroxy-3-[2,4-dimethylphenyl]prop-1-ynyl)-spiro[bicyclo(3.2.0)heptane-6,2'-(1,3)dioxolan]-3-endo-ol;
2-exo(3-hydroxy-4-phenylbut-1-ynyl)spiro[bicyclo(3.2.0)heptane-6,2'-(1,3)dioxolan]-3-endo-ol;
2-exo(3-hydroxy-4-[4-methoxyphenyl]but-1-ynyl)-spiro[bicyclo(3.2.0)heptane-6,2'-(1,3)dioxolan]-3-endo-ol;
2-exo(3-hydroxy-3-[3-trifluoromethylphenyl]prop-1-ynyl)spiro[bicyclo(3.2.0)heptane-6,2'-(1,3)dioxolan]-3-endo-ol;

4.A.3.b.

3-exo-(3-hydroxy-6-ethyloct-1-ynyl)spiro[bicyclo(3.2.0)-heptane-6,2'-(1,3)dioxolan]-2-endo-ol;
3-exo-(3-hydroxy-3-cyclopentylprop-1-ynyl)spiro[bicyclo(3.2.0)-heptane-6,2'-(1,3)dioxolan]-2-endo-ol;
3-exo-(3-hydroxy-3-cyclohexylprop-1-ynyl)spiro[bicyclo-(3.2.0)heptane-6,2'-(1,3)dioxolan]-2-endo-ol;
3-exo-(3-hydroxy-3-phenylprop-1-ynyl)spiro[bicyclo-(3.2.0)heptane-6,2'-(1,3)dioxolan]-2-endo-ol;
3-exo-(3-hydroxy-3-(4-chlorophenyl)prop-1-ynyl)-spiro[bicyclo(3.2.0)heptane-6,2'-(1,3)dioxolan]-2-endo-ol;
3-exo-(3-hydroxy-3-[2,4-dimethylphenyl]prop-1-ynyl)-spiro[bicyclo(3.2.0)heptane-6,2'-(1,3)dioxolan]-2-endo-ol;
3-exo-(3-hydroxy-4-phenylbut-1-ynyl)spiro[bicyclo(3.2.0)-(1,3)dioxolan]-2-endo-ol;
3-exo-(3-hydroxy-4-[4-methoxyphenyl]but-1-ynyl)-spiro[bicyclo(3.2.0)heptane-6,2'-(1,3)dioxolan]-2-endo-ol;
3-exo-(3-hydroxy-3-[3-trifluoromethylphenyl]prop-1-ynyl)spiro[bicyclo(3.2.0)heptane-6,2'-(1,3) dioxolan]-2-endo-ol.

4.A.4. Octynyl Acetals Containing the t-Butyldimethylsilyloxy Protective Group Following the procedure of 4.A.1, there was obtained a mixture of regioisomeric hydroxysilyloxyacetals, which was not hydrolyzed with acetic acid-water-tetrahydrofuran as in 4.A.1. The mixture of hydroxysilyloxyacetals was separated using silica gel preparative column chromatography using a mixture of 97:3 dichloromethane-acetone. The major component was identified as
2-exo-(3-t-butyldimethylsilyloxyoct-1-ynyl)spiro[bicyclo(3.2.0)heptane-6,2'-(1,3)-dioxolan]-3-endo-ol,
while the minor component was identified as
3-exo-(3-t-butyldimethylsilyloxyoct-1-ynyl)spiro[bicyclo(3.2.0)heptane-6,2'-(1,3)-dioxolan]-2-endo-ol.

4.A.5. Other Alkynyl t-Butyldimethylsilyloxy Acetals

Similarly, using the same procedure described in 4.A.4., other alkynyl t-butyldimethylsilyloxy acetals are prepared by substituting for 3-(t-butyldimethylsilyloxy)oct-1-yne the 3-silyloxy derivative of an appropriate 3-hydroxyalk-1-yne wherein said alk-1-yne has 4-15 carbon atoms.

In this manner there are respectively obtained:

4.A.5.a.

2-exo-(3-t-butyldimethylsilyloxybut-1-ynyl)spiro[bicyclo(3.2.0)-heptane-6,2'-(1,3)dioxolan]-3-endo-ol;
2-exo-(3-t-butyldimethylsilyloxypent-1-ynyl)spiro[bicyclo(3.2.0)-heptane-6,2'-(1,3)dioxolan]-3-endo-ol;
2-exo-(3-t-butyldimethylsilyloxyhex-1-ynyl)spiro[bicyclo(3.2.0)-heptane-6,2'-(1,3)dioxolan]-3-endo-ol;
2-exo-(3-t-butyldimethylsilyloxyhept-1-ynyl)spiro[bicyclo(3.2.0)-heptane-6,2'-(1,3)dioxolan]-3-endo-ol;
2-exo-(3-t-butyldimethylsilyloxynon-1-ynyl)spiro[bicyclo(3.2.0)-heptane-6,2'-(1,3)dioxolan]-3-endo-ol;

2-exo-(3-t-butyldimethylsilyloxydec-1-ynyl)spiro[bicyclo(3.2.0)-heptane-6,2'-(1,3)dioxolan]-3-endo-ol;

2-exo-(3-t-butyldimethylsilyloxyundec-1-ynyl)spiro[bicyclo(3.2.0)heptane-6,2'-(1,3)dioxolan]-3-endo-ol;

2-exo-(3-t-butyldimethylsilyloxydodec-1-ynyl)spiro[bicyclo(3.2.0)heptane-6,2'-(1,3)dioxolan]-3-endo-ol; or 2-exo-(3-t-butyldimethylsilyloxypentadec-1-ynyl)-spiro[bicyclo(3.2.0)-heptane-6,2'-(1,3)dioxolan]-3-endo-ol; or

4.A.5.b.

3-exo-(3-t-butyldimethylsilyloxybut-1-ynyl)spiro[bicyclo(3.2.0)-heptane-6,2'-(1,3)dioxolan]-2-endo-ol;

3-exo-(3-t-butyldimethylsilyloxypent-1-ynyl)spiro[bicyclo(3.2.0)heptane-6,2'-(1,3)dioxolan]-2-endo-ol;

3-exo-(3-t-butyldimethylsilyloxyhex-1-ynyl)spiro[bicyclo(3.2.0)-heptane-6,2'-(1,3)dioxolan]-2-endo-ol;

3-exo-(3-t-butyldimethylsilyloxyhept-1-ynyl)spiro[bicyclo(3.2.0)heptane-6,2'-(1,3)dioxolan]-2-endo-ol;

3-exo-(3-t-butyldimethylsilyloxynon-1-ynyl)spiro[bicyclo(3.2.0)-heptane-6,2'-(1,3)dioxolan]-2-endo-ol;

3-exo-(3-t-butyldimethylsilyloxydec-1-ynyl)spiro[bicyclo(3.2.0)-heptane-6,2'-(1,3)dioxolan]-2-endo-ol;

3-exo-(3-t-butyldimethylsilyloxyundec-1-ynyl)spiro[bicyclo(3.2.0)heptane-6,2'-(1,3)dioxolan]-2-endo-ol;

3-exo-(3-t-butyldimethylsilyloxydodec-1-ynyl)spiro[bicyclo(3.2.0)heptane-6,2'-(1,3)dioxolan]-2-endo-ol;

3-exo-(3-t-butyldimethylsilyloxypentadec-1-ynyl)-spiro[bicyclo(3.2.0)-heptane-6,2'-(1,3)dioxolan]-2-endo-ol;

4.A.6. Alkynyl t-Butyldimethylsilyloxy Acetals with Side Chains Containing Branched Alkyl, Cycloalkyl, Phenyl or Substituted Phenyl Groups In a similar manner but substituting
3-(t-butyldimethylsilyloxy)alk-1-yne by
3-(t-butyldimethylsilyloxy)-6-ethyloct-1-yne,
3-(t-butyldimethylsilyloxy)-3-cyclopentylprop-1-yne,
3-(t-butyldimethylsilyloxy)-3-cyclohexylprop-1-yne,
3-(t-butyldimethylsilyloxy)-3-phenylprop-1-yne,
3-(t-butyldimethylsilyloxy)3-(4-chlorophenyl)prop-1-yne,
3-(t-butyldimethylsilyloxy)-3-(2,4-dimethylphenyl)-prop-1-ynyl,
3-(t-butyldimethylsilyloxy)-4-phenylbut-1-yne,
3-(t-butyldimethylsilyloxy)-4-(4-methoxyphenylbut)-1-yne, and
3-(t-butyldimethyl-silyloxy)-3-(3-trifluoromethylphenyl)prop-1-yne, the following representative compounds are prepared:

4.A.6.a.

2-exo-(3-t-butyldimethylsilyloxy-6-ethyloct-1-ynyl)-spiro[bicyclo(3.2.0)-heptane-6,2'-(1,3)dioxolan]-3-endo-ol;

2-exo-(3-t-butyldimethylsilyloxy-3-cyclopentylprop-1-ynyl)spiro[bicyclo(3.2.0)-heptane-6,2'-(1,3)dioxolan]-3-endo-ol;

2-exo-(3-t-butyldimethylsilyloxy-3-cyclohexylprop-1-ynyl)spiro[bicyclo(3.2.0)heptane-6,2'-(1,3)dioxolan]-3-endo-ol;

2-exo-(3-t-butyldimethylsilyloxy-3-phenylprop-1-ynyl)-spiro[bicyclo(3.2.0)heptane-6,2'-(1,3)dioxolan]-3-endo-ol;

2-exo-(3-t-butyldimethylsilyloxy-3-(4-chlorophenyl)-prop-1-ynyl)spiro[bicyclo(3.2.0)heptane-6,2'-(1,3)dioxolan]-3-endo-ol;

2-exo-(3-t-butyldimethylsilyloxy-3-[2,4-dimethylphenyl]prop-1-ynyl)spiro[bicyclo(3.2.0)heptane-6,2'-(1,3)dioxolan]-3-endo-ol;

2-exo-(3-t-butyldimethylsilyloxy-4-phenylbut-1-ynyl)-spiro[bicyclo(3.2.0)heptane-6,2'-(1,3)dioxolan]-3-endo-ol;

2-exo-(3-t-butyldimethylsilyloxy-4-[4-methoxyphenyl]but-1-ynyl)spiro[bicyclo(3.2.0)heptane-6,2'(1,3)dioxolan]-3-endo-ol;

2-exo-(3-t-butyldimethylsilyloxy-3-[3-trifluoromethylphenyl]prop-1-ynyl)spiro[bicyclo(3.2.0)heptane-6,2'-(1,3)dioxolan]-3-endo-ol;

4.A.6.b.

3-exo-(3-t-butyldimethylsilyloxy-6-ethyloct-1-ynyl)-spiro[bicyclo(3.2.0)-heptane-6,2'-(1,3)dioxolan]-2-endo-ol;

3-exo-(3-t-butyldimethylsilyloxy-3-cyclopentylprop-1-ynyl)spiro[bicyclo(3.2.0)-heptane-6,2'-(1,3)dioxolan]-2-endo-ol;

3-exo-(3-t-butyldimethylsilyloxy-3-cyclohexylprop-1-ynyl)spiro[bicyclo-(3.2.0)heptane-6,2'-(1,3)dioxolan]-2-endo-ol;

3-exo-(3-t-butyldimethylsilyloxy-3-phenylprop-1-ynyl)-spiro[bicyclo-(3.2.0)heptane-6,2'-(1,3)dioxolan]-2-endo-ol;

3-exo-(3-t-butyldimethylsilyloxy-3-(4-chlorophenyl)-prop-1-ynyl)spiro-[bicyclo(3.2.0)heptane-6,2'-(1,3)dioxolan]-2-endo-ol;

3-exo-(3-t-butyldimethylsilyloxy-3-[2,4-dimethylphenyl]prop-1-ynyl)spiro[bicyclo(3.2.0)heptane-6,2'-(1,3)dioxolan]-2-endo-ol;

3-exo-(3-t-butyldimethylsilyloxy-4-phenylbut-1-ynyl)-spiro[bicyclo(3.2.0)heptane-6,2'-(1,3)dioxolan]-2-endo-ol;

3-exo-(3-t-butyldimethylsilyloxy-4-[4-methoxyphenyl]-but-1-ynyl)-spiro[bicyclo(3.2.0)heptane-6,2'-(1,3)dioxolan]-2-endo-ol;

3-exo-(3-t-butyldimethylsilyloxy-3-[3-trifluoromethylphenyl]prop-1-ynyl)spiro[bicyclo(3.2.0)heptane-6,2'(1,3)dioxolan]-2-endo-ol.

4.A.7. Octynyl Acetals via Intermediates in 4.A.4

To a stirred solution of 225 mg of 2-exo-(3-t-butyldimethylsilyloxyoct-1-ynyl)spiro[bicyclo(3.2.0)heptane-6,2'-(1,3)dioxolan]-3-endo-ol in 2.5 ml tetrahydrofuran was added 2.2 ml of a 1 M solution of tetrabutylammonium fluoride in tetrahydrofuran. After 5 hours the solvent was evaporated, water was added and the product was extracted into ethyl acetate. Evaporation gave a residue, which was purified by silica gel column chromatography with ethyl acetate-hexane 7:3 to give 2-exo-(3-hydroyoct-1-ynyl)spiro[bicyclo(3.2.0-)heptane-6,2'-(1,3)dioxolan]-3-endo-ol. Similarly, 3-exo-(3-hydroyoct-1-ynyl)spiro[bicyclo(3.2.0)heptane-6,2'-(1,3)dioxolan]-2-endo-ol was prepared starting with 3-exo-(3-t-butyldimethylsilyloxyoct-1-ynyl)spiro[bicyclo(3.2.0)heptane-6,2'-(1,3)dioxolan]-2-endo-ol.

4.A.8. Alkynyl Acetals via Intermediates in 4.A.5

Similarly, using the procedure in 4.A.7 the list of alkynyl acetals in 4.A.2 was prepared.

4.A.9. Alkynyl Acetals with Side Chains Containing Branched Alkyl, Cycloalkyl, Phenyl or Substituted Phenyl Groups via Intermediates in 4.A.6

Similarly, using the procedure in 4.A.7 the list of alkynyl acetals in 4.A.3. was prepared.

4.B. Alkenyl Acetals

4.B.1. Octenyl acetals

An equivalent of 1.35 M n-butyl-lithium in hexane is added to a stirred solution of 48.2 g of 3-(t-butyldimethylsilyloxy)-trans-1-iodo-oct-1-ene in anhydrous diethyl ether at −78° C. under nitrogen. After one hour a solution of 17.2 g of pent-1-ynylcopper and 45 ml of hexamethylphosphorotriamide in ether is added. The mixture is stirred for 2 hours at −78° C. Then, 20 g of epoxyacetal (VI) in 100 ml of ether is added dropwise over one hour. The reaction mixture is further stirred for another 3 hours at −78° C. and then it is left for 16 hours in a freezer at −20° C. After that saturated aqueous ammonium chloride is added and the mixture is further stirred for one hour at room temperature. The layers are separated and the organic layers are washed with 200 ml of cold 2N hydrochloric acid, 200 ml of water, dried with magnesium sulfate and evaporated. The evaporated residue is purified by short-column chromatography on silica gel with dichloromethane as eluant. By this procedure two isomers are obtained. The major isomer is:

2-exo(3-hydroxyoct-1-trans-enyl)spiro[bicyclo(3.2.0-)heptan-6,2'-(1,3)-dioxolan]-3-endo-ol.

The minor isomer is:

3-exo(3-hydroxyoct-1-trans-enyl)spiro[bicyclo(3.2.0.-)heptan-6,2'-(1,3)dioxolan]-2-endo-ol.

4.B.2. Other Alkenyl Acetals

Similarly, using the same procedure described in Preparation 4.B.1. other alkenyl acetals are prepared by substituting 3-(t-butyldimethylsilyloxy)trans-1-iodooct-1-ene by the appropriate 3-(t-butyldimethylsilyloxy)-1-iodoalk-1-ene wherein the parent 1-alken-3-ol contains 4-15 carbon atoms. (Preparation 3.C.)

In this manner, there are respectively obtained

4.B.2.a.

2-exo(3-hydroxybut-1-trans-enyl)spiro[bicyclo(3.2.0)-heptane-6,2'-(1,3)dioxolan]-3-endo-ol;
2-exo(3-hydroxypent-1-trans-enyl)spiro[bicyclo(3.2.0)-heptane-6,2'-(1,3)dioxolan]-3-endo-ol;
2-exo(3-hydroxyhex-1-trans-enyl)spiro[bicyclo(3.2.0)-heptane-6,2'-(1,3)dioxolan]-3-endo-ol;
2-exo(3-hydroxyhept-1-trans-enyl)spiro[bicyclo(3.2.0)-heptane-6,2'-(1,3)dioxolan]-3-endo-ol;
2-exo(3-hydroxynon-1-trans-enyl)spiro-[bicyclo(3.2.0)-heptane-6,2'-(1,3)dioxolan]-3-endo-ol;
2-exo(3-hydroxydec-1-trans-enyl)spiro-[bicyclo(3.2.0)-heptane-6,2'-(1,3)dioxolan]-3-endo-ol;
2-exo(3-hydroxyundec-1-trans-enyl)spiro[bicyclo(3.2.0)-heptane-6,2'-(1,3)dioxolan]-3-endo-ol;
2-exo(3-hydroxydodec-1-trans-enyl)spiro[bicyclo(3.2.0)-heptane-6,2'-(1,3)dioxolan]-3-endo-ol; or
2-exo(3-hydroxypentadec-1-trans-enyl)spiro[bicyclo(3.2.0)-heptane-6,2'-(1,3)dioxolan]-3-endo-ol;

4.B.2.b.

3-exo(3-hydroxybut-1-trans-enyl)spiro[bicyclo(3.2.0)-heptane-6,2'-(1,3)dioxolan]-2-endo-ol;
3-exo(3-hydroxypent-1-trans-enyl)spiro[bicyclo(3.2.0)-heptane-6,2'-(1,3)dioxolan]-2-endo-ol;
3-exo(3-hydroxyhex-1-trans-enyl)spiro[bicyclo(3.2.0)-heptane-6,2'-(1,3)dioxolan]-2-endo-ol;
3-exo(3-hydroxyhept-1-trans-enyl)spiro[bicyclo(3.2.0)-heptane-6,2'-(1,3)dioxolan]-2-endo-ol;
3-exo(3-hydroxynon-1-trans-enyl)spiro[bicyclo(3.2.0)-heptane-6,2'-(1,3)dioxolan]-2-endo-ol;
3-exo(3-hydroxydec-1-trans-enyl)spiro[bicyclo(3.2.0)-heptane-6,2'-(1,3)dioxolan]-2-endo-ol;
3-exo(3-hydroxyundec-1-trans-enyl)spiro[bicyclo(3.2.0)-heptane-6,2'-(1,3)dioxolan]-2-endo-ol;
3-exo(3-hydroxydodec-1-trans-enyl)spiro[bicyclo(3.2.0)-heptane-6,2'-(1,3)dioxolan]-2-endo-ol;
3-exo(3-hydroxypentadec-1-trans-enyl)spiro[bicyclo(3.2.0)-heptane-6,2'-(1,3)dioxolan]-2-endo-ol.

4.B.3. Alkynyl Acetals with Side Chains Containing Branched Alkyl, Cycloalkyl, Phenyl or Substituted Phenyl Groups Similarly, using the same procedure described in Preparation 4.B.1., other alkenyl acetals are prepared by substituting 3-(t-butyldimethylsilyloxy)-1-iodo[oct-1-trans-ene by the appropriate 3-(t-butyldimethylsilyloxy)-1-iodoalk-1-trans-ene such as 3-(t-butyldimethylsilyloxy)-1-iodo-6-ethyloct-1-trans-ene,
3-(t-butyldimethylsilyloxy)-1-iodo-3-cyclopentyl-prop-1-trans-ene,
3-(t-butyldimethylsilyloxy)-1-iodo-3-cyclohexyl-prop-1-trans-ene,
3-(t-butyldimethylsilyloxy)-1-iodo-3-phenylprop-1-trans-ene,
3-(t-butyldimethylsilyloxy)-1-iodo-3-(4-chlorophenyl)-prop-1-trans-ene,
3-(t-butyldimethylsilyloxy)-1-iodo-3-(2,4-dimethylphenyl)prop-1-trans-ene,
3-(t-butyldimethylsilyloxy)-1-iodo-4-phenylbut-1-trans-ene,
3-(t-butyldimethylsilyloxy)-1-iodo-4-(4-methoxyphenyl)but-1-trans-ene, and
3-(t-butyldimethylsilyloxy)-1-iodo-3-(3-trifluoromethylphenyl)prop-1-trans-ene, the following representative compounds are prepared:

4.B.3.a.

2-exo(3-hydroxy-6-ethyloct-1-trans-enyl)spiro[bicyclo(3.2.0)-heptane-6,2'-(1,3)dioxolan]-3-endo-ol;
2-exo(3-hydroxy-3-cyclopentylprop-1-trans-enyl)-spiro[bicyclo(3.2.0)-heptane-6,2'-(1,3)dioxolan]-3-endo-ol;
2-exo(3-hydroxy-3-cyclohexylprop-1-trans-enyl)spiro[bicyclo(3.2.0)heptane-6,2'-(1,3)dioxolan]-3-endo-ol;
2-exo(3-hydroxy-3-phenylprop-1-trans-enyl)spiro[bicyclo(3.2.0)heptane-6,2'-(1,3)dioxolan]-3-endo-ol;
2-exo(3-hydroxy-3-(4-chlorophenyl)prop-1-trans-enyl)-spiro[bicyclo(3.2.0)heptane-6,2'-(1,3)dioxolan]-3-endo-ol;
2-exo(3-hydroxy-3-[2,4-dimethylphenyl]prop-1-trans-enyl)spiro[bicyclo(3.2.0)heptane-6,2'-(1,3)dioxolan]-3-endo-ol;
2-exo(3-hydroxy-4-phenylbut-1-trans-enyl)spiro[bicyclo(3.2.0)heptane-6,2'-(1,3)dioxolan]-3-endo-ol;
2-exo(3-hydroxy-4-[4-methoxyphenylbut-1-trans-enyl)-spiro-[bicyclo(3.2.0)heptane-6,2'-(1,3)dioxolan]-3-endo-ol;
2-exo(3-hydroxy-3-[3-trifluoromethylphenyl]prop-1-trans-enyl)spiro-[bicyclo(3.2.0)heptane-6,2'-(1,3)dioxolan]-3-endo-ol;

4.B.3.b.

3-exo(3-hydroxy-6-ethyloct-1-trans-enyl)spiro[bicyclo(3.2.0)-heptane-6,2'-(1,3)dioxolan]-2-endo-ol;

3-exo(3-hydroxy-3-cyclopentylprop-1-trans-enyl)-
spiro[bicyclo(3.2.0)-heptane-6,2'-(1,3)dioxolan]-2-
endo-ol;

3-exo(3-hydroxy-3-cyclohexylprop-1-trans-enyl)spiro[-
bicyclo(3.2.0)heptane-6,2'-(1,3)dioxolan]-2-endo-ol;

3-exo(3-hydroxy-3-phenylprop-1-trans-enyl)spiro[bicy-
clo(3.2.0)heptane-6,2'-(1,3)dioxolan]-2-endo-ol;

3-exo(3-hydroxy-3-(4-chlorophenyl)prop-1-trans-enyl)-
spiro[bicyclo(3.2.0)heptane-6,2'-(1,3)dioxolan]-2-
endo-ol;

3-exo(3-hydroxy-3-[2,4-dimethylphenyl]prop-1-trans-
enyl)-spiro[bicyclo(3.2.0)heptane-6,2'-(1,3)dioxolan]-
2-endo-ol;

3-exo(3-hydroxy-4-phenylbut-1-trans-enyl)spiro[bicy-
clo(3.2.0)heptane-6,2'-(1,3)dioxolan]-2-endo-ol;

3-exo(3-hydroxy-4-[4-methoxyphenylbut-1-trans-enyl)-
spiro[bicyclo(3.2.0)heptane-6,2'-(1,3)dioxolan]-2-
endo-ol;

3-exo(3-hydroxy-3-[3-trifluoromethylphenyl]prop-1-
trans-enyl)spiro[bicyclo(3.2.0)heptane-6,2'-(1,3)diox-
olan]-2-endo-ol.

4.B.4. Octenyl Acetals as Individual Diastereoisomers in the 2-endo-ol Series A mixture of 128 mg of 3-exo-(3-hydroyoct-1-ynyl)-spiro[bicyclo(3.2.0)heptane-6,2'-(1,3)dioxolan-2-endo-ol from 4.A.1, in 3 ml tetrahydrofuran was added to a stirred mixture of 104 mg lithium aluminum hydride in 3 ml tetrahydrofuran under argon. The mixture was heated at reflux for 24 hours. After cooling 0.5 ml of a 2N sodium hydroxide solution was added slowly. The precipitate was removed by filtration and was washed with 25 ml ethyl acetate. The combined filtrate was washed with saturated sodium chloride solution. Evaporation of solvent gave a two-component mixture that was separated by silica-gel column chromatography using 70% ethyl acetate-hexane. The first eluted was 3-exo-(3β-hydroxyoct-1-trans-enyl)spiro[bicyclo(3.2.0.-)heptane-6,2'-(1,3)dioxolan]-2-endo-ol (Rf=0.34), and the second eluted was 3-exo-(3α-hydroxyoct-1-trans-enyl)spiro[bicyclo(3.2.0.-)heptane-6,2'-(1,3)dioxolan]-2-endo-ol (Rf=0.25).

4.B.5. Other Alkenyl Acetals as Individual Diastereoisomers in the 2-endo-ol Series Similarly, using the same procedure described in 4.B.4, other individual diastereoisomeric alkenyl acetals in the 2-endo-ol series are prepared by substituting the appropriate 3-exo-(3-hydroxyalk-1-ynyl)spiro[bicyclo(3.2.0)heptane-6,2'-(1,3)-dioxolan]-2-endo-ol described in Preparation 4.A.2.b. wherein the parent 3-exo-(3-hydroxyalk-1-ynyl) side chain contains 4–15 carbon atoms.

In this manner, there are respectively obtained:

4.B.5.a.

3-exo(3β-hydroxybut-1-trans-enyl)spiro[bicyclo(3.2.0)-heptane-6,2'-(1,3)dioxolan]-2-endo-ol;

3-exo(3β-hydroxypent-1-trans-enyl)spiro[bicy-clo(3.2.0)-heptane-6,2'-(1,3)dioxolan]-2-endo-ol;

3-exo(3β-hydroxyhex-1-trans-enyl)spiro[bicyclo(3.2.0)-heptane-6,2'-(1,3)dioxolan]-2-endo-ol;

3-exo(3β-hydroxyhept-1-trans-enyl)spiro[bicy-clo(3.2.0)-heptane-6,2'-(1,3)dioxolan]-2-endo-ol;

3-exo(3β-hydroxynon-1-trans-enyl)spiro[bicyclo(3.2.0)-heptane-6,2'-(1,3)dioxolan]-2-endo-ol;

3-exo(3β-hydroxydec-1-trans-enyl)spiro[bicyclo(3.2.0)-heptane-6,2'-(1,3)dioxolan]-2-endo-ol;

3-exo(3β-hydroxyundec-1-trans-enyl)spiro[bicy-clo(3.2.0)-heptane-6,2'-(1,3)dioxolan]-2-endo-ol;

3-exo(3β-hydroxydodec-1-trans-enyl)spiro[bicy-clo(3.2.0)-heptane-6,2'-(1,3)dioxolan]-2-endo-ol; or 3-exo(3β-hydroxypentadec-1-trans-enyl)spiro[bicyclo(3.2.0)-heptane-6,2'-(1,3)dioxolan]-2-endo-ol;

4.B.5.b.

3-exo(3α-hydroxybut-1-trans-enyl)spiro[bicyclo(3.2.0)-heptane-6,2'-(1,3)dioxolan]-2-endo-ol;

3-exo(3α-hydroxypent-1-trans-enyl)spiro[bicy-clo(3.2.0)-heptane-6,2'-(1,3)dioxolan]-2-endo-ol;

3-exo(3α-hydroxyhex-1-trans-enyl)spiro[bicyclo(3.2.0)-heptane-6,2'-(1,3)dioxolan]-2-endo-ol;

3-exo(3α-hydroxyhept-1-trans-enyl)spiro[bicy-clo(3.2.0)-heptane-6,2'-(1,3)dioxolan]-2-endo-ol;

3-exo(3α-hydroxynon-1-trans-enyl)spiro[bicyclo(3.2.0)-heptane-6,2'-(1,3)dioxolan]-2-endo-ol;

3-exo(3α-hydroxydec-1-trans-enyl)spiro[bicyclo(3.2.0)-heptane-6,2'-(1,3)dioxolan]-2-endo-ol;

3-exo(3α-hydroxyundec-1-trans-enyl)spiro[bicy-clo(3.2.0)-heptane-6,2'-(1,3)dioxolan]-2-endo-ol;

3-exo(3α-hydroxydodec-1-trans-enyl)spiro[bicyclo(3.2.0)-heptane-6,2'-(1,3)dioxolan]-2-endo-ol;

3-exo(3α-hydroxypentadec-1-trans-enyl)spiro[bicy-clo(3.2.0)-heptane-6,2'-(1,3)dioxolan]-2-endo-ol.

4.B.6. Individual Diasteoisomers of the 2-endo-ol Alkenyl Acetals with Side Chains Containing Branched Alkyl, Cycloalkyl, Phenyl or Substituted Phenyl Groups Similarly, using the same procedure described in 4.B.4, other alkenyl acetals are prepared by substituting the appropriate 3-exo-(3-hydroxyalk-1-ynyl)spiro[bicyclo(3.2.0)heptane-6,2'-(1,3)dioxolan]-2-endo-ol described in Preparation 4.A.3.b.

In this manner, there are respectively obtained:

4.B.6.a.

3-exo(3β-hydroxy-6-ethyloct-1-trans-enyl)spiro[bicy-clo(3.2.0)-heptane-6,2'-(1,3)dioxolan]-2-endo-ol;

3-exo(3β-hydroxy-3-cyclopentylprop-1-trans-enyl)-spiro[bicyclo(3.2.0)-heptane-6,2'-(1,3)dioxolan]-2-endo-ol;

3-exo(3β-hydroxy-3-phenylprop-1-trans-enyl)spiro[-bicyclo(3.2.0)heptane-6,2'-(1,3)dioxolan]-2-endo-ol;

3-exo(3β-hydroxy-3-(4-chlorophenyl)prop-1-trans-enyl)spiro[bicyclo(3.2.0)heptane-6,2'-(1,3)dioxolan]-2-endo-ol;

3-exo(3β-hydroxy-3-[2,4-dimethylphenyl]prop-1-trans-enyl)spiro[bicyclo(3.2.0)heptane-6,2'-(1,3)dioxolan]-2-endo-ol;

3-exo(3β-hydroxy-4-phenylbut-1-trans-enyl)spiro[bicy-clo(3.2.0)heptane-6,2'-(1,3)dioxolan]-2-endo-ol;

3-exo(3β-hydroxy-4-[4-methoxyphenylbut-1-trans-enyl)spiro[bicyclo(3.2.0)heptane-6,2'-(1,3)dioxolan]-2-endo-ol;

3-exo(3β-hydroxy-3-[3-trifluoromethylphenyl]prop-1-trans-enyl)spiro[bicyclo(3.2.0)heptane-6,2'-(1,3)dioxolan]-2-endo-ol;

4.B.6.b.

3-exo(3α-hydroxy-6-ethyloct-1-trans-enyl)spiro[bicy-clo(3.2.0)-heptane-6,2'-(1,3)dioxolan]-2-endo-ol;

3-exo(3α-hydroxy-3-cyclopentylprop-1-trans-enyl)-spiro[bicyclo(3.2.0)-heptane-6,2'-(1,3)dioxolan]-2-endo-ol;

3-exo(3α-hydroxy-3-cyclohexylprop-1-trans-enyl)-spiro[bicyclo(3.2.0)heptane-6,2'-(1,3)dioxolan]-2-endo-ol;

3-exo(3α-hydroxy-3-phenylprop-1-trans-enyl)spiro-[bicyclo(3.2.0)heptane-6,2'-(1,3)dioxolan]-2-endo-ol;

3-exo(3α-hydroxy-3-(4-chlorophenyl)prop-1-trans-enyl)spiro[bicyclo(3.2.0)heptane-6,2'-(1,3)dioxolan]-2-endo-ol;

3-exo(3α-hydroxy-3-[2,4-dimethylphenyl]prop-1-trans-enyl)-spiro[bicyclo(3.2.0)heptane-6,2'-(1,3)dioxolan]-2-endo-ol;

3-exo(3α-hydroxy-4-phenylbut-1-trans-enyl)spiro[bicyclo(3.2.0)heptane-6,2'-(1,3)dioxolan]-2-endo-ol;

3-exo(3α-hydroxy-4-[4-methoxyphenylbut-1-trans-enyl)spiro[bicyclo(3.2.0)heptane-6,2'-(1,3)dioxolan]-2-endo-ol;

3-exo(3α-hydroxy-3-[3-trifluoromethylphenyl]prop-1-trans-enyl)spiro[bicyclo(3.2.0)heptane-6,2'-(1,3)dioxolan]-2-endo-ol.

4.C. Alkyl Acetals

4.C.1. Octyl Acetals

A solution of 1.0 g of 2-exo-(3-hydroxy-oct-1-ynyl) spiro[bicyclo(3.2.0)heptane-6,2'-(1,3)-dioxolan]-3-endo-ol (VIIA) in 40 ml ethanol is vigorously stirred in the presence of platinum (from 100 mg of platinum oxide) under hydrogen at 1 atmosphere until 2 equivalent of the gas has been absorbed. The catalyst is removed by filtration. Evaporation of the filtrate under vacuum gives 2-exo-(3-hydroxyoct-1-yl)spiro[(bicyclo(3.2.0)heptane-6,2'-(1,3)dioxolan]-3-endo-ol.

Similarly, starting with regioisomer (VIIB) 3-exo-(3-hydroxyoct-1-yl)spiro[bicyclo(3.2.0)heptane-6,2'-(1,3)dioxolan]-2-endo-ol is prepared.

4.C.2. Other Alkyl Acetals

Similarly, by hydrogenating the compounds of Preparation 4.A.2 according to the procedure of Preparation 4.C.1 the following compounds are respectively obtained:

4.C.2.a.

2-exo(3-hydroxybut-1-yl)spiro[bicyclo(3.2.0)heptane-6,2'-(1,3)dioxolan]-3-endo-ol;

2-exo(3-hydroxypent-1-yl)spiro[bicyclo(3.2.0)heptane-6,2'-(1,3)dioxolan]-3-endo-ol;

2-exo(3-hydroxyhex-1-yl)spiro[bicyclo(3.2.0)heptane-6,2'-(1,3)dioxolan]-3-endo-ol;

2-exo(3-hydroxyhept-1-yl)spiro[bicyclo(3.2.0)heptane-6,2'-(1,3)dioxolan]-3-endo-ol;

2-exo(3-hydroxynon-1-yl)spiro[bicyclo(3.2.0)heptane-6,2'-(1,3)dioxolan]-3-endo-ol;

2-exo(3-hydroxydec-1-yl)spiro[bicyclo(3.2.0)heptane-6,2'-(1,3)dioxolan]-3-endo-ol;

2-exo(3-hydroxyundec-1-yl)spiro[bicyclo(3.2.0)-heptane-6,2'-(1,3)dioxolan]-3-endo-ol;

2-exo(3-hydroxydodec-1-yl)spiro[bicyclo(3.2.0)-heptane-6,2'-(1,3)dioxolan]-3-endo-ol;

2-exo(3-hydroxypentadec-1-yl)spiro[bicyclo (3 2.0)-heptane-6,2'-(1,3)dioxolan]-3-endo-ol;

4.C.2.b.

3-exo(3-hydroxybut-1-yl)spiro[bicyclo(3.2.0)heptane-6,2'-(1,3)dioxolan]-2-endo-ol;

3-exo(3-hydroxypent-1-yl)spiro[bicyclo(3.2.0)heptane-6,2'-(1,3)dioxolan]-2-endo-ol;

3-exo(3-hydroxyhex-1-yl)spiro[bicyclo(3.2.0)heptane-6,2'-(1,3)dioxolan]-2-endo-ol;

3-exo(3-hydroxyhept-1-yl)spiro[bicyclo(3.2.0)heptane-6,2'-(1,3)dioxolan]-2-endo-ol;

3-exo(3-hydroxynon-1-yl)spiro[bicyclo(3.2.0)heptane-6,2'-(1,3)dioxolan]-2-endo-ol;

3-exo(3-hydroxydec-1-yl)spiro[bicyclo(3.2.0)heptane-6,2'-(1,3)dioxolan]-2-endo-ol;

3-exo(3-hydroxyundec-1-yl)spiro[bicyclo(3.2.0)heptane-6,2'-(1,3)dioxolan]-2-endo-ol;

3-exo(3-hydroxydodec-1-yl)spiro[bicyclo(3.2.0)heptane-6,2'-(1,3)dioxolan]-2-endo-ol;

3-exo(3-hydroxypentadec-1-yl)spiro[bicyclo(3.2.0)-heptane-6,2'-(1,3)dioxolan]-2-endo-ol.

4.C.3. Alkyl Acetals with Side Chains Containing Branched Alkyl, Cycloalkyl, Phenyl or Substituted Phenyl Groups In similar manner following Procedure 4.C.1. but substituting the alkynyl acetals prepared by Procedure 4.A.3. for the octynyl acetal starting material of the former Procedure, the following representative compounds are prepared:

4.C.3.a.

2-exo(3-hydroxy-6-ethyloct-1-yl)spiro[bicyclo(3.2.0)heptane-6,2'-(1,3)dioxolan]-3-endo-ol;

2-exo(3-hydroxy-3-cyclopentylprop-1-yl)spiro[bicyclo(3.2.0)heptane-6,2'-(1,3)dioxolan]-3-endo-ol;

2-exo(3-hydroxy-3-cyclohexylprop-1-yl)spiro[bicyclo(3.2.0)heptane-6,2'-(1,3)dioxolan]-3-endo-ol;

2-exo(3-hydroxy-3-phenylprop-1-yl)spiro[bicyclo(3.2.0)heptane-6,2'-(1,3)dioxolan]-3-endo-ol;

2-exo(3-hydroxy-3-(4-chlorophenyl)prop-1-yl)-spiro-[bicyclo (3.2.0)heptane-6,2'-(1,3)dioxolan]-3-endo-ol;

2-exo(3-hydroxy-3-[2,4-dimethylphenyl]prop-1-yl)spiro-[bicyclo(3.2.0)heptane-6,2'-(1,3)dioxolan]-3-endo-ol;

2-exo(3-hydroxy-3-(4-butoxyphenyl)prop-1-yl)-spiro-[bicyclo (3.2.0)heptane-6,2'-(1,3)dioxolan]-3-endo-ol;

2-exo(3-hydroxy-3-[4-hydroxyphenyl]prop-1-yl)-spiro-[bicyclo (3.2.0)heptane-6,2'-(1,3)dioxolan]-3-endo-ol;

2-exo(3-hydroxy-3-[3-trifluoromethylphenyl]prop-1-yl)-spiro-[bicyclo (3.2.0)heptane-6,2'-(1,3)dioxolan]-3-endo-ol;

4.C.3.b.

3-exo(3-hydroxy-6-ethyloct-1-yl)spiro[bicyclo(3.2.0)heptane-6,2'-(1,3)dioxolan]-2-endo-ol;

3-exo(3-hydroxy-3-cyclopentylprop-1-yl)spiro[bicyclo(3.2.0)heptane-6,2'-(1,3)dioxolan]-2-endo-ol;

3-exo(3-hydroxy-3-cyclohexylprop-1-yl)spiro[bicyclo(3.2.0)heptane-6,2'-(1,3)dioxolan]-2-endo-ol;

3-exo(3-hydroxy-3-phenylprop-1-yl)spiro[bicyclo(3.2.0)heptane-6,2'-(1,3)dioxolan]-2-endo-ol;

3-exo(3-hydroxy-3-(4-chlorophenyl)prop-1-yl)spiro-[bicyclo(3.2.0)heptane-6,2'-(1,3)dioxolan]-2-endo-ol;

3-exo(3-hydroxy-3-[2,4-dimethylphenyl]prop-1-yl)spiro-[bicyclo(3.2.0)heptane-6,2'-(1,3)dioxolan]-2-endo-ol;

3-exo(3-hydroxy-4-phenylbut-1-yl)spiro-[bicyclo(3.2.0)heptane-6,2'-(1,3)dioxolan]-2-endo-ol;

3-exo(3-hydroxy-4-[4-methoxyphenyl]but-lyl)spiro-[bicyclo(3.2.0)heptane-6,2'-(1,3)dioxolan]-2-endo-ol;

3-exo(3-hydroxy-3-[3-trifluoromethylphenyl]prop-1-yl)-spiro-[bicyclo(3.2.0)heptane-6,2'-(1,3)dioxolan]-2-endo-ol.

4.C.4. Octyl t-Butyldimethylsilyloxy Acetals

A solution of 0.5 g of 2-exo-(3-t-butyldimethylsilyloxyoct-1-ynyl)spiro[bicyclo(3.2.0)heptane-6,2'-(1,3)dioxolan]-3-endo-ol in 40 ml ethanol is vigorously stirred in the presence of platinum (from 50 mg of platinum oxide) under hydrogen at 1 atmosphere until 2 equivalents of gas has been absorbed. The catalyst is removed by filtration. Evaporation of the filtrate under vacuum gives 2-exo-(3-t-butyldimethylsilyloxyoct-1-yl)spiro[bicyclo(3.2.0)heptane-6,2'-(1,3)dioxolan]-3-endo-ol.

Similarly, starting with 3-exo-(3-t-butyldimethylsilyloxyoct-1-ynyl)spiro[bicyclo(3.2.0)heptane-6,2'-(1,3)dioxolan]-2-endo-ol there is obtained 3-exo-(3-t-butyldimethylsilyloxyoct-1-yl)spiro[bicyclo(3.2.0)heptane-6,2'-(1,3)dioxolan]-2-endo-ol.

4.C.5. Other Alkyl t-Butyldimethylsilyloxy Acetals

Similarly, by hydrogenating compounds of Preparation 4.A.5 the following compounds are respectively obtained:

4.C.5.a.

2-exo(3-t-butyldimethylsilyloxybut-1-yl)spiro[bicyclo(3.2.0)heptane-6,2'-(1,3)dioxolan]-3-endo-ol;
2-exo(3-t-butyldimethylsilyloxypent-1-yl)spiro[bicyclo(3.2.0)heptane-6,2'-(1,3)dioxolan]-3-endo-ol;
2-exo(3-t-butyldimethylsilyloxyhex-1-yl)spiro[bicyclo(3.2.0)heptane-6,2'-(1,3)dioxolan]-3-endo-ol;
2-exo(3-t-butyldimethylsilyloxyhept-1-yl)spiro[bicyclo(3.2.0)heptane-6,2'-(1,3)dioxolan]-3-endo-ol;
2-exo(3-t-butyldimethylsilyloxynon-1-yl)-spiro[bicyclo(3.2.0)heptane-6,2'-(1,3)dioxolan]-3-endo-ol;
2-exo(3-t-butyldimethylsilyloxydec-1-yl)-spiro[bicyclo(3.2.0)heptane-6,2'-(1,3)dioxolan]-3-endo-ol;
2-exo(3-t-butyldimethylsilyloxyundec-1-yl)spiro[bicyclo(3.2.0)-heptane-6,2'-(1,3)dioxolan]-3endo-ol;
2-exo(3-t-butyldimethylsilyloxydodec-1-yl)spiro-[bicyclo (3.2.0)-heptane-6,2'-(1,3)dioxolan]-3-endo-ol;
2-exo(3-t-butyldimethylsilyloxypentadec-1-yl)spiro-[bicyclo(3.2.0)-heptane-6,2'-(1,3)dioxolan]-3-endo-ol;

4.C.5.b.

3-exo(3-t-butyldimethylsilyloxydroxybut-1-yl)spiro-[bicyclo(3.2.0)heptane-6,2'-(1,3)dioxolan]-2-endo-ol;
3-exo(3-t-butyldimethylsilyloxypent-1-yl)spiro[bicyclo(3.2.0)heptane-6,2'-(1,3)dioxolan]-2-endo-ol;
3-exo(3-t-butyldimethylsilyloxyhex-1-yl)spiro[bicyclo(3.2.0)heptane-6,2'-(1,3)dioxolan]-2-endo-ol;
3-exo(3-t-butyldimethylsilyloxyhept-1-yl)spiro[bicyclo(3.2.0)heptane-6,2'-(1,3)dioxolan]-2-endo-ol;
3-exo(3-t-butyldimethylsilyloxynon-1-yl)spiro[bicyclo(3.2.0)heptane-6,2'-(1,3)dioxolan]-2-endo-ol;
3-exo(3-t-butyldimethylsilyloxydec-1-yl)spiro[bicyclo(3.2.0)heptane-6,2'-(1,3)dioxolan]-2-endo-ol;
3-exo(3-t-butyldimethylsilyloxyundec-1-yl)spiro[bicyclo(3.2.0)-heptane-6,2'-(1,3)dioxolan]-2-endo-ol;
3-exo(3-t-butyldimethylsilyloxydodec-1-yl)spiro[bicyclo(3.2.0)-heptane-6,2'-(1,3)dioxolan]-2-endo-ol;
3-exo(3-t-butyldimethylsilyloxypentadec-1-yl)spiro-[bicyclo(3.2.0)-heptane-6,2'-(1,3)dioxolan]-2-endo-ol.

4.C.6. Alkyl t-Butyldimethylsilyloxy Acetals with Side Chains Containing Branched Alkyl, Cycloalkyl, Phenyl or Substituted Phenyl Groups Similarly, by hydrogenating compounds in Preparation 4.A.6., the following representative compounds are prepared:

4.C.6.a.

2-exo(3-t-butyldimethylsilyloxy-6-ethyloct-1-yl)spiro[-bicyclo(3.2.0)heptane-6,2'-(1,3)dioxolan]-3-endo-ol;
2-exo(3-t-butyldimethylsilyloxy-3-cyclopentylprop-1-yl)spiro[bicyclo(3.2.0)heptane-6,2'-(1,3)dioxolan]-3-endo-ol;
2-exo(3-t-butyldimethylsilyloxy-3-cyclohexylprop-1-yl)spiro[bicyclo(3.2.0)heptane-6,2'-(1,3)dioxolan]-3-endo-ol;
2-exo(3-t-butyldimethylsilyloxy-3-phenylprop-1-yl)spiro[bicyclo(3.2.0)heptane-6,2'-(1,3)dioxolan]-3-endo-ol;
2-exo(3-t-butyldimethylsilyloxy-3-(4-chlorophenyl)-prop-1-yl)spiro[bicyclo(3.2.0)heptane-6,2'-(1,3)dioxolan]-3-endo-ol;
2-exo(3-t-butyldimethylsilyloxy-3-[2,4-dimethylphenyl]prop-1-yl)spiro[bicyclo(3.2.0)heptane-6,2'-(1,3)dioxolan]-3-endo-ol;
2-exo(3-t-butyldimethylsilyloxy-3-(4-phenylbut-1-yl)spiro[bicyclo(3.2.0)heptane-6,2'-(1,3)dioxolan]-3-endo-ol;
2-exo(3-t-butyldimethylsilyloxy-3-[4-methoxyphenylbut-1-yl)spiro[bicyclo(3.2.0)heptane-6,2'-(1,3)dioxolan]-3-endo-ol;
2-exo(3-t-butyldimethylsilyloxy-3-[3-trifluoromethylphenyl]prop-1-yl)spiro[bicyclo(3.2.0)heptane-6,2'-(1,3)-dioxolan]-3-endo-ol;

4.C.6.b.

3-exo(3-t-butyldimethylsilyloxy-6-ethyloct-1-yl)spiro[-bicyclo(3.2.0)heptane-6,2'-(1,3)dioxolan]-2-endo-ol;
3-exo(3-t-butyldimethylsilyloxy-3-cyclopentylprop-1-yl)spiro[bicyclo(3.2.0)heptane-6,2'-(1,3)dioxolan]-2-endo-ol;
3-exo(3-t-butyldimethylsilyloxy-3-cyclohexylprop-1-yl)spiro[bicyclo(3.2.0)heptane-6,2'-(1,3)dioxolan]-2-endo-ol;
3-exo(3-t-butyldimethylsilyloxy-3-phenylprop-1-yl)spiro[bicyclo(3.2.0)heptane-6,2'-(1,3)dioxolan]-2-endo-ol;
3-exo(3-t-butyldimethylsilyloxy-3-(4-chlorophenyl)-prop-1-yl)spiro[bicyclo(3.2.0)heptane-6,2'-(1,3)dioxolan]-2-endo-ol;
3-exo(3-t-butyldimethylsilyloxy-3-[2,4-dimethylphenyl]prop-1-yl)spiro[bicyclo(3.2.0)heptane-6,2'-(1,3)dioxolan]-2-endo-ol;
3-exo(3-t-butyldimethylsilyloxy-4-phenylbut-1-yl)spiro[bicyclo(3.2.0)heptane-6,2'-(1,3)dioxolan]-2-endo-ol;
3-exo(3-t-butyldimethylsilyloxy-4-[4-methoxyphenyl]-but-1-yl)spiro[bicyclo(3.2.0)heptane-6,2'-(1,3)dioxolan]-2-endo-ol;
3-exo(3-t-butyldimethylsilyloxy-3-[3-trifluoromethylphenyl]prop-1-yl)spiro[bicyclo(3.2.0)heptane-6,2'-(1,3)dioxolan]-2-endo-ol.

Preparation 5

Preparation of Bicycloheptanones by Acid Hydrolysis of Acetals

5.A. Bicycloheptanones with Alkynyl Side Chains

5.A.1. Octynyl Bicycloheptanones

5.A.1.a.

A solution of 1.02 g of the octynyl acetal product isomer A of Procedure 4.A.1. (VIIA) 15 ml of acetonitrile, 5.3 ml of water and 4.2 ml of 2N sulfuric acid was stirred at ambient temperature for 16 hours. The reaction was quenched by neutralization with aqueous sodium bicarbonate and the mixture was extracted with ethyl acetate. The extracts were dried with magnesium sulfate, evaporated to dryness and the residue was purified by short column silica-gel chromatography. Elution with ethyl acetate, gave 609 mg (96% yield) of colorless oil, homogeneous by thin layer chromatography and giving analytical data in accord with the structure 3-endo-hydroxy-2-exo-[3 hydroxy-oct-1-ynyl]bicyclo (3.2.0.)heptan-6-one (VIIIA).

5.A.1.b.

When octynyl acetal product isomer B of Procedure 4.A.1 (VIIB) is reacted by the same procedure, the corresponding regioisomeric ketone, namely 2-endo-hydroxy-3-exo(3-hydroxy-oct-1-ynyl]bicyclo(3.2.0-)heptan-6-one (VIIIB) is obtained.

5.A.2. Other Alkynyl Bicycloheptanones

5.A.2.a.

By applying the procedure of Preparation 5.A.1. to the corresponding alkynyl acetal products (VIIA) of procedure 4.A.2.a, the following compounds are prepared:
3-endo-hydroxy-2-exo-(3-hydroxy-but-1-ynyl)bicyclo[3.2.0]heptan-6-one;
3-endo-hydroxy-2-exo-(3-hydroxy-pent-1-ynyl)-bicyclo[3.2.0]heptan-6-one;
3-endo-hydroxy-2-exo-(3-hydroxy-hex-1-ynyl)-bicyclo[3.2.0]heptan-6-one;
3-endo-hydroxy-2-exo-(3-hydroxy-hept-1-ynyl)-bicyclo[3.2.0]heptan-6-one;
3-endo-hydroxy-2-exo-(3-hydroxy-non-1-ynyl)-bicyclo[3.2.0]heptan-6-one;
3-endo-hydroxy-2-exo-(3-hydroxy-dec-1-ynyl)-bicyclo[3.2.0]heptan-6-one;
3-endo-hydroxy-2-exo-(3-hydroxy-undec-1-ynyl)bicyclo[3.2.0]heptan-6-one;
3-endo-hydroxy-2-exo-(3-hydroxy-dodec-1-ynyl)bicyclo[3.2.0]heptan-6-one;
3-endo-hydroxy-2-exo-(3-hydroxy-pentadec-1-ynyl)-bicyclo[3.2.0]heptan-6-one.

5.A.2.b.

In similar fashion, applying the procedure of Preparation 5.A.1. to the respective alkynyl acetal products (VIIB) of Procedure 4.A.2.b, the following compounds were prepared:
2-endo-hydroxy-3-exo-(3-hydroxy-but-1-ynyl)bycyclo[3.2.0]heptan-6-one;
2-endo-hydroxy-3-exo-(3-hydroxy-pent-1-ynyl)bicyclo[3.2.0]heptan-6-one;
2-endo-hydroxy-3-exo-(3-hydroxy-hex-1-ynyl)bicyclo[3.2.0]heptan-6-one;
2-endo-hydroxy-3-exo-(3-hydroxy-hept-1-ynyl)bicyclo[3.2.0]heptan-6-one;
2-endo-hydroxy-3-exo-(3-hydroxy-non-1-ynyl)bicyclo[3.2.0]heptan-6-one;
2-endo-hydroxy-3-exo-(3-hydroxy-dec-1-ynyl)-bicyclo[3.2.0]heptan-6-one;
2-endo-hydroxy-3-exo-(3-hydroxy-undec-1-ynyl)bicyclo[3.2.0]heptan-6-one;
2-endo-hydroxy-3-exo-(3-hydroxy-dodec-1-ynyl)bicyclo[3.2.0]heptan-6-one;
2-endo-hydroxy-3-exo-(3-hydroxy-pentadec-1-ynyl)bicyclo[3.2.0]heptan-6-one.

5.A.3. Bicycloheptanones with Alkynyl Side Chains Containing Branched Alkyl, Cycloalkyl, Phenyl or Substituted Phenyl Groups 5.A.3.a.

By employing the procedure of Preparation 5.A.1. on the alkynyl [isomer (VIIA)]products prepared by Preparation 4.A.3.a., the corresponding ketones were prepared, as follows:
3-endo-hydroxy-2-exo-(3-hydroxy-6-ethyloct-1-ynyl)-bicyclo[3.2.0]heptan-6-one;
3-endo-hydroxy-2-exo-(3-hydroxy-3-cyclopentylprop-1-ynyl)bicyclo[3.2.0]heptan-6-one;
3-endo-hydroxy-2-exo-(3-hydroxy-3-cyclohexylprop-1-ynyl)-bicyclo[3.2.0]heptan-6-one;
3-endo-hydroxy-2-exo-(3-hydroxy-3-phenylprop-1-ynyl)bicyclo[3.2.0]heptan-6-one;
3-endo-hydroxy-2-exo-(3-hydroxy-3-(4-chlorophenyl)-prop-1-ynyl)-bicyclo[3.2.0]heptan-6-one;
3-endo-hydroxy-2-exo-(3-hydroxy-3-(2,4-dimethylphenyl)prop-1-ynyl)-bicyclo[3.2.0]heptan-6-one;
3-endo-hydroxy 2-exo-(3-hydroxy-4-phenylbut-1-ynyl)-bicyclo[3.2.0]heptan-6-one;
3-endo-hydroxy-2-exo-(3-hydroxy-4-(4-methoxyphenyl) but-1-ynyl)-bicyclo[3.2.0]heptan-6-one;
3-endo-hydroxy-2-exo-(3-hydroxy-3-(3-trifluoromethylphenyl)prop-1-ynyl)-bicyclo[3.2.0]heptan-6-one;

5.A.3.b.

In similar fashion, using the procedure of Preparation 5.A.1. to convert the regioisomer (VIIB) products prepared according to procedure 4.A.3.b, the following compounds were prepared:
2-endo-hydroxy-3-exo-(3-hydroxy-6-ethyloct-1-ynyl)-bicyclo[3.2.0]heptan-6-one;
2-endo-hydroxy-3-exo-(3-hydroxy-3-cyclopentylprop-1-ynyl)bicyclo[3.2.0]heptan-6-one;
2-endo-hydroxy-3-exo-(3-hydroxy-3-cyclohexylprop-1-ynyl)-bicyclo[3.2.0]heptan-6-one;
2-endo-hydroxy-3-exo-(3-hydroxy-3-phenylprop-1-ynyl)bicyclo[3.2.0]heptan-6-one;
2-endo-hydroxy-3-exo-(3-hydroxy-3-(4-chlorophenyl)-prop-1-ynyl)-bicyclo[3.2.0]heptan-6-one;
2-endo-hydroxy-3-exo-(3-hydroxy-3-(2,4-dimethylphenyl)prop-1-ynyl)-bicyclo[3.2.0]heptan-6-one;
2-endo-hydroxy-3-exo-(3-hydroxy-4-phenylbut-1-ynyl-bicyclo[3.2.0]heptan-6-one;
2-endo-hydroxy-3-exo-(3-hydroxy-4-(4-methoxyphenylbut-1-ynyl)-bicyclo[3.2.0]heptan-6-one;
2-endo-hydroxy-3-exo-(3-hydroxy-3-(3-trifluoromethylphenyl)prop-1-ynyl)-bicyclo[3.2.0]heptan-6-one;

5.A.4. Octynyl Bicycloheptanones from Hydrolysis of Octynyl t-Butyldimethylsilyloxy Acetals A solution of 0.5 g of 2-exo-(3-t-butyldimethylsilyloxyoct-1-ynyl)spiro[bicyclo(3.2.0)heptan-6,2'-(1,3)dioxolan]-3-endo-ol (from Preparation 4.A.4), 7 ml of acetonitrile, 2.5 ml water, and 2.5 ml of 2N sulfuric acid was stirred at ambient temperature for 16 hours. The reaction mixture was quenched by neutralization with aqueous sodium bicarbonate and the mixture was extracted with ethyl acetate. The solution was evaporated to dryness and the residue was purified by silica gel column chromatography with ethyl acetate-hexane 7:3 to give 3-endo-hydroxy-2-exo-(3-hydroxyoct-1-ynyl)bicyclo[3.2.0]heptan-6-one.

Similarly, starting with 3-exo-(3-t-butyldimethylsilyloxyoct-1-ynyl)spiro[bicyclo(3.2.0)heptan-6,2'-(1,3)dioxolan]-2-endo-ol (from Preparation 4.A.4), there was obtained 2-endo-hydroxy-3-exo-(3-hydroxyoct-1-ynyl)bicyclo[3.2.0]heptan-6-one.

5.A.5. Other Alkynyl Bicycloheptanones from Hydrolysis of t-Butyldimethylsilyloxy Acetals By applying the same procedure as 5.A.4. on the compounds in 4.A.5. the compounds of 5.A.2 were obtained.

5.A.6. Bicycloheptanones with Alkynyl Side Chains Containing Branched Alkyl, Cycloalkyl, Phenyl or Substituted Phenyl Groups from Hydrolysis of t-Butyldimethylsilyloxy Acetals By applying the same procedure as 5.A.4. on the compounds in 4.A.6. the compounds of 5.A.3 were obtained.

5.B. Bicycloheptanones with Alkenyl Side Chains

5.B.1. Octenyl Bicycloheptanones

By using the procedure of Preparation 5.A.1. to hydrolyze the octenyl acetal products prepared according to Preparation 4.B.1, the following compounds are prepared:
3-endo-hydroxy-2-exo-[3-hydroxyoct-1-trans-enyl]-bicyclo-(3.2.0.)heptan-6-one;
2-endo-hydroxy-3-exo(3-hydroxyoct-1-trans-enyl]bicyclo-(3.2.0)heptan-6-one.

5.B.2. Other Alkenyl Bicycloheptanones

5.B.2.a.

Similarly, employing the hydrolysis procedure of Preparation 5.A.1. on the alkenyl acetals prepared according to procedure 4.B.2.a, the corresponding ketones are obtained:
3-endo-hydroxy-2-exo-(3-hydroxybut-1-trans-enyl)-bicyclo-[3.2.0]heptan-6-one;
3-endo-hydroxy-2-exo-(3-hydroxypent-1-trans-enyl)-bicyclo-[3.2.0]heptan-6-one;
3-endo-hydroxy-2-exo-(3-hydroxyhex-1-trans-enyl)-bicyclo[3.2.0]heptan-6-one;
3-endo-hydroxy-2-exo-(3-hydroxyhept-1-trans-enyl)-bicyclo[3.2.0]heptan-6-one;
3-endo-hydroxy-2-exo-(3-hydroxynon-1-trans-enyl)-bicyclo[3.2.0]heptan-6-one;
3-endo-hydroxy-2-exo-(3-hydroxydec-1-trans-enyl)-bicyclo[3.2.0]heptan-6-one;
3-endo-hydroxy-2-exo-(3-hydroxyundec-1-trans-enyl)-bicyclo-[3.2.0]heptan-6-one;
3-endo-hydroxy-2-exo-(3-hydroxydodec-1-trans-enyl)-bicyclo-[3.2.0]heptan-6-one;
3-endo-hydroxy-2-exo-(3-hydroxypentadec-1-trans-enyl)bicyclo[3.2.0]heptan-6-one;

5.B.2.b.

By using the hydrolysis procedure of Preparation 5.A.1. on the isomeric alkenyl acetals prepared according to procedure 4.B.2.b, the following ketones are obtained:
2-endo-hydroxy-3-exo-(3-hydroxybut-1-trans-enyl)-bicyclo[3.2.0]heptan-6-one;
2-endo-hydroxy-3-exo-(3-hydroxypent-1-trans-enyl)-bicyclo[3.2.0]heptan-6-one;
2-endo-hydroxy-3-exo-(3-hydroxyhex-1-trans-enyl)-bicyclo[3.2.0]heptan-6-one;
2-endo-hydroxy-3-exo-(3-hydroxyhept-1-trans-enyl)-bicyclo[3.2.0]heptan-6-one;
2-endo-hydroxy-3-exo-(3-hydroxynon-1-trans-enyl)-bicyclo[3.2.0]heptan-6-one;
2-endo-hydroxy-3-exo-(3-hydroxydec-1-trans-enyl)-bicyclo[3.2.0]heptan-6-one;
2-endo-hydroxy-3-exo-(3-hydroxyundec-1-trans-enyl)-bicyclo-[3.2.0]heptan-6-one;
2-endo-hydroxy-3-exo-(3-hydroxydodec-1-trans-enyl)-bicyclo-[3.2.0]heptan-6-one;
2-endo-hydroxy-3-exo-(3-hydroxypentadec-1-trans-enyl)bicyclo[3.2.0]heptan-6-one;

5.B.3. Bicycloheptanones with Alkenyl Side Chains Containing Branched Alkyl, Cycloalkyl, Phenyl or Substituted Phenyl Groups

5.B.3.a.

By employing the hydrolysis procedure of Preparation 5.A.1. on the alkenyl side chain acetals prepared according to procedure 4.B.3.a, the following compounds are prepared:
3-endo-hydroxy-2-exo-(3-hydroxy-6-ethyloct-1-trans-enyl)bicyclo[3.2.0]heptan-6-one;
3-endo-hydroxy-2-exo-(3-hydroxy-3-cyclopentylprop-1-trans-enyl)bicyclo[3.2.0]heptan-6-one;
3-endo-hydroxy-2-exo-(3-hydroxy-3-cyclohexylprop-1-trans-enyl)bicyclo[3.2.0]heptan-6-one;
3-endo-hydroxy-2-exo-(3-hydroxy-3-phenylprop-1-trans-enyl)bicyclo[3.2.0]heptan-6-one;
3-endo-hydroxy-2-exo-(3-hydroxy-3-(4-chlorophenyl)-prop-1-trans-enyl)-bicyclo[3.2.0]heptan-6-one;
3-endo-hydroxy-2-exo-(3-hydroxy-3-(2,4-dimethylphenyl)prop-1-trans-enyl)-bicyclo[3.2.0]heptan-6-one;
3-endo-hydroxy 2-exo-(3-hydroxy-4-phenylbut-1-trans-enyl)bicyclo[3.2.0]heptan-6-one;
3-endo-hydroxy-2-exo-(3-hydroxy-4-(4-methoxy)-phenylbut-1-trans-enyl)-bicyclo[3.2.0]heptan-6-one;
3-endo-hydroxy-2-exo-(3-hydroxy-3-(3-trifluoromethylphenyl)prop-1-trans-enyl)-bicyclo[3.2.0]heptan-6-one;

5.B.3.b.

Similarly, subjecting the alkenyl acetal isomer (VIIB) products of procedure 4.B.3.b to the hydrolysis conditions of Preparation 5.A.1, the following compounds are prepared:
2-endo-hydroxy-3-exo-(3-hydroxy-6-ethyloct-1-transenyl)-bicyclo[3.2.0]heptan-6-one;
2-endo-hydroxy-3-exo-(3-hydroxy-3-cyclopentylprop-1-trans-enyl)-bicyclo[3.2.0]heptan-6-one;
2-endo-hydroxy-3-exo-(3-hydroxy-3-cyclohexylprop-1-trans-enyl)-bicyclo[3.2.0]heptan-6-one;
2-endo-hydroxy-3-exo-(3-hydroxy-3-phenylprop-1-trans-enyl)-bicyclo[3.2.0]heptan-6-one;
2-endo-hydroxy-3-exo-(3-hydroxy-3-(4-chlorophenyl)-prop-1-trans-enyl)-bicyclo[3.2.0]heptan-6-one;
2-endo-hydroxy-3-exo-(3-hydroxy-3-(2,4-dimethylphenyl)prop-1-trans-enyl)-bicyclo[3.2.0]heptan-6-one;
2-endo-hydroxy-3-exo-(3-hydroxy-4-phenylbut-1-trans-enyl)-bicyclo[3.2.0]heptan-6-one;
2-endo-hydroxy 3-exo-(3-hydroxy-4-(4-methoxyphenyl)but-1-trans-enyl)-bicyclo[3.2.0]heptan-6-one;
2-endo-hydroxy-3-exo-(3-hydroxy-3-(3-trifluoromethylphenyl)prop-1-trans-enyl)-bicyclo[3.2.0]heptan-6-one;

5.C. Bicycloheptanones with Alkyl Side Chains

5.C.1. Octyl Bicycloheptanones

By using the hydrolysis procedure of Preparation 5.A.1. on the octyl bicycloheptane acetals prepared according to procedure of Preparation 4.C.1. or 4.C.4, the following compounds are prepared:

3-endo-hydroxy-2-exo-[3 hydroxyoct-1-yl]bicyclo-(3.2.0.)heptan-6-one;
2-endo-hydroxy-3-exo[3-hydroxyoct-1-yl]bicyclo-(3.2.0)heptan-6-one.

5.C.2. Other Alkyl Bicycloheptanones

5.C.2.a.

Similarly, by using the procedure of Preparation 5.A.1. on the octyl acetal products prepared according to procedure 4.C.2.a or 4.C.5, the following ketones are prepared:

3-endo-hydroxy-2-exo-(3-hydroxybut-1-yl)-bicyclo[3.2.0]heptan-6-one;
3-endo-hydroxy-2-exo-(3-hydroxypent-1-yl)-bicyclo[3.2.0]heptan-6-one;
3-endo-hydroxy-2-exo-(3-hydroxyhex-1-yl)-bicyclo[3.2.0]heptan-6-one;
3-endo-hydroxy-2-exo-(3-hydroxyhept-1-yl)-bicyclo[3.2.0]heptan-6-one;
3-endo-hydroxy-2-exo-(3-hydroxynon-1-yl)-bicyclo[3.2.0]heptan-6-one;
3-endo-hydroxy-2-exo-(3-hydroxydec-1-yl)-bicyclo[3.2.0]heptan-6-one;
3-endo-hydroxy-2-exo-(3-hydroxyundec-1-yl)-bicyclo[3.2.0]heptan-6-one;
3-endo-hydroxy-2-exo-(3-hydroxydodec-1-yl)-bicyclo[3.2.0]heptan-6-one;
3-endo-hydroxy-2-exo-(3-hydroxypentadec-1-yl)bicyclo[3.2.0]heptan-6-one;

5.C.2.b.

Employing the same hydrolysis procedure of Preparation 5.A.1. on the regioisomeric alkyl acetal products (VIIB) prepared according to procedure 4.C.2.b or 4.C.5, the following compounds are prepared:

2-endo-hydroxy-3-exo-(3-hydroxybut-1-yl)-bicyclo[3.2.0]heptan-6-one;
2-endo-hydroxy-3-exo-(3-hydroxypent-1-yl)-bicyclo[3.2.0]heptan-6-one;
2-endo-hydroxy-3-exo-(3-hydroxyhex-1-yl)-bicyclo[3.2.0]heptan-6-one;
2-endo-hydroxy-3-exo-(3-hydroxyhept-1-yl)-bicyclo[3.2.0]heptan-6-one;
2-endo-hydroxy-3-exo-(3-hydroxynon-1-yl)-bicyclo[3.2.0]heptan-6-one;
2-endo-hydroxy-3-exo-(3-hydroxydec-1-yl)-bicyclo[3.2.0]heptan-6-one;
2-endo-hydroxy-3-exo-(3-hydroxyundec-1-yl)-bicyclo[3.2.0]heptan-6-one;
2-endo-hydroxy-3-exo-(3-hydroxydodec-1-yl)-bicyclo[3.2.0]heptan-6-one;
2-endo-hydroxy-3-exo-(3-hydroxypentadec-1-yl)-bicyclo[3.2.0]heptan-6-one;

5.C.3. Bicycloheptanones with Alkyl Side Chains Containing Branched Alkyl, Cycloalkyl, Phenyl or Substituted Phenyl Groups

5.C.3.a

Employing the hydrolysis procedure of Preparation 5.A.1. on the alkyl side products prepared by chain acetal procedure 4.C.3.a or 4.C.6, the following compounds are prepared:

3-endo-hydroxy-2-exo-(3-hydroxy-6-ethyloct-1-yl)bicyclo[3.2.0]heptan-6-one;
3-endo-hydroxy-2-exo-(3-hydroxy-3-cyclopentylprop-1-yl)bicyclo[3.2.0]heptan-6-one;
3-endo-hydroxy-2-exo-(3-hydroxy-3-cyclohexylprop-1-yl)bicyclo[3.2.0]heptan-6-one;
3-endo-hydroxy-2-exo-(3-hydroxy-3-phenylprop-1-yl)bicyclo[3.2.0]heptan-6-one;
3-endo-hydroxy-2-exo-(3-hydroxy-3-(4-chlorophenyl)-prop-1-yl)-bicyclo[3.2.0]heptan-6-one;
3-endo-hydroxy-2-exo-(3-hydroxy-3-(2,4-dimethylphenyl)prop-1-yl)-bicyclo[3.2.0]heptan-6-one;
3-endo-hydroxy 2-exo-(3-hydroxy-4-phenylbut-1-yl)bicyclo[3.2.0]heptan-6-one;
3-endo-hydroxy-2-exo-(3-hydroxy-4-(4-methoxyphenyl)but-1-yl)-bicyclo[3.2.0]heptan-6-one;
3-endo-hydroxy-2-exo-(3-hydroxy-3-(3-trifluoromethylphenyl)prop-1-yl)-bicyclo[3.2.0]heptan-6-one.

5.C.3.b.

By employing the procedure of Preparation 5.A.1. on the alkyl side chain acetals of the regioisomer (VIIB) series prepared according to procedure 4.C.3.b or 4.C.6, the following ketones are prepared:

2-endo-hydroxy-3-exo-(3-hydroxy-6-ethyloct-1-yl)bicyclo[3.2.0]heptan-6-one;
2-endo-hydroxy-3-exo-(3-hydroxy-3-cyclopentylprop-1-yl)bicyclo[3.2.0]heptan-6-one;
2-endo-hydroxy-3-exo-(3-hydroxy-3-cyclohexylprop-1-yl)-bicyclo[3.2.0]heptan-6-one;
2-endo-hydroxy-3-exo-(3-hydroxy-3-phenylprop-1-yl)bicyclo[3.2.0]heptan-6-one;
2-endo-hydroxy-3-exo-(3-hydroxy-3-(4-chlorophenyl)-prop-1-yl)-bicyclo[3.2.0]heptan-6-one;
2-endo-hydroxy-3-exo-(3-hydroxy-3-(2,4-dimethylphenyl)prop-1-yl)-bicyclo[3.2.0]heptan-6-one;
2-endo-hydroxy 3-exo-(3-hydroxy-(4-phenylbut-1-yl)bicyclo[3.2.0]heptan-6-one;
2-endo-hydroxy-3-exo-(3-hydroxy-4-(4-methoxyphenyl)but-1-yl)-bicyclo[3.2.0]heptan-6-one;
2-endo-hydroxy-3-exo-(3-hydroxy-3-(3-trifluoromethylphenyl)prop-1-yl)-bicyclo[3.2.0]heptan-6-one.

Preparation 6

Preparation of 3-Aminooxypropionic acid

To a solution of 24 g of acetoxime in 40 ml of dioxane was added 0.4 g of sodium methoxide. The mixture was stirred at room temperature for 30 minutes then cooled to 0° C. with an ice bath. 30 ml of methyl acrylate was added, and the resulting mixture was let warm to room temperature and stirred for 3 hours. 1N HCl was added until pH 6.8 was reached. After extractive isolation (ether), the product was purified by distillation. Yield 8.3 g.

The oxime adduct was heated in the presence of 10 ml of 5N HCl to 60° C. until the reaction was complete (as determined by NMR spectrum of an aliquot of a vacuum dried sample). The bulk of the solvent was removed under vacuum and the product separated as white solid. Yield 2.70 g. of the HCl salt of 3-aminooxypropionic acid. M.P.: 151° C.

Preparation 7

Preparation of 4-Aminooxybutyric acid 10 g of benzophenone oxime was dissolved in 20 ml of dry N-methylpyrrolidone. 1.16 g of sodium was added and the mixture was stirred at 60° C. until all sodium was dissolved. The solution was then cooled to room temperature and 4.3 g of freshly distilled γ-butyrolactone was added. The mixture was refluxed for 4 hours under constant stirring, then concentrated under vacuum to half of its original volume and poured into 500 ml of water. Any undissolved material was removed by filtration and the solution was cooled and acidified with acetic acid. After standing one hour at room temperature the precipitate was collected by filtration, dissolved in acetone and treated with Norit (activated charcoal). Cold water was added to the filtrate until turbidity appeared and the mixture was refrigerated overnight. More water was then added and the precipitated N-diphenylmethylidene-aminooxybutyric acid was collected. To a solution of 0.03 mole of N-diphenylmethylidene-aminooxybutyric acid in 100 ml of 18% hydrochloric acid was added 20 ml of acetic acid, and the mixture was successively refluxed for half an hour, cooled, washed with ether and evaporated in vacuo. The residue was dissolved in absolute ethanol and treated with Norit. Dry ether was added to the filtered solution until turbidity appeared. The mixture was kept overnight at 0° C.–20° C. and the precipitated 4-aminooxybutyric acid hydrochloride was collected and recrystallized from ethanol-ether.

Prepatation 8

Preparation of 5-Aminooxyvaleric acid

5-Aminooxyvaleric acid is prepared in the same manner using the procedure of Preparation 6 for 4-aminooxybutyric acid except that the γ-butyrolactone is replaced by σ-valerolactone.

Preparation 9

Preparation of Individual Alkynyl Diastereoisomers

9.A. Octynyl t-Butyldimethylsilyloxy Acetals

A solution of 80 mg 3-exo-(3-t-butyldimethylsilyloxyoct-1-ynyl)spiro[bicyclo(3.2.0)heptane-6,2'-(1,3)dioxolan]-2-endo-ol from Preparation 4.A.4 and 100 mg of dicobaltcarbonyl was stirred at ambient temperature for 2 hours. The solvent was removed by evaporation and the residue was separated into two components using silica gel column chromatography and eluting with acetone-dichloramethane (2:98). The first eluted was shown to be the cobalt hexacarbonyl complex of 3-exo-(3α-t-butyldimethylsilyloxyoct-1-ynyl)spiro[bicyclo(3.2.0)heptane-6,2'-(1,3)dioxolan]-2-endo-ol (isomer A) and the next eluted was shown to be the cobalt hexacarbonyl complex of 3-exo-(3β-t-butyldimethylsilyloxyoct-1-ynyl)spiro[bicyclo(3.2.0)heptane-6,2'-(1,3)dioxolan]-2-endo-ol (isomer B). To a stirred solution of 30 mg of isomer A in 2 ml of acetone-water (9:1) was added 120 mg of ceric ammonium nitrate. Carbon monoxide was liberated and the red color disappeared. After 2 minutes, 20 ml water was added and the mixture was extracted thoroughly with diethyl ether. The organic extracts were combined and were extracted with saturated sodium chloride solution. After drying over sodium sulfate and evaporation, there was otained 3-exo-(3α-t-butyldimethylsilyloxyoct-1-ynyl)spiro[bicyclo (3.2.0)heptane-6,2'-(1,3)dioxolan]-2-endo-ol.

Similarly, by cleavage of isomer B there was obtained 3-exo-(3β-t-butyldimethylsilyloxyoct-1-ynyl)spiro[bicyclo (3.2.0)heptane-6,2'-(1,3)dioxolan]-2-endo-ol.

9.B. Other Alkynyl t-Butyldimethylsilyloxy Acetals

Similarly, following the procedure of Preparation 9.A. and using the compounds in Preparation 4.A.5. there were obtained the individual α and β diastereoisomers of the compounds in Preparation 4.A.5.

9.C. Alkynyl t-Butyldimethylsilyloxy Acetals with Side Chains Containing Branched Alkyl, Cycloalkyl, Phenyl or Substituted Phenyl Groups Similarly, following the procedure of Preparation 9.A. and using the compounds in Preparation 4.A.6 there were obtained the individual α and β diastereoisomers of the compounds in Preparation 4.A.6.

9.D. Octynyl Acetals

Using the procedure of 4.A.7 on the products of Preparation 9.A, there were obtained
3-exo-(3α-hydroxyoct-1-ynyl)spiro[bicyclo(3.2.0)heptane-6,2'-(1,3)dioxolan]-2-endo-ol and
3-exo-(3β-hydroxyoct-1-ynyl)spiro[bicyclo(3.2.0)heptane-6,2'-(1,3)dioxolan]-2-endo-ol.

9.E. Other Alkynyl Acetals

Similarly, using the procedure of 4.A.7 on the compounds of Preparation 9.B, there were obtained the individual α and β diastereoisomers of Preparation 4.A.2.

9.F. Alkynyl Acetals with Side Chains Containing Branched Alkyl, Cycloalkyl, Phenyl or Substituted Phenyl Groups Similarly, using the procedure of 4.A.7 on the products of Preparation 9.C, there were obtained the individual α and β diastereoisomers of Preparation 4.A.3.

9.G. Octynyl Bicycloheptanones

Using the procedure of 5.A.4 on the products of 9.A, one obtains the individual α and β isomers of the products of 5.A.1.

9.H. Other Alkynyl Bicycloheptanones

Using the procedure of 5.A.4. on the products of 9.B., one obtains the individual α and β isomers of the products of 5.A.2.

9.I. Alkynyl Bicycloheptanones Containing Branched Alkyl, Cycloalkyl, Phenyl or Substituted Phenyl Groups Using the procedure of 5.A.4 on the products of 9.C, one obtains the individual α and β isomers of 5.A.3.

Preparation 10

Preparation of αβS-Hydroxy Side Chain Isomers

10.A. Octynyl t-Butyldimethylsilyloxy Acetals

Following the procedure of Preparation 4.A.4 using S-3-(t-butyldimethylsilyloxy)oct-1-yne and applying the method of Preparation 9.A, there were obtained 2-exo-(3αβS-t-butyldimethylsilyloxyoct-1-ynyl)spiro[bicyclo(3.2.0)heptane-6,2'-(1,3)dioxolan]-3-endo-ol and 3-exo-(3αβS-t-butyldimethylsilyloxyoct-1-ynyl)spiro[bicyclo(3.2.0)heptane-6,2'-(1,3)dioxolan]-2-endo-ol.

10.B. Other alkynyl t-Butyldimethylsilyloxy Acetals

Similarly, following the procedure of Preparation 4.A.5 using the appropriate S-3-(t-butyldimethylsilyloxy)alk-1-yne and applying the method of Preparation 9.B, αβS-t-butyldimethylsilyloxy compounds of 4.A.5 were obtained.

10.C. Alkynyl t-Butyldimethylsilyloxy Acetals with Side Chains Containing Branched Alkyl, Cycloalkyl, Phenyl or Substituted Phenyl Groups Similarly, following the procedure of 4.A.6 using the appropriate S-3-(t-butyldimethylsilyloxy)alk-1-yne and applying the method of Preparation 9.C, the αβS-t-butyldimethylsilyloxy compounds of 4.A.6 were obtained.

10.D. Octynyl Acetals

Using the procedure of 4.A.7 on the products of 10.A, there was obtained 3-exo-(3αβS-hydroxyoct-1-ynyl)spiro[bicyclo(3.2.0)heptane-6,2'-(1,3)dioxolan]-2-endo-ol.

10.E. Other Alkynyl Acetals

Similarly, using the procedure of 4.A.7 on the products of 10.B, there were obtained the αβS-isomers of the products of 4.A.2.

10.F. Alkynyl Acetals with Side Chains Containing Branched Alkyl, Cycloalkyl, Phenyl or Subtstituted Phenyl Groups Similarly, using the procedure of 4.A.7 on the products of 10.C, there were obtained αβS-isomers of the products of 4.A.3.

10.G. Octynyl Bicycloheptanones

Using the procedure of Preparation of 5.A.4 on the products of 10.A, one obtains the individual αβS-isomers of the products of 5.A.1.

10.H. Other Alkynyl Bicycloheptanones

Using the procedure of Preparation 5.A.4 on the products of 10.B, one obtains the αβS-isomers of the products of 5.A.2.

10.I. Alkynyl Bicycloheptanones with Side Chains Containing Branched Alkyl, Cycloalkyl, Phenyl or Substituted Phenyl Groups Using the procedure of 5.A.4 on the products of 10.C, one obtains the αβS-isomers of the products of 5.A.3.

Preparation 11

Preparation of αS-Hydroxy Side Chain Isomers

11.A. Octynyl t-Butyldimethylsilyloxy Acetals

Following the procedure of Preparation 9.A, using the products of Preparation 10.A, one obtains 3-exo-(3αS-t-butyldimethylsilyloxyoct-1-ynyl)spiro[bicyclo(3.2.0)heptane-6,2'-(1,3)dioxolan]-2-endo-ol.

11.B. Other Alkynyl t-Butyldimethylsilyloxy Acetals

Following the procedure of Preparation 9.B using the products of Preparation 10.B, one obtains the 3αS-isomers of 4.A.5.

11.C. Alkynyl t-Butyldimethylsilyloxy Acetals with Side Chains Containing Branched Alkyl, Cycloalkyl, Phenyl or Substituted Phenyl Following the procedure of Preparation 9.C using the products of Preparation 10.C, one obtains the 3αS-isomers of 4.A.6.

11.D. Octynyl Acetals

Using the procedure of Preparation 4.A.7 on the products of 11.A, there was obtained 3-exo-(3αS-hydroxyoct-1-ynyl)spiro[bicyclo(3.2.0)heptane-6,2'-(1,3)dioxolan]-2-endo-ol.

11.E. Other Alkynyl Acetals

Using the procedure of Preparation 4.A.7 on the products of 11.B, there were obtained the 3αS-isomers of the products of 4.A.2.

11.F. Alkynyl Acetals with Side Chains Containing Branched Alkyl, Cycloalkyl, Phenyl or Substituted Phenyl Groups Using the procedure of Preparation 4.A.7 on the products of 11.C, there were obtained the 3αS-isomers of the products of 4.A.3.

11.G. Octynyl Bicycloheptanones

Using the procedure of Preparation 5.A.4 on the products of 11.A, one obtains 2-endo-hydroxy-3-exo-(3αS-hydroxyoct-1-ynyl)bicyclo[3.2.0]heptan-6-one.

11.H. Other Alkynyl Bicycloheptanones

Using the procedure of Preparation 5.A.4 on the products of 11.B, one obtains the 3αS isomers of the products of 5.A.2.

11.I. Alkynyl Bicycloheptanones with Side Chains Containing Branched Alkyl, Cycloalkyl, Phenyl or Substituted Phenyl Groups Using the procedure of Preparation 5.A.4 on the products of 11.C, one obtains the 3αS-isomers of the products of 5.A.3.

Preparation 12

Preparation of 3αS-Hydroxyoct-1-trans-enyl Side Chain

12.A. Octenyl Acetal

Using the procedure of Preparation 4.B.4 on the products of Preparation 11.D gave 3-exo-(3αS-hydroxyoct-1-trans-enyl)spiro[bicyclo(3.2.0) heptane-6,2'-(1,3)dioxolan]-2-endo-ol.

12.B. Octenyl Bicycloheptanone

Using the procedure Preparation 5.A.1 on the products of Preparation 12.A gave 2-endo-3-exo-(3αS-hydroxyoct-1-trans-enyl)bicyclo[3.2.0]-heptan-6-one.

EXAMPLE 1

Alkynyl Aminooxypropionic Acids of Formula (1)

A. This example illustrates a method, according to the invention, of preparing a compound of the invention having the formula N-[3-endo-hydroxy-2-exo-(3-hydroxy-oct-1-ynyl)bicyclo[3.2.0]hept-6-ylidene]-3-aminooxypropionic acid (1).

1. A mixture of 80 mg 3-endo-hydroxy-2-exo-(3-hydroxy-oct-1-ynyl)bicyclo[3.2.0]heptan-6-one (VIIIA) (Preparation 5.A.1.a.) and 53 mg of sodium acetate were dissolved in 4 ml of methanol and added to a solution of 68 mg of 3-aminooxypropionic acid hydrochloric acid salt (Preparation 6) dissolved in 2 ml of methanol. The reaction mixture was stirred at room temperature for one hour and at which time completeness of the reaction was confirmed by thin layer chromatography using methylene chloride-methanol-acetic acid (92:7.5:0.5). After evaporation of the solvent, the residue was extracted several times with ethyl acetate and the combined extracts were washed several times with saturated aqueous salt solution, dried over magnesium sulfate, and evaporated under reduced pressure to furnish a crystalline residue of the desired N-[3-endo-hydroxy-2-exo-(3-hydroxy-oct-1-ynyl)bicyclo[3.2.0-]hept-6-ylidene]-3-aminooxypropionic acid, purified by recrystallization from ethylacetate-heptane. Melting point.: 81° C.-83° C.

B. Similarly, by following the procedure of Example 1.A.1. but substituting 3-endo-hydroxy-2-exo-(3-hydroxy-oct-1-ynyl)bicyclo[3.2.0]heptan-6-one by the corresponding alkynyl bicycloheptanone isomer (A) chosen from compounds prepared in Preparation 5.A.2.a, the following compounds are prepared
N-[3-endo-hydroxy-2-exo-(3-hydroxybut-1-ynyl)bicyclo[3.2.0]hept-6-ylidene]-3-aminooxypropionic acid;
N-[3-endo-hydroxy-2-exo-(3-hydroxypent-1-ynyl)bicyclo[3.2.0]hept-6-ylidene]-3-aminooxypropionic acid;
N-[3-endo-hydroxy-2-exo-(3-hydroxyhex-1-ynyl)bicyclo[3.2.0]hept-6-ylidene]-3-aminooxypropionic acid;
N-[3-endo-hydroxy-2-exo-(3-hydroxyhept-1-ynyl)bicyclo[3.2.0]hept-6-ylidene]-3-aminooxypropionic acid;
N-[3-endo-hydroxy-2-exo-(3-hydroxynon-1-ynyl)bicyclo[3.2.0]hept-6-ylidene]-3-aminooxypropionic acid;
N-[3-endo-hydroxy-2-exo-(3-hydroxydec-1-ynyl)bicyclo[3.2.0]hept-6-ylidene]-3-aminooxypropionic acid;
N-[3-endo-hydroxy-2-exo-(3-hydroxyundec-1-ynyl)-bicyclo[3.2.0]hept-6-ylidene]-3-aminooxypropionic acid;
N-[3-endo-hydroxy-2-exo-(3-hydroxydodec-1-ynyl)-bicyclo[3.2.0]hept-6-ylidene]-3-aminooxypropionic acid.

C. In a similar manner by following the procedure of Example 1.A.1. but employing in place of 3-endohydroxy-2-exo-(3-hydroxy-oct-1-ynyl)bicyclo[3.2.0]heptan-6-one the corresponding alkynyl bicycloheptanone isomer (A) chosen from those compounds prepared and listed in Preparation 5.A.3.a. the following representative compounds are prepared:
N-[3-endo-hydroxy-2-exo-(3-hydroxy-6-ethyloct-1-ynyl)bicyclo[3.2.0]hept-6-ylidene]-3-aminooxypropionic acid;
N-[3-endo-hydroxy-2-exo-(3-hydroxy-3-cyclopentylprop-1ynyl)-bicyclo[3.2.0]hept-6-ylidene]-3-aminooxypropionic acid;
N-[3-endo-hydroxy-2-exo-(3-hydroxy-3-cyclohexylprop-1ynyl)bicyclo[3.2.0]hept-6-ylidene]-3-aminooxypropionic acid;
N-[3-endo-hydroxy-2-exo-(3-hydroxy-3-phenylprop-1ynyl)bicyclo[3.2.0]hept-6-ylidene]-3-aminooxypropionic acid;
N-[3-endo-hydroxy-2-exo-(3-hydroxy-3-(4-chlorophenyl)prop-1-ynyl)-bicyclo[3.2.0]hept-6-ylidene]3-aminooxypropionic acid;
N-[3-endo-hydroxy-2-exo-(3-hydroxy-3-(2,4-dimethylphenyl)prop-1-ynyl)-bicyclo[3.2.0]hept-6-ylidene]-3-aminooxypropionic acid;
N-[3-endo-hydroxy-2-exo-(3-hydroxy-(4-phenylbut-1-ynyl)bicyclo[3.2.0]hept-6-ylidene]-3-aminooxypropionic acid;
N-[3-endo-hydroxy-2-exo-(3-hydroxy-4-(4-methoxyphenyl)-but-1-ynyl)-bicyclo[3.2.0]hept-6-ylidene]-3-aminooxypropionic acid;
N-[3-endo-hydroxy-2-exo-(3-hydroxy-3-(3-trifluoromethylphenyl)prop-1-ynyl)-bicyclo[3.2.0]hept-6-ylidene]-3-aminooxypropionic acid.

EXAMPLE 2

Alkenyl Aminooxypropionic Acid of Formula (1)

A. This example illustrates a method, according to the invention, of preparing a compound of the invention, namely N-[3-endo-hydroxy-2-exo-(3-hydroxyoct-1-trans-enyl)bicyclo[3.2.0]hept-6-ylidene]-3-aminooxypropionic acid. This compound is prepared by following the procedure of Example 1.A.1, but employing, in place of 3-endo-hydroxy-2-exo-(3-hydroxyoct-1-ynyl)-bicyclo[3.2.0]heptan-6-one used therein 3-endo-hydroxy-2-exo-(3-hydroxy-oct-1-trans-enyl)bicyclo[3.2.0]heptan-6-one prepared according to Preparation 5.B.1.a.

B. Similarly, by following the procedure of Example 1.A.1, but substituting for 3-endo-hydroxy-2-exo-(3-hydroxy-oct-1-ynyl)bicyclo[3.2.0]heptan-6-one the corresponding alkenyl bicycloheptanone prepared according to Preparation 5.B.2.a., the following compounds are prepared:
N-[3-endo-hydroxy-2-exo-(3-hydroxybut-1-trans-enyl)bicyclo[3.2.0]hept-6-ylidene]-3-aminooxypropionic acid;
N-[3-endo-hydroxy-2-exo-(3-hydroxypent-1-trans-enyl)bicyclo[3.2.0]hept-6-ylidene]-3-aminooxypropionic acid;
N-[3-endo-hydroxy-2-exo-(3-hydroxyhex-1-trans-enyl)-bicyclo[3.2.0]hept-6-ylidene]-3-aminooxypropionic acid;
N-[3-endo-hydroxy-2-exo-(3-hydroxyhept-1-trans-enyl)bicyclo[3.2.0]hept-6-ylidene]-3-aminooxypropionic acid;
N-[3-endo-hydroxy-2-exo-(3-hydroxynon-1-trans-enyl)-bicyclo[3.2.0]hept-6-ylidene]-3-aminooxypropionic acid;
N-[3-endo-hydroxy-2-exo-(3-hydroxydec-1-trans-enyl)-bicyclo[3.2.0]hept-6-ylidene]-3-aminooxypropionic acid;
N-[3-endo-hydroxy-2-exo-(3-hydroxyundec-1-trans-enyl)bicyclo[3.2.0]hept-6-ylidene]-3-aminooxypropionic acid;
N-[3-endo-hydroxy-2-exo-(3-hydroxydodec-1-trans-enyl)bicyclo[3.2.0]hept-6-ylidene]-3-aminooxypropionic acid.

C. In a similar manner by following the procedure of Example 1.A.1, but substituting 3-endo-hydroxy-2-exo-(3-hydroxy-oct-1-ynyl)bicyclo[3.2.0]heptan-6-one by the corresponding alkenyl bicycloheptanone products prepared in Preparation 5.B.3.a., the following representative oxime ethers are prepared:
N-[3-endo-hydroxy-2-exo-(3-hydroxy-6-ethyloct-1-trans-enyl)bicyclo[3.2.0]hept-6-ylidene]-3-aminooxypropionic acid;
N-[3-endo-hydroxy-2-exo-(3-hydroxy-3-cyclopentylprop-1-trans-enyl)bicyclo[3.2.0]hept-6-ylidene]-3-aminooxypropionic acid;

N-[3-endo-hydroxy-2-exo-(3-hydroxy-3-cyclohexyl-prop-1-trans-enyl)bicyclo[3.2.0]hept-6-ylidene]-3-aminooxypropionic acid;

N-[3-endo-hydroxy-2-exo-(3-hydroxy-3-phenylprop-1-trans-enyl)bicyclo[3.2.0]hept-6-ylidene]-3-aminooxypropionic acid;

N-[3-endo-hydroxy-2-exo-(3-hydroxy-3-(4-chlorophenyl)prop-1-trans-enyl)-bicyclo[3.2.0]hept-6-ylidene]-3-aminooxypropionic acid;

N-[3-endo-hydroxy-2-exo-(3-hydroxy-3-(2,4-dimethylphenyl)prop-1-trans-enyl)-bicyclo[3.2.0]hept-6-ylidene]-3-aminooxypropionic acid;

N-[3-endo-hydroxy 2-exo-(3-hydroxy-4-phenylbut-1-trans-enyl)bicyclo[3.2.0]hept-6-ylidene]-3-aminooxypropionic acid;

N-[3-endo-hydroxy-2-exo-(3-hydroxy-4-(4-methoxyphenylbut-1-trans-enyl)-bicyclo[3.2.0]hept-6-ylidene]3-aminooxypropionic acid; and N-[3-endo-hydroxy-2-exo-(3-hydroxy-3-(3-trifluoromethylphenyl)prop-1-trans-enyl)-bicyclo[3.2.0]hept-6-ylidene]-3-aminooxypropionic acid.

EXAMPLE 3

Alkyl Aminooxypropionic Acid of Formula (1)

A. This example illustrates a method, according to the invention, of preparing a compound of the invention, namely N-[3-endo-hydroxy-2-exo-(3-hydroxyoct-1-yl)-bicyclo[3.2.0]hept-6-ylidene]-3-aminooxypropionic acid. This compound is prepared by following the procedure of Example 1.A.1, but substituting 3-endo-hydroxy-2-exo-(3-hydroxy-oct-1-ynyl)bicyclo[3.2.0]heptan-6-one by 3-endo-hydroxy-2-exo-(3-hydroxy-oct-1-yl)bicyclo[3.2.0]heptan-6-one as prepared in Preparation 5.C.1.a.

B. Similarly, by following the procedure of Example 1.A.1. but substituting 3-endo-hydroxy-2-exo-(3-hydroxy-oct-1-ynyl)bicyclo[3.2.0]heptan-6-one by the corresponding alkyl bicycloheptanone listed in Preparation 5.C.2.a., the following alkyl chain oxime ethers are prepared:

N-[3-endo-hydroxy-2-exo-(3-hydroxybut-1-yl)-bicyclo[3.2.0]hept-6-ylidene]-3-aminooxypropionic acid;

N-[3-endo-hydroxy-2-exo-(3-hydroxypent-1-yl)-bicyclo[3.2.0]hept-6-ylidene]-3-aminooxypropionic acid;

N-[3-endo-hydroxy-2-exo-(3-hydroxyhex-1-yl)-bicyclo[3.2.0]hept-6-ylidene]-3-aminooxypropionic acid;

N-[3-endo-hydroxy-2-exo-(3-hydroxyhept-1-yl)-bicyclo[3.2.0]hept-6-ylidene]-3-aminooxypropionic acid;

N-[3-endo-hydroxy-2-exo-(3-hydroxynon-1-yl)-bicyclo[3.2.0]hept-6-ylidene]-3-aminooxypropionic acid;

N-[3-endo-hydroxy-2-exo-(3-hydroxydec-1-yl)-bicyclo[3.2.0]hept-6-ylidene]-3-aminooxypropionic acid;

N-[3-endo-hydroxy-2-exo-(3-hydroxyundec-1-yl)bicyclo[3.2.0]hept-6-ylidene]-3-aminooxypropionic acid;

N-[3-endo-hydroxy-2-exo-(3-hydroxydodec-1-yl)bicyclo[3.2.0]hept-6-ylidene]-3-aminooxypropionic acid.

C. In a similar manner by following the procedure of Example 1.A.1, but substituting 3-endo-hydroxy-2-exo-(3-hydroxy-oct-1-ynyl)bicyclo[3.2.0]heptan-6-one by the corresponding alkyl chain bicycloheptanones listed in Preparation 5.C.3.a., the following representative substituted alkyl chain analogues are prepared:

N-[3-endo-hydroxy-2-exo-(3-hydroxy-6-ethyloct-1-yl)bicyclo[3.2.0]hept-6-ylidene]-3-aminooxypropionic acid;

N-[3-endo-hydroxy-2-exo-(3-hydroxy-3-cyclopentyl-prop-1-yl)bicyclo[3.2.0]hept-6-ylidene]-3-aminooxypropionic acid;

N-[3-endo-hydroxy-2-exo-(3-hydroxy-3-cyclohexyl-prop-1-yl)bicyclo[3.2.0]hept-6-ylidene]-3-aminooxypropionic acid;

N-[3-endo-hydroxy-2-exo-(3-hydroxy-3-phenylprop-1-yl)bicyclo[3.2.0]hept-6-ylidene]-3-aminooxypropionic acid;

N-[3-endo-hydroxy-2-exo-(3-hydroxy-3-(4-chlorophenyl)prop-1-yl)-bicyclo[3.2.0]hept-6-ylidene]-3-aminooxypropionic acid;

N-[3-endo-hydroxy-2-exo-(3-hydroxy-3-(2,4-dimethylphenyl)prop-1-yl)-bicyclo[3.2.0]hept-6-ylidene]-3-aminooxypropionic acid;

N-[3-endo-hydroxy 2-exo-(3-hydroxy-4-phenylbut-1-yl)bicyclo[3.2.0]hept-6-ylidene]-3-aminooxypropionic acid;

N-[3-endo-hydroxy-2-exo-(3-hydroxy-4-(4-methoxyphenylbut-1-yl)-bicyclo[3.2.0]hept-6-ylidene]-3-aminooxypropionic acid;

N-[3-endo-hydroxy-2-exo-(3-hydroxy-3-(3-trifluoromethylphenyl)prop-1-yl)-bicyclo[3.2.0]hept-6-ylidene]-3-aminooxypropionic acid.

EXAMPLE 4

Alkynyl Aminooxybutyric Acid of Formula (1)

A. This example illustrates a method, according to the invention, of preparing a compound of the invention, namely N-[3-endo-hydroxy-2-exo-(3-hydroxy-oct-1-ynyl)bicyclo[3.2.0)hept-6-ylidene]-4-aminooxybutyric acid (1).

1. One equivalent of 3-endo-hydroxy-2-exo-(3-hydroxy-oct-1-ynyl)bicyclo[3.2.0]heptan-6-one (VIIIA)(Preparation 5.A.1.a.) and two equivalents of sodium acetate were dissolved in 3 ml of methanol and added to the solution of one and one half equivalent of 4-aminooxybutyric acid hydrochloric acid salt dissolved in 3 ml of methanol. The reaction mixture was stirred at room temperature for one hour at which time completeness of the reaction was determined by thin layer chromatography. The residue remaining after evaporation of the solvent was extracted several times with ethyl acetate, the combined extracts washed several times with saturated aqueous salt solution, dried over magnesium sulfate, and evaporated in vacuo to furnish a solid residue of the desired product. Reprecipitation from ethyl acetate-heptane gave the pure title compound as a glass.

B. Similarly, by following the procedure of Example 4.A.1. but substituting for 3-endo-hydroxy-2-exo-(3-hydroxy-oct-1-ynyl)bicyclo[3.2.0]heptan-6-one the corresponding alkynyl bicycloheptanone isomer (A) chosen from those compounds listed in Preparation 5.A.2.a., the following compounds are obtained:

N-[3-endo-hydroxy-2-exo-(3-hydroxybut-1-ynyl)bicyclo[3.2.0]hept-6-ylidene]-4-aminooxybutyric acid;

N-[3-endo-hydroxy-2-exo-(3-hydroxypent-1-ynyl)bicyclo[3.2.0]hept-6-ylidene]-4-aminooxybutyric acid;

N-[3-endo-hydroxy-2-exo-(3-hydroxyhex-1-ynyl)bicyclo[3.2.0]hept-6-ylidene]-4-aminooxybutyric acid;

N-[3-endo-hydroxy-2-exo-(3-hydroxyhept-1-ynyl)bicyclo[3.2.0]hept-6-ylidene]-4-aminooxybutyric acid;

N-[3-endo-hydroxy-2-exo-(3-hydroxynon-1-ynyl)bicyclo[3.2.0]hept-6-ylidene]-4-aminooxybutyric acid;

N-[3-endo-hydroxy-2-exo-(3-hydroxydec-1-ynyl)bicyclo[3.2.0]hept-6-ylidene]-4-aminooxybutyric acid;

N-[3-endo-hydroxy-2-exo-(3-hydroxyundec-1-ynyl)-bicyclo-[3.2.0]hept-6-ylidene]-4-aminooxybutyric acid;

N-[3-endo-hydroxy-2-exo-(3-hydroxydodec-1-ynyl)-bicyclo[3.2.0]hept-6-ylidene]-4-aminooxybutyric acid.

C. In a similar manner by following the procedure of Example 4.A.1. but substituting for 3-endo-hydroxy-2-exo-(3-hydroxy-oct-1-ynyl)bicyclo[3.2.0]heptan-6-one the corresponding alkynylbicycloheptanones prepared according to Preparation 5.A.3.a, the following representative compounds are prepared:

N-[3-endo-hydroxy-2-exo-(3-hydroxy-6-ethyloct-1-ynyl)bicyclo[3.2.0]hept-6-ylidene]-4-aminooxybutyric acid;

N-[3-endo-hydroxy-2-exo-(3-hydroxy-3-cyclopentyl-prop-1-ynyl)-bicyclo[3.2.0]hept-6-ylidene]-4-aminooxybutyric acid;

N-[3-endo-hydroxy-2-exo-(3-hydroxy-3-cyclohexyl-prop-1-ynyl)bicyclo[3.2.0]hept-6-ylidene]-4-aminooxybutyric acid;

N-[3-endo-hydroxy-2-exo-(3-hydroxy-3-phenylprop-1-ynyl)bicyclo[3.2.0]hept-6-ylidene]-4-aminooxybutyric acid;

N-[3-endo-hydroxy-2-exo-(3-hydroxy-3-(4-chlorophenyl)prop-1-ynyl)-bicyclo[3.2.0]hept-6-ylidene]-4-aminooxybutyric acid;

N-[3-endo-hydroxy-2-exo-(3-hydroxy-3-(2,4-dimethylphenyl)prop-1-ynyl)-bicyclo[3.2.0]hept-6-ylidene]-4-aminooxybutyric acid;

N-[3-endo-hydroxy 2-exo-(3-hydroxy-4-phenylbut-1-ynyl)bicyclo[3.2.0]hept-6-ylidene]-4-aminooxybutyric acid;

N-[3-endo-hydroxy-2-exo-(3-hydroxy-4-(4-methoxyphenylbut-1-ynyl)-bicyclo[3.2.0]hept-6-ylidene]-4-aminooxybutyric acid;

N-[3-endo-hydroxy-2-exo-(3-hydroxy-3-(3-trifluoromethylphenyl)prop-1-ynyl)-bicyclo[3.2.0]hept-6-ylidene]-4-aminooxybutyric acid.

EXAMPLE 5

Alkenyl Aminooxybutryric Acid of Formula (1)

A. This example illustrates a method, according to the invention, of preparing a novel compound of the invention, namely N-[3-endo-hydroxy-2-exo-(3-hydroxyoct-1-trans-enyl)bicyclo[3.2.0]hept-6-ylidene]-4-aminooxybutyric acid. This compound is prepared by following the procedure of Example 4.A.1. but substituting 3-endo-hydroxy-2-exo-(3-hydroxy-oct-1-ynyl)-bicyclo[3.2.0]heptan-6-one by 3-endo-hydroxy-2-exo-(3-hydroxyoct-1-trans-enyl)bicyclo[3.2.0]heptan-6-one prepared according to Procedure 5.B.1.a.

B. Similarly, by following the procedure of Example 4.A.1. but substituting for 3-endo-hydroxy-2-exo-(3-hydroxy-oct-1-ynyl)bicyclo[3.2.0]heptan-6-one the corresponding alkenyl bicycloheptanones chosen from those listed in Procedure 5.B.2.a, the following compounds are prepared:

N-[3-endo-hydroxy-2-exo-(3-hydroxybut-1-trans-enyl)-bicyclo[3.2.0]hept-6-ylidene]-4-aminooxybutyric acid;

N-[3-endo-hydroxy-2-exo-(3-hydroxypent-1-trans-enyl)bicyclo[3.2.0]hept-6-ylidene]-4-aminooxybutyric acid;

N-[3-endo-hydroxy-2-exo-(3-hydroxyhex-1-trans-enyl)-bicyclo[3.2.0]hept-6-ylidene]-4-aminooxybutyric acid;

N-[3-endo-hydroxy-2-exo-(3-hydroxyhept-1-trans-enyl)bicyclo[3.2.0]hept-6-ylidene]-4-aminooxybutyric acid;

N-[3-endo-hydroxy-2-exo-(3-hydroxynon-1-trans-enyl)-bicyclo[3.2.0]hept-6-ylidene]-4-aminooxybutyric acid;

N-[3-endo-hydroxy-2-exo-(3-hydroxydec-1-trans-enyl)-bicyclo[3.2.0]hept-6-ylidene]-4-aminooxybutyric acid N-[3-endo-hydroxy-2-exo-(3-hydroxyundec-1-transenyl)bicyclo-[3.2.0]hept-6-ylidene]-4-aminooxybutyric acid;

N-[3-endo-hydroxy-2-exo-(3-hydroxydodec-1-transenyl)bicyclo-[3.2.0]hept-6-ylidene]-4-aminooxybutyric acid.

C. In a similar manner by following the procedure of Example 4.A.1. but substituting for 3-endo-hydroxy-2-exo-(3-hydroxy-oct-1-ynyl)bicyclo[3.2.0]heptan-6-one the corresponding alkenyl bicycloheptanone prepared acccording to Procedure 5.B.3.a., the following representative derivatives of 4-aminooxybutyric acid are prepared:

N-[3-endo-hydroxy-2-exo-(3-hydroxy-6-ethyloct-1-transenyl)bicyclo[3.2.0]hept-6-ylidene]-4-aminooxybutyric acid;

N-[3-endo-hydroxy-2-exo-(3-hydroxy-3-cyclopentyl-prop-1-trans-enyl)bicyclo[3.2.0]hept-6-ylidene]-4-aminooxybutyric acid;

N-[3-endo-hydroxy-2-exo-(3-hydroxy-3-cyclohexyl-prop-1-trans-enyl)bicyclo[3.2.0]hept-6-ylidene]-4-aminooxybutyric acid;

N-[3-endo-hydroxy-2-exo-(3-hydroxy-3-phenylprop-1-trans-enyl)bicyclo[3.2.0]hept-6-ylidene]-4-aminooxybutyric acid;

N-[3-endo-hydroxy-2-exo-(3-hydroxy-3-(4-chlorophenyl)prop-1-trans-enyl)-bicyclo[3.2.0]hept-6-ylidene]-4-aminooxybutyric acid;

N-[3-endo-hydroxy-2-exo-(3-hydroxy-3-(2,4-dimethylphenyl)prop-1-trans-enyl)-bicyclo[3.2.0]hept-6-ylidene]-4-aminooxybutyric acid;

N-[3-endo-hydroxy 2-exo-(3-hydroxy-4-phenylbut-1-trans-enyl)bicyclo[3.2.0]hept-6-ylidene]-4-aminooxybutyric acid;

N-[3-endo-hydroxy-2-exo-(3-hydroxy-4-(4-methoxyphenylbut-1-trans-enyl)-bicyclo[3.2.0]hept-6-ylidene]-4-aminooxybutyric acid;

N-[3-endo-hydroxy-2-exo-(3-hydroxy-3-(3-trifluoromethylphenyl)prop-1-trans-enyl)-bicyclo[3.2.0]hept-6-ylidene]-4-aminooxybutyric acid.

EXAMPLE 6

Alkyl Aminooxybutyric Acid of Formula (1)

A. This example illustrates a method, according to the invention, of preparing a novel compound of the invention, namely N-[3-endo-hydroxy-2-exo-(3-hydroxyoct-1-ynyl)bicyclo[3.2.0]hept-6-ylidene]-4-aminooxybutyric acid. This compound is prepared by following the procedure of Example 4.A.1, but substituting 3-endohydroxy-2-exo-(3-hydroxy-oct-1-ynyl)bicyclo[3.2.0]heptan-6-one by 3-endo-hydroxy-2-exo-(3-hydroxyoct-1-yl)bicyclo[3.2.0]heptan-6-one prepared according to Procedure 5.C.1.a.

B. Similarly, by following the procedure of Example 4.A.1. but substituting for 3-endo-hydroxy-2-exo-(3-hydroxy-oct-1-ynyl)bicyclo[3.2.0]heptan-6-one the corresponding alkyl chain bicycloheptanone chosen from those listed in Procedure 5.C.2.a., the following compounds are prepared:

N-[3-endo-hydroxy-2-exo-(3-hydroxybut-1-yl)-bicyclo[3.2.0]hept-6-ylidene]-4-aminooxybutyric acid;
N-[3-endo-hydroxy-2-exo-(3-hydroxypent-1-yl)-bicyclo[3.2.0]hept-6-ylidene]-4-aminooxybutyric acid;
N-[3-endo-hydroxy-2-exo-(3-hydroxyhex-1-yl)-bicyclo[3.2.0]hept-6-ylidene]-4-aminooxybutyric acid;
N-[3-endo-hydroxy-2-exo-(3-hydroxyhept-1-yl)-bicyclo[3.2.0]hept-6-ylidene]-4-aminooxybutyric acid;
N-[3-endo-hydroxy-2-exo-(3-hydroxynon-1-yl)-bicyclo[3.2.0]hept-6-ylidene]-4-aminooxybutyric acid;
N-[3-endo-hydroxy-2-exo-(3-hydroxydec-1-yl)-bicyclo[3.2.0]hept-6-ylidene]-4-aminooxybutyric acid;
N-[3-endo-hydroxy-2-exo-(3-hydroxyundec-1-yl)bicyclo[3.2.0]hept-6-ylidene]-4-aminooxybutyric acid;
N-[3-endo-hydroxy-2-exo-(3-hydroxydodec-1-yl)bicyclo[3.2.0]hept-6-ylidene]-4-aminooxybutyric acid.

C. In a similar manner by following the procedure of Example 4.A.1. but substituting for 3-endo-hydroxy-2exo-(3-hydroxy-oct-1-ynyl)bicyclo[3.2.0]heptan-6-one the corresponding alkyl side chain bicycloheptanones chosen from compounds prepared by Preparation 5.C.3.a., the following representative alkyl oxime ethers are prepared:

N-[3-endo-hydroxy-2-exo-(3-hydroxy-6-ethyloct-1-yl)bicyclo[3.2.0]hept-6-ylidene]-4-aminooxybutyric acid;
N-[3-endo-hydroxy-2-exo-(3-hydroxy-3-cyclopentylprop-1-yl)bicyclo[3.2.0]hept-6-ylidene]-4-aminooxybutyric acid;
N-[3-endo-hydroxy-2-exo-(3-hydroxy-3-cyclohexylprop-1-yl)bicyclo[3.2.0]hept-6-ylidene]-4-aminooxybutyric acid;
N-[3-endo-hydroxy-2-exo-(3-hydroxy-3-phenylprop-1-yl)bicyclo[3.2.0]hept-6-ylidene]-4-aminooxybutyric acid;
N-[3-endo-hydroxy-2-exo-(3-hydroxy-3-(4-chlorophenyl)prop-1-yl)-bicyclo[3.2.0]hept-6-ylidene]-4-aminooxybutyric acid;
N-[3-endo-hydroxy-2-exo-(3-hydroxy-3-(2,4-dimethylphenyl)prop-1-yl)-bicyclo[3.2.0]hept-6-ylidene]-4-aminooxybutyric acid;
N-[3-endo-hydroxy 2-exo-(3-hydroxy-4-phenylbut-1-yl)bicyclo[3.2.0]hept-6-ylidene]-4-aminooxybutyric acid;
N-[3-endo-hydroxy-2-exo-(3-hydroxy-4-(4-methoxyphenylbut-1-yl)-bicyclo[3.2.0]hept-6-ylidene]-4-aminooxybutyric acid; and
N-[3-endo-hydroxy-2-exo-(3-hydroxy-3-(3-trifluoromethylphenyl)prop-1-yl)-bicyclo[3.2.0]hept-6-ylidene]-4-aminooxybutyric acid.

EXAMPLE 7

Alkynyl Aminooxypropionic Acid of Formula (2)

A. This example illustrates a method, according to the invention, of preparing the novel compound of the invention having the structure N-[2-endo-hydroxy-3-exo-(3-hydroxyoct-1-ynyl) bicyclo[3.2.0]hept-6-ylidene]-3-aminooxypropionic acid (2).

1. A mixture of 80 mg of 2-endo-hydroxy-3-exo-(3-hydroxyoct-1-ynyl)bicyclo[3.2.0]heptan-6-one (VIIIB) (Preparation 5.A.1.b.) and 53 mg of sodium acetate were dissolved in 4 ml of methanol and added to a solution of 68 mg of 3-aminooxypropionic acid hydrochloric acid salt (Preparation 5) dissolved in 3 ml of methanol.

The reaction mixture was stirred at room temperature for one hour and completeness of the reaction was determined by thin layer chromatography using methylene chloride-methanol-acetic acid (97:7.5:0.5). After evaporation of the solvent the resulting residue was extracted several times with ethyl acetate, the combined extracts washed several times with saturated aqueous salt solution, dried over magnesium sulfate, and evaporated to obtain a residue of the desired 3-aminooxypropionic acid derivative. Reprecipitation from ethyl acetate-heptane furnished chromatographically pure N-[2-endo-hydroxy-3-exo-(3-hydroxyoct-1-ynyl)bicyclo[3.2.0]hept-6-ylidene]-3-aminooxypropionic acid as a glassy solid whose C.I.M.S. contained an MH+ peak at m/e 338.

A.2. Similarly, using the procedure of Example 7.A.1 and using 2-endo-hydroxy-3-exo(3α$\beta$S-hydroxyoct-1-ynyl)bicyclo[3.2.0]heptan-6-one (Preparation 10.G), one obtains N-[2-endo-hydroxy-3-exo-(3α$\beta$S-hydroxyoct-1-ynyl)bicyclo[3.2.0]hept-6-ylidene]-3-aminooxypropionic acid as a glassy solid, whose C.I.M.S. contained an MH+ peak at m/e 338 and an MNH$_4$+ peak at m/e 355.

A.3. Similarly, using the procedure of Example 7.A.1 and using 2-endo-hydroxy-3-exo(3αS-hydroxyoct-1-ynyl)bicyclo[3.2.0]heptan-6-one, one obtains N-[2-endo-hydroxy-3-exo-(3αS-hydroxyoct-1-ynyl)bicyclo[3.2.0]hept-6-ylidene]-3-aminooxypropionic acid as a glassy solid, whose C.I.M.S. contained an MH+ peak at m/e 338 and whose $[\alpha]_D$ was −136° (methanol).

B.1. Similarly, by following the procedure of Example 7.A.1. but substituting for 2-endo-hydroxy-3-exo-(3-hydroxy-oct-1-ynyl)bicyclo[3.2.0]heptan-6-one the corresponding alkynyl bicycloheptanone isomer (B) products of Preparation 5.A.2.b., the following compounds are prepared, among others:

N-[2-endo-hydroxy-3-exo-(3-hydroxybut-1-ynyl)bicyclo[3.2.0]hept-6-ylidene]-3-aminooxypropionic acid;
N-[2-endo-hydroxy-3-exo-(3-hydroxypent-1-ynyl)bicyclo[3.2.0]hept-6-ylidene]-3-aminooxypropionic acid;
N-[2-endo-hydroxy-3-exo-(3-hydroxyhex-1-ynyl)bicyclo[3.2.0]hept-6-ylidene]-3-aminooxypropionic acid;
N-[2-endo-hydroxy-3-exo-(3-hydroxyhept-1-ynyl)bicyclo[-3.2.0]hept-6-ylidene]-3-aminooxypropionic acid;
N-[2-endo-hydroxy-3-exo-(3-hydroxynon-1-ynyl)bicyclo[3.2.0]hept-6-ylidene]-3-aminooxypropionic acid;
N-[2-endo-hydroxy-3-exo-(3-hydroxydec-1-ynyl)bicyclo[3.2.0]hept-6-ylidene]-3-aminooxypropionic acid, a glass whose C.I.M.S. contains a MH+ peak at m/e 366;
N-[2-endo-hydroxy-3-exo-(3-hydroxyundec-1-ynyl)-bicyclo[3.2.0]hept-6-ylidene]-3-aminooxypropionic acid;
N-[2-endo-hydroxy-3-exo-(3-hydroxydodec-1-ynyl)-bicyclo[3.2.0]hept-6-ylidene]-3-aminooxypropionic acid.

C. In a similar manner by following the procedure of Example 7.A.1, but substituting for 2-endo-hydroxy-3-exo-(3-hydroxy-oct-1-ynyl)bicyclo[3.2.0]heptan-6-one the corresponding alkynyl bicycloheptanone isomer (B) products chosen from those listed in Preparation 5.A.3.b., the following representative oxime ethers of structure (2) are prepared:

N-[2-endo-hydroxy-3-exo-(3-hydroxy-6-ethyloct-1-ynyl)bicyclo[3.2.0]hept-6-ylidene]-3-aminooxypropionic acid;
N-[2-endo-hydroxy-3-exo-(3-hydroxy-3-cyclopentylprop-1-ynyl)bicyclo[3.2.0]hept-6-ylidene]-3-aminooxypropionic acid, whose C.I.M.S. has an MH+ peak at m/e 336;

N-[2-endo-hydroxy-3-exo-(3-hydroxy-3-cyclohexyl-prop-1-ynyl)bicyclo[3.2.0]hept-6-ylidene]-3-aminooxypropionic acid, whose C.I.M.S. has an MH+ peak at m/e 350 and MNH+ peak at m/e 367;

N-[2-endo-hydroxy-3-exo-(3-hydroxy-3-phenylprop-1-ynyl)bicyclo[3.2.0]hept-6-ylidene]-3-aminooxypropionic acid;

N-[2-endo-hydroxy-3-exo-(3-hydroxy-3-(4-chlorophenyl)prop-1-ynyl)-bicyclo[3.2.0]hept-6-ylidene]-3-aminooxypropionic acid;

N-[2-endo-hydroxy-3-exo-(3-hydroxy-3-(2,4-dimethylphenyl)prop-1-ynyl)-bicyclo[3.2.0]hept-6-ylidene]-3-aminooxypropionic acid;

N-[2-endo-hydroxy 3-exo-(3-hydroxy-4-phenylbut-1-ynyl)bicyclo[3.2.0]hept-6-ylidene]-3-aminooxypropionic acid;

N-[2-endo-hydroxy-3-exo-(3-hydroxy-4-(4-methoxyphenylbut-1-ynyl)bicyclo[3.2.0]hept-6-ylidene]-3-aminooxypropionic acid;

N-[2-endo-hydroxy-3-exo-(3-hydroxy-3-(3-trifluoromethylphenyl)prop-1-ynyl)-bicyclo[3.2.0]hept-6-ylidene]-3-aminooxypropionic acid.

EXAMPLE 8

Alkenyl Aminooxypropionic Acid of Formula (2).

A.1. This example illustrates a method, according to the invention, of preparing the compound of the formula N-[2-endo-hydroxy-3-exo-(3-hydroxy-oct-1-transenyl)bicyclo[3.2.0]hept-6-ylidene]-3-aminooxypropionic acid. This compound is prepared by following the procedure of Example 7.A.1, but substituting 2-endo-hydroxy-3-exo-(3-hydroxyoct-1-ynyl)-bicyclo[3.2.0]heptan-6-one (VIIIB) with 2-endo-hydroxy-3-exo-(3-hydroxyoct-1-trans-enyl)bicyclo[3.2.0]heptan-6-one, according to the Preparation 5.B.1.b.

A.2. Following the procedure of Example 7.A.1, but substituting 2-endo-hydroxy-3-exo-(3-hydroxyoct-1-ynyl)bicyclo[3.2.0]-heptan-6-one with 2-endo-hydroxy-3-exo-(3αS-hydroxyoct-1-trans-enyl)bicyclo[3.2.0]heptan-6-one (Preparation 12.B), one obtains N-[2-endo-hydroxy-3-exo-(3αS-hydroxyoct-1-trans-enyl)bicyclo[3.2.0]hept-6-ylidene]-3-aminooxypropionic acid, a glass whose C.I.M.S. contains an MH+ peak at m/e 340.

B. Similarly, by following the procedure of Example 7.A.1. but substituting 2-endo-hydroxy-3-exo-(3-hydroxy-oct-1-ynyl)bicyclo[3.2.0]heptan-6-one by corresponding alkenyl bicycloheptanone isomers (B) prepared according to Procedure 5.B.2.b, the following compounds are prepared:

N-[2-endo-hydroxy-3-exo-(3-hydroxy-but-1-trans-enyl)bicyclo[3.2.0]hept-6-ylidene]-3-aminooxypropionic acid;

N-[2-endo-hydroxy-3-exo-(3-hydroxy-pent-1-trans-enyl)bicyclo[3.2.0]hept-6-ylidene]-3-aminooxypropionic acid;

N-[2-endo-hydroxy-3-exo-(3-hydroxy-hex-1-trans-enyl)bicyclo[3.2.0]hept-6-ylidene]-3-aminooxypropionic acid;

N-[2-endo-hydroxy-3-exo-(3-hydroxy-hept-1-trans-enyl)bicyclo[3.2.0]hept-6-ylidene]-3-aminooxypropionic acid;

N-[2-endo-hydroxy-3-exo-(3-hydroxy-non-1-trans-enyl)bicyclo[3.2.0]hept-6-ylidene]-3-aminooxypropionic acid;

N-[2-endo-hydroxy-3-exo-(3-hydroxy-dec-1-trans-enyl)bicyclo[3.2.0]hept-6-ylidene]-3-aminooxypropionic acid;

N-[2-endo-hydroxy-3-exo-(3-hydroxy-undec-1-trans-enyl)bicyclo-[3.2.0]hept-6-ylidene]-3-aminooxypropionic acid;

N-[2-endo-hydroxy-3-exo-(3-hydroxy-dodec-1-trans-enyl)bicyclo-[3.2.0]hept-6-ylidene]-3-aminooxypropionic acid.

C.1. In a similar manner by following the procedure of Example 7.A.1, but substituting 2-endo-hydroxy-3-exo(3-hydroxy-oct-1-ynyl)bicyclo[3.2.0]heptan-6-one by corresponding alkenyl bicycloheptanone chosen from those listed in the Preparation 5.B.3.b, the following representative compounds are prepared:

N-[2-endo-hydroxy-3-exo-(3-hydroxy-6-ethyloct-1-transenyl)bicyclo[3.2.0]hept-6-ylidene]-3-aminooxypropionic acid;

N-[2-endo-hydroxy-3-exo-(3-hydroxy-3-cyclopentylprop-1-trans-enyl)bicyclo[3.2.0]hept-6-ylidene]-3-aminooxypropio nic acid, whose C.I.M.S. contained an MH+ peak at m/e 338;

N-[2-endo-hydroxy-3-exo-(3-hydroxy-3-cyclohexylprop-1-trans-enyl)bicyclo[3.2.0]hept-6-ylidene]-3-aminooxypropionic acid, whose C.I.M.S. contained an MH+ peak at m/e 352 and an MNH4+ peak at m/e 369;

N-[2-endo-hydroxy-3-exo-(3-hydroxy-3-phenylprop-1-trans-enyl)bicyclo[3.2.0]hept-6-ylidene]-3-aminooxypropionic acid;

N-[2-endo-hydroxy-3-exo-(3-hydroxy-3-(4-chlorophenyl)prop-1-trans-enyl)-bicyclo[3.2.0]hept-6-ylidene]-3-aminooxypropionic acid;

N-[2endo-hydroxy-3-exo-(3-hydroxy-3-(2,4-dimethylphenyl)prop-1-trans-enyl)-bicyclo[3.2.0]hept-6-ylidene]-3-aminooxypropionic acid;

N-[2-endo-hydroxy 3-exo-(3-hydroxy-4-phenylbut-1-trans-enyl)-bicyclo[3.2.0]hept-6-ylidene]-3-aminooxypropionic acid;

N-[2-endo-hydroxy-3-exo-(3-hydroxy-4-(4-methoxyphenylbut)prop-1-trans-enyl)-bicyclo[3.2.0]hept-6-ylidene]3-aminooxypropionic acid;

N-[2-endo-hydroxy-3-exo-(3-hydroxy-3-(3-trifluoromethylphenyl)prop-1-trans-enyl)-bicyclo[3.2.0]hept-6-ylidene]-3-aminooxypropionic acid.

EXAMPLE 9

Alkyl Aminooxypropionic Acid of Formula (2)

A. This example illustrates a method, according to the invention, of preparing the compound of the formula N-[2-endo-hydroxy-3-exo-(3-hydroxy-oct-1-yl)-bicyclo[3.2.0]hept-6-ylidene]-3-aminooxypropionic acid.

This compound is prepared by following the procedure of Example 7.A.1, but substituting 2-endo-hydroxy-3-exo-(3-hydroxy-oct-1-ynyl)bicyclo[3.2.0-]heptan-6-one (VIIIB) with 2-endo-hydroxy-3-exo-(3-hydroxy-oct-1-yl)bicyclo-[3.2.0]heptan-6-one prepared according to Procedure 5.C.1.b, a glass whose C.I.M.S. contained an MH+ peak at m/e 342.

B. Similarly, by following the procedure of Example 7.A.1. but substituting 2-endo-hydroxy- 3-exo(3-hydroxy-oct-1-ynyl)bicyclo-[3.2.0]heptan-6-one by the corresponding alkyl bicycloheptanone chosen from those listed in Preparation 5.C.2.b, the following compounds are prepared:

N-[2-endo-hydroxy-3-exo-(3-hydroxy-but-1-yl)bicyclo-[3.2.0]hept-6-ylidene]-3-aminooxypropionic acid;

N-[2-endo-hydroxy-3-exo-(3-hydroxy-pent-1-yl)bicyclo-[3.2.0]hept-6-ylidene]-3-aminooxypropionic acid;
N-[2-endo-hydroxy-3-exo-(3-hydroxy-hex-1-yl)bicyclo-[3.2.0]hept-6-ylidene]-3-aminooxypropionic acid;
N-[2-endo-hydroxy-3-exo-(3-hydroxy-hept-1-yl)bicyclo-[3.2.0]hept-6-ylidene]-3-aminooxypropionic acid;
N-[2-endo-hydroxy-3-exo-(3-hydroxy-non-1-yl)bicyclo-[3.2.0]hept-6-ylidene]-3-aminooxypropionic acid;
N-[2-endo-hydroxy-3-exo-(3-hydroxy-dec-1-yl)bicyclo-[3.2.0]hept-6-ylidene]-3-aminooxypropionic acid, a glass whose C.I.M.S. contained an MH+ peak at m/e 370;
N-[2-endo-hydroxy-3-exo-(3-hydroxy-undec-1-yl)bicyclo-[3.2.0]hept-6-ylidene]-3-aminooxypropionic acid;
N-[2-endo-hydroxy-3-exo-(3-hydroxy-dodec-1-yl)bicyclo-[3.2.0]hept-6-ylidene]-3-aminooxypropionic acid.

C. In a similar manner by following the procedure of Example 7.A.1. but substituting 2-endo-hydroxy-3-exo(3-hydroxy-oct-1-yl)bicyclo-[3.2.0]heptan-6-one by the corresponding alkyl bicycloheptanones listed in the Preparation 5.C.3.b. the following representative compounds are prepared:
N-[2-endo-hydroxy-3-exo-(3-hydroxy-6-ethyloct-1-yl)bicyclo[3.2.0]hept-6-ylidene]-3-aminooxypropionic acid;
N-[2-endo-hydroxy-3-exo-(3-hydroxy-3-cyclopentyl-prop-1-yl)bicyclo[3.2.0]hept-6-ylidene]-3-aminooxypropionic acid, a glass whose C.I.M.S. contained an MH+ peak at m/e 340;
N-[2-end-hydroxy-3-exo-(3-hydroxy-3-cyclohexylprop-1-yl)bicyclo[3.2.0]hept-6-ylidene]-3-aminooxypropionic acid, a glass whose C.I.M.S. contained an MH+ peak at m/e 354;
N-[2-endo-hydroxy-3-exo-(3-hydroxy-3-phenylprop-1-yl)bicyclo[3.2.0]hept-6-ylidene]-3-aminooxypropionic acid;
N-[2-endo-hydroxy-3-exo-(3-hydroxy-3-(4-chlorophenyl)prop-1-yl)-bicyclo[3.2.0]hept-6-ylidene]3-aminooxypropionic acid;
N-[2-endo-hydroxy-3-exo-(3-hydroxy-3-(2,4-dimethylphenyl)prop-1-yl)-bicyclo[3.2.0]hept-6-ylidene]-3-aminooxypropionic acid;
N-[2-endo-hydroxy 3-exo-(3-hydroxy-4-phenylbut1-yl)-bicyclo[3.2.0]hept-6-ylidene]-3-aminooxypropionic acid;
N-[2-endo-hydroxy-3-exo-(3-hydroxy-3-(3-trifluoromethylphenyl)prop-1-yl)-bicyclo[3.2.0]hept-6-ylidene]-3-aminooxypropionic acid;
N-[2-endo-hydroxy-3-exo-(3-hydroxy-4-(4-methoxyphenylbut-1-yl)-bicyclo[3.2.0]hept-6-ylidene]-3-aminooxypropionic acid.

EXAMPLE 10

Alkynyl Aminooxybutyric Acid of Formula (2)

A. This example illustrates a method, according to the invention, of preparing the compound of the formula (2), N-[2-endo-hydroxy-3-exo-(3-hydroxy-oct-1-ynyl)bicyclo[3.2.0]hept-6-ylidene]-4-aminooxybutyric acid.

1. 0.32 mmole of 2-endo-hydroxy-3-exo(3-hydroxy-oct-1-ynyl)bicyclo[3.2.0]heptan-6-one (VIIB)(Preparation 5.A.1.b.) and 0.64 mmole of sodium acetate were dissolved in 3 ml of methanol and added to a solution of 0.48 mmole of 4-aminooxybutyric acid hydrochloric acid salt (Preparation 6) in 3 ml of methanol. The reaction mixture was stirred at room temperature for one hour and completeness of the reaction was determined by thin layer chromatography. The solvent was evaporated from the reaction mixture. The residue was extracted several times with ethyl acetate, the combined extracts were washed several times with saturated aqueous salt solution, dried over magnesium sulfate and evaporated in vacuo to provide a crystalline residue of the desired product. Recrystallization from ethyl acetate-heptane furnished pure crystalline N-[2-endo-hydroxy-3-exo(3-hydroxy-oct-1-ynyl)-bicyclo-[3.2.0)hept-6-ylidene]-4-aminooxybutyric acid, m.p. 82–84° C.

B. Similarly, by following the procedure of Example 10.A.1, but substituting 2-endo-hydroxy-3-exo(3-hydroxy-oct-1-ynyl)bicyclo[3.2.0]heptan-6-one by the corresponding alkynyl bicycloheptanones prepared according to Preparation 5.A.2.b., the following compounds are prepared:
N-[2-endo-hydroxy-3-exo-(3-hydroxy-but-1-ynyl)bicyclo[3.2.0]hept-6-ylidene]-4-aminooxybutyric acid;
N-[2-endo-hydroxy-3-exo-(3-hydroxy-pent-1-ynyl)-bicyclo[3.2.0]hept-6-ylidene]-4-aminooxybutyric acid;
N-[2-endo-hydroxy-3-exo-(3-hydroxy-hex-1-ynyl)bicyclo[3.2.0]hept-6-ylidene]-4-aminooxybutyric acid;
N-[2-endo-hydroxy-3-exo-(3-hydroxy-hept-1-ynyl)-bicyclo[3.2.0]hept-6-ylidene]-4-aminooxybutyric acid;
N-[2-endo-hydroxy-3-exo-(3-hydroxy-non-1-ynyl)bicyclo[3.2.0]hept-6-ylidene]-4-aminooxybutyric acid;
N-[2-endo-hydroxy-3-exo-(3-hydroxy-dec-1-ynyl)bicyclo[3.2.0]hept-6-ylidene]-4-aminooxybutyric acid;
N-[2-endo-hydroxy-3-exo-(3-hydroxy-undec-1-ynyl)-bicyclo-[3.2.0]hept-6-ylidene]-4-aminooxybutyric acid;
N-[2-endo-hydroxy-3-exo-(3-hydroxy-dodec-1-ynyl)-bicyclo-[3.2.0]hept-6-ylidene]-4-aminooxybutyric acid.

C. In a similar manner by following the procedure of Example 10.A.1, but substituting 2-endo-hydroxy-3-exo(3-hydroxy-oct-1-ynyl)bicyclo[3.2.0]heptan-6-one by corresponding alkynyl bicycloheptanones chosen from those described in Preparation 5.A.3.b, the following representative compounds are prepared:
N-[2-endo-hydroxy-3-exo-(3-hydroxy-6-ethyloct-1-ynyl)bicyclo[3.2.0]hept-6-ylidene]-4-aminooxybutyric acid;
N-[2-endo-hydroxy-3-exo-(3-hydroxy-3-cyclopentyl-prop-1-ynyl)-bicyclo[3.2.0]hept-6-ylidene]-4-aminooxybutyric acid;
N-[2-endo-hydroxy-3-exo-(3-hydroxy-3-cyclohexyl-prop-1-ynyl)bicyclo[3.2.0]hept-6-ylidene]-4-aminooxybutyric acid;
N-[2-endo-hydroxy-3-exo-(3-hydroxy-3-phenylprop-1-ynyl)bicyclo[3.2.0]hept-6-ylidene]-4-aminooxybutyric acid;
N-[2-endo-hydroxy-3-exo-(3-hydroxy-3-(4-chlorophenyl)prop-1-ynyl)-bicyclo[3.2.0]hept-6-ylidene]4-aminooxybutyric acid;
N-[2-endo-hydroxy-3-exo-(3-hydroxy-3-(2,4-dimethylphenyl)prop-1-ynyl)-bicyclo[3.2.0]hept-6-ylidene]-4-aminooxybutyric acid;
N-[2-endo-hydroxy 3-exo-(3-hydroxy-phenylbut-1-ynyl)bicyclo[3.2.0]hept-6-ylidene]-4-aminooxybutyric acid;
N-[2-endo-hydroxy-3-exo-(3-hydroxy-4-(4-methoxyphenylbut-1-ynyl)-bicyclo[3.2.0]hept-6-ylidene]-4-aminooxybutyric acid;

N-[2-endo-hydroxy-3-exo-(3-hydroxy-3-(3-trifluoromethylphenyl)prop-1-ynyl)-bicyclo[3.2.0]hept-6-ylidene]-4-aminooxybutyric acid.

EXAMPLE 11

Alkenyl Aminooxybutyric Acid of Formula (2)

A. This example illustrates a method, according to the invention, of preparing compounds of the formula N-[2-endo-nydroxy-3-exo-(3-hydroxy-oct-1-trans-enyl) bicyclo[3.2.0]hept-6-ylidene]-4-aminooxybutyric acid. This compound is prepared by following the procedure of Example 10.A.1, but substituting 2-endo-hydroxy-3-exo(3-hydroxy-oct-1-ynyl)bicyclo[3.2.0]heptan-6-one with 2-endo-hydroxy-3-exo-(3-hydroxy-oct-1-trans-enyl) bicyclo[3.2.0]heptan-6-one prepared according to the Procedure 5.B.1.b.

B. Similarly, by following the procedure of Example 10.A.1, but substituting 2-endo-hydroxy-3-exo(3-hydroxy-oct-1-ynyl)bicyclo[3.2.0]heptan-6-one by corresponding alkenyl bicycloheptanones according to Procedure 5.B.2.b, the following compounds are prepared:

N-[2-endo-hydroxy-3-exo-(3-hydroxy-but-1-trans-enyl)bicyclo[3.2.0]hept-6-ylidene]-4-aminooxybutyric acid;

N-[2-endo-hydroxy-3-exo-(3-hydroxy-pent-1-trans-enyl)bicyclo[3.2.0]hept-6-ylidene]-4-aminooxybutyric acid;

N-[2-endo-hydroxy-3-exo-(3-hydroxy-hex-1-trans-enyl)bicyclo[3.2.0]hept-6-ylidene]-4-aminooxybutyric acid;

N-[2-endo-hydroxy-3-exo-(3-hydroxy-hept-1-trans-enyl)bicyclo[3.2.0]hept-6-ylidene]-4-aminooxybutyric acid;

N-[2-endo-hydroxy-3-exo-(3-hydroxy-non-1-trans-enyl)bicyclo[3.2.0]hept-6-ylidene]-4-aminooxybutyric acid;

N-[2-endo-hydroxy-3-exo-(3-hydroxy-dec-1-trans-enyl)bicyclo[3.2.0]hept-6-ylidene]-4-aminooxybutyric acid;

N-[2-endo-hydroxy-3-exo-(3-hydroxy-undec-1-transenyl)bicyclo-[3.2.0]hept-6-ylidene]-4-aminooxybutyric acid;

N-[2-endo-hydroxy-3-exo-(3-hydroxy-dodec-1-transenyl)bicyclo-[3.2.0]hept-6-ylidene]-4-aminooxybutyric acid.

C. In a similar manner by following the procedure of Example 10.A.1. but substituting 2-endo-hydroxy-3-exo-(3-hydroxy-oct-1-ynyl)bicyclo[3.2.0]heptan-6-one by corresponding alkenyl bicycloheptanones according to Preparation 5.B.3.b, the following representative compounds are prepared:

N-[2-endo-hydroxy-3-exo-(3-hydroxy-6-ethyloct-1-transenyl)bicyclo[3.2.0]hept-6-ylidene]-4-aminooxybutyric acid;

N-[2-endo-hydroxy-3-exo-(3-hydroxy-3-cyclopentylprop-1-trans-enyl)bicyclo[3.2.0]hept-6-ylidene]-4-aminooxybutyric acid;

N-[2-endo-hydroxy-3-exo-(3-hydroxy-3-cyclohexylprop-1-trans-enyl)bicyclo[3.2.0]hept-6-ylidene]-4-aminooxybutyric acid;

N-[2-endo-hydroxy-3-exo-(3-hydroxy-3-phenylprop-1-trans-enyl)bicyclo[3.2.0]hept-6-ylidene]-4-aminooxybutyric acid;

N-[2-endo-hydroxy-3-exo-(3-hydroxy-3-(4-chlorophenyl)prop-1-trans-enyl)-bicyclo[3.2.0]hept-6-ylidene]-4-aminooxybutyric acid;

N-[2-endo-hydroxy-3-exo-(3-hydroxy-3-(2,4-dimethylphenyl)prop-1-trans-enyl)-bicyclo[3.2.0]hept-6-ylidene]-4-aminooxybutyric acid;

N-[2-endo-hydroxy 3-exo-(3-hydroxy-4-phenylbut1-trans-enyl)-bicyclo[3.2.0]hept-6-ylidene]-4-aminooxybutyric acid;

N-[2-endo-hydroxy-3-exo-(3-hydroxy-4-(4-methoxyphenylbut-1-trans-enyl)-bicyclo[3.2.0]hept-6-ylidene]-4aminooxybutyric acid;

N-[2-endo-hydroxy-3-exo-(3-hydroxy-3-(3-trifluoromethylphenyl)prop-1-trans-enyl)-bicyclo[3.2.0]hept- 6-ylidene]-4-aminooxybutyric acid.

EXAMPLE 12

Alkyl Aminooxybutyric Acid of Formula (2)

A. This example illustrates a method, according to the invention, of a preparing compound of the formula N-[2-endo-hydroxy-3-exo-(3-hydroxy-oct-1-yl)bicyclo[3.2.0)hept-6-ylidene]-4 aminooxybutyric acid. This compound is prepared by following the procedure of Example 10.A.1, but substituting 2-endo-hydroxy-3-exo(3-hydroxy-oct-1-ynyl)bicyclo[3.2.0]heptan-6-one with 2-endo-hydroxy-3-exo-(3-hydroxy-oct-1-yl)bicyclo [3.2.0]heptan-6-one prepared according to the Procedure 5.C.1.b.

B. Similarly, by following the procedure of Example 10.A.1, but substituting 2-endo-hydroxy-3-exo(3-hydroxy-oct-1-yl)bicyclo[3.2.0]heptan-6-one by the corresponding alkyl bicycloheptanone listed in Preparation 5.C.2.b, the following compounds are prepared:

N-[2-endo-hydroxy-3-exo-(3-hydroxy-but-1-yl)bicyclo[3.2.0]hept-6-ylidene]-4-aminooxybutyric acid;

N-[2-endo-hydroxy-3-exo-(3-hydroxy-pent-1-yl)bicyclo[3.2.0]hept-6-ylidene]-4-aminooxybutyric acid;

N-[2-endo-hydroxy-3-exo-(3-hydroxy-hex-1-yl)bicyclo[3.2.0]hept-6-ylidene]-4-aminooxybutyric acid;

N-[2-endo-hydroxy-3-exo-(3-hydroxy-hept-1-yl)bicyclo[3.2.0]hept-6-ylidene]-4-aminooxybutyric acid;

N-[2-endo-hydroxy-3-exo-(3-hydroxy-non-1-yl)bicyclo[3.2.0]hept-6-ylidene]-4-aminooxybutyric acid;

N-[2-endo-hydroxy-3-exo-(3-hydroxy-dec-1-yl)bicyclo[3.2.0]hept-6-ylidene]-4-aminooxybutyric acid;

N-[2-endo-hydroxy-3-exo-(3-hydroxy-undec-1-yl)bicyclo[3.2.0]hept-6-ylidene]-4-aminooxybutyric acid;

N-[2-endo-hydroxy-3-exo-(3-hydroxy-dodec-1-yl)bicyclo[3.2.0]hept-6-ylidene]-4-aminooxybutyric acid;

C. In a similar manner by following the procedure of Example 10.A.1, but substituting 2-endo-hydroxy-3-exo(3-hydroxy-oct-1-ynyl)bicyclo[3.2.0]heptan-6-one by the corresponding alkyl bicycloheptanone chosen from compounds listed in Preparation 5.C.3.b the following representative compounds are prepared:

N-[2-endo-hydroxy-3-exo-(3-hydroxy-6-ethyloct-1-yl)bicyclo[3.2.0]hept-6-ylidene]-4-aminooxybutyric acid;

N-[2-endo-hydroxy-3-exo-(3-hydroxy-3-cyclopentylprop-1-yl)bicyclo[3.2.0]hept-6-ylidene]-4-aminooxybutyric acid;

N-[2-endo-hydroxy-3-exo-(3-hydroxy-3-cyclohexylprop-1-yl)bicyclo[3.2.0]hept-6-ylidene]-4-aminooxybutyric acid;

N-[2-endo-hydroxy-3-exo-(3-hydroxy-3-phenylprop-1-yl)bicyclo[3.2.0]hept-6-ylidene]-4-aminooxybutyric acid;

N-[2-endo-hydroxy-3-exo-(3-hydroxy-3-(4-chlorophenyl)-prop-oct-1-yl)-bicyclo[3.2.0]hept-6-ylidene]-4-aminooxybutyric acid;

N-[2-endo-hydroxy-3-exo-(3-hydroxy-3-(2,4-dimethylphenyl)prop-1-yl)-bicyclo[3.2.0]hept-6-ylidene]-4-aminooxybutyric acid;

N-[2-endo-hydroxy 3-exo-(3-hydroxy-4-phenylbut-1-yl)-bicyclo[3.2.0]hept-6-ylidene]-4-aminooxybutyric acid;

N-[2-endo-hydroxy-3-exo-(3-hydroxy-4-(4-methoxyphenylbut-1-yl)-bicyclo[3.2.0]hept-6-ylidene]-4-aminooxybutyric acid;

N-[2-endo-hydroxy-3-exo-(3-hydroxy-3-(3-trifluoromethylphenyl)prop-1-yl)-bicyclo[3.2.0]hept-6-ylidene]-b 4-aminooxybutyric acid.

EXAMPLE 13

Alkynyl Aminooxyacetic acid of Formula (1) A. This example illustrates the preparation of a compound of our invention encompassed by formula (1), namely N-3-endo-hydroxy-2-exo-(3-hydroxyoct-1-ynyl)bicyclo[3.2.0]nept-6-ylidene]-aminooxyacetic acid.

1. To a solution of octynyl bicycloheptanone VI (0.075 g) and sodium acetate (0.031 g) in 3 ml MeOH is added 0.05 g of carboxymethoxyamine hemihydrochloride, and the mixture is stirred at room temperature until TLC indicates essentially complete reaction (1.5 hours). The solvent is removed under reduced pressure and the resulting residue is extracted several times with ethyl acetate. The combined extracts are washed with saturated brine, dried over sodium sulfate and evaporated to furnish a residue of crude oximino acid. Preparative chromatography employing an eluant of 90% $CH_2Cl_2$, 9.7% $CH_3OH$ and 0.3% HOAc furnishes, from the appropriate fractions, the pure oximino acid as a glass exhibiting the anticipated spectral characteristics for the title structure. Chemical ionization mass spectroscopy (C.I.M.S.) furnishes a parent peak (MH+) at m/e 324.

B. Similarly, by following the procedure of Example 13.A.1, but substituting for 3-endo-hydroxy-2-exo(3-hydroxy-oct-1-ynyl)bicyclo[3.2.0]heptan-6-one the corresponding alkynyl bicycloheptanone chosen from compounds prepared in Preparation 5.A.2.a, the following compounds are prepared:

N-3-endo-hydroxy-2-exo-(3-hydroxybut-1-ynyl)bicyclo[3.2.0]hept-6-ylidene]-aminooxyacetic acid;

N-3-endo-hydroxy-2-exo-(3-hydroxypent-1-ynyl)bicyclo[3.2.0]hept-6-ylidene]-aminooxyacetic acid;

N-3-endo-hydroxy-2-exo-(3-hydroxyhex-1-ynyl)bicyclo[3.2.0]hept-6-ylidene]-aminooxyacetic acid;

N-3-endo-hydroxy-2-exo-(3-hydroxyhept-1-ynyl)bicyclo[3.2.0]hept-6-ylidene]-aminooxyacetic acid;

N-3-endo-hydroxy-2-exo-(3-hydroxynon-1-ynyl)bicyclo[3.2.0]hept-6-ylidene]-aminooxyacetic acid;

N-3-endo-hydroxy-2-exo-(3-hydroxydec-1-ynyl)bicyclo[3.2.0]hept-6-ylidene]-aminooxyacetic acid;

N-3-endo-hydroxy-2-exo-(3-hydroxyundec-1-ynyl)-bicyclo-[3.2.0]hept-6-ylidene]-aminooxyacetic acid;

N-3-endo-hydroxy-2-exo-(3-hydroxydodec-1-ynyl)-bicyclo-[3.2.0]hept-6-ylidene]-aminooxyacetic acid;

C. In a similar manner by following the procedure of Example 1.A.1, but substituting for 3-endo-hydroxy-2-exo-(3-hydroxy-oct-1-ynyl)bicyclo[3.2.0]heptan-6-one the corresponding alkynyl bicycloheptanone isomer (A) chosen from those described in Preparation 5.A.3.a, the following representative compounds are prepared:

N-3-endo-hydroxy-2-exo-(3-hydroxy-6-ethyloct-1-ynyl)bicyclo[3.2.0]hept-6-ylidene]-aminooxyacetic acid;

N-3-endo-hydroxy-2-exo-(3-hydroxy-3-cyclopentylprop-1-ynyl)-bicyclo[3.2.0]hept-6-ylidene]-aminooxyacetic acid;

N-3-endo-hydroxy-2-exo-(3-hydroxy-3-cyclohexylprop--ynyl) bicyclo[3.2.0]hept-6-ylidene]-aminooxyacetic acid;

N-3-endo-hydroxy-2-exo-(3-hydroxy-3-phenylprop-1-ynyl)bicyclo[3.2.0]hept-6-ylidene]-aminooxyacetic acid;

N-3-endo-hydroxy-2-exo-(3-hydroxy-3-(4-chlorophenyl)prop-oct-1-ynyl)-bicyclo[3.2.0]hept-6-ylidene]aminooxyacetic acid;

N-3-endo-hydroxy-2-exo-(3-hydroxy-3-(2,4-dimethylphenyl)prop-1-ynyl)-bicyclo[3.2.0]hept-6-ylidene]-aminooxyacetic acid;

N-3-endo-hydroxy-2-exo-(3-hydroxy-(4-phenylbut-1-ynyl)bicyclo[3.2.0]hept-6-ylidene]-aminooxyacetic acid;

N-3-endo-hydroxy-2-exo-(3-hydroxy-4-(4-methoxyphenylbut-1-ynyl)-bicyclo[3.2.0]hept-6-ylidene]-aminooxyacetic acid;

N-3-endo-hydroxy-2-exo-(3-hydroxy-3-(3-trifluoromethylphenyl)prop-1-ynyl)-bicyclo[3.2.0]hept-6-ylidene]aminooxyacetic acid.

EXAMPLE 14

Alkenyl Aminooxyacetic Acid of Formula (1)

A. This example illustrates a method, according to the invention, of preparing the compound of the formula N-3-endo-hydroxy-2-exo-(3-hydroxy-oct-1-transenyl)-bicyclo[3.2.0]hept-6-ylidene]-aminooxyacetic acid. This compound is prepared by following the procedure of Example 13.A.1, but substituting 3-endo-hydroxy-2-exo(3-hydroxy-oct-1-ynyl)bicyclo[3.2.0-]heptan-6-one with 3-endo-hydroxy-2-exo-(3-hydroxy-oct-1-trans-enyl)bicyclo[3.2.0]heptan-6-one prepared according to Preparation 5.B.1.a.

B. Similarly, by following the procedure of Example 13.A.1, but substituting 3-endo-hydroxy-2-exo(3-hydroxy-oct-1-ynyl)bicyclo[3.2.0]heptan-6-one by the corresponding alkenyl bicycloheptanone wherein alkenyl is chosen from those prepared according to Preparation 5.B.2.a, the following compounds are prepared N-3-endo-hydroxy-2-exo-(3-hydroxybut-1-trans-enyl)-bicyclo[3.2.0]hept-6-ylidene]-aminooxyacetic acid;

N-3-endo-hydroxy-2-exo-(3-hydroxypent-1-trans-enyl)-bicyclo[3.2.0]hept-6-ylidene]-aminooxyacetic acid;

N-3-endo-hydroxy-2-exo-(3-hydroxyhex-1-trans-enyl)-bicyclo[3.2.0]hept-6-ylidene]-aminooxyacetic acid;

N-3-endo-hydroxy-2-exo-(3-hydroxyhept-1-trans-enyl)-bicyclo[3.2.0]hept-6-ylidene]-aminooxyacetic acid;

N-3-endo-hydroxy-2-exo-(3-hydroxynon-1-trans-enyl)-bicyclo[3.2.0]hept-6-ylidene]-aminooxyacetic acid;

N-3-endo-hydroxy-2-exo-(3-hydroxydec-1-trans-enyl)-bicyclo[3.2.0]hept-6-ylidene]-aminooxyacetic acid;

N-3-endo-hydroxy-2-exo-(3-hydroxyundec-1-transenyl)bicyclo-[3.2.0]hept-6-ylidene]-aminooxyacetic acid;

N-3-endo-hydroxy-2-exo-(3-hydroxydodec-1-transenyl)bicyclo-[3.2.0]hept-6-ylidene]-aminooxyacetic acid; of Example 13.A.1, but substituting 3-endo-hydroxy-2-exo(3-hydroxy-oct-1-ynyl)bicyclo[3.2.0-]heptan-6-one by corresponding alkenyl bicycloheptanone as illustrated in Preparation 5.B.3.a, the following representative compounds are prepared:

N-3-endo-hydroxy-2-exo-(3-hydroxy-6-ethyloct-1-transenyl)bicyclo[3.2.0]hept-6-ylidene]-aminooxyacetic acid;

N-3-endo-hydroxy-2-exo-(3-hydroxy-3-cyclopentylprop-1-trans-enyl)bicyclo[3.2.0]hept-6-ylidene]-aminooxyacetic acid;

N-3-endo-hydroxy-2-exo-(3-hydroxy-3-cyclohexylprop-1-trans-enyl)bicyclo[3.2.0]hept-6-ylidene]-aminooxyacetic acid;

N-3-endo-hydroxy-2-exo-(3-hydroxy-3-phenylprop-1-trans-enyl)bicyclo[3.2.0]hept-6-ylidene]-3-aminooxypropionic acid;

N-3-endo-hydroxy-2-exo-(3-hydroxy-3-(4-chlorophenyl)prop-1-trans-enyl)-bicyclo[3.2.0]hept-6-ylidene]aminooxyacetic acid;

N-3-endo-hydroxy-2-exo-(3-hydroxy-3-(2,4-dimethylphenyl)prop-1-trans-enyl)-bicyclo[3.2.0]hept-6-ylidene]-3-aminooxypropionic acid;

N-3-endo-hydroxy-2-exo-(3-hydroxy-4-phenylbut-1-trans-enyl)bicyclo[3.2.0]hept-6-ylidene]-aminooxyacetic acid;

N-3-endo-hydroxy-2-exo-(3-hydroxy-4-(4-methoxyphenylbut-1-trans-enyl)-bicyclo[3.2.0]hept-6-ylidene]aminooxyacetic acid; and N-3-endo-hydroxy-2-exo-(3-hydroxy-3-(3-trifluoromethylphenyl)prop-1-trans-enyl)-bicyclo[3.2.0]hept-6-ylidene]-aminooxyacetic acid.

EXAMPLE 15

Alkyl Aminooxyacetic Acid of Formula (61)

A. This example illustrates a method, according to the invention, of preparing the compound having the formula N-3-endo-hydroxy-2-exo-(3-hydroxy-oct-1-yl)bicyclo[3.2.0]hept-6-ylidene]-aminooxyacetic acid. This compound is prepared by following the procedure of Example 13.A.1, but substituting for 3-endo-hydroxy-2-exo(3-hydroxy-oct-1-ynyl)bicyclo[3.2.0]heptan-6-one the 3-endo-hydroxy-2-exo-(3-hydroxy-oct-1-yl)bicyclo[3.2.0]heptan-6-one according to the Preparation 5.C.1.a.

B. Similarly, by following the procedure of Example 13.A.1, but substituting for 3-endo-hydroxy-2-exo(3-hydroxy-oct-1-yl)bicyclo[3.2.0]heptan-6-one the corresponding alkyl bicycloheptanones listed in Preparation 5.C.2.a, the following compounds are prepared:

N-3-endo-hydroxy-2-exo-(3-hydroxybut-1-yl)-bicyclo[3.2.0]hept-6-ylidene]-aminooxyacetic acid;

N-3-endo-hydroxy-2-exo-(3-hydroxypent-1-yl)-bicyclo[3.2.0]hept-6-ylidene]-aminooxyacetic acid;

N-3-endo-hydroxy-2-exo-(3-hydroxyhex-1-yl)-bicyclo[3.2.0]hept-6-ylidene]-aminooxyacetic acid;

N-3-endo-hydroxy-2-exo-(3-hydroxyhept-1-yl)-bicyclo[3.2.0]hept-6-ylidene]-aminooxyacetic acid;

N-3-endo-hydroxy-2-exo-(3-hydroxynon-1-yl)bicyclo[3.2.0]hept-6-ylidene]-aminooxyacetic acid;

N-3-endo-hydroxy-2-exo-(3-hydroxydec-1-yl)bicyclo[3.2.0]hept-6-ylidene]-aminooxyacetic acid;

N-3-endo-hydroxy-2-exo-(3-hydroxyundec-1-yl)bicyclo[3.2.0]hept-6-ylidene]-aminooxyacetic acid;

N-3-endo-hydroxy-2-exo-(3-hydroxydodec-1-yl)bicyclo[3.2.0]hept-6-ylidene]-aminooxyacetic acid; C. In a similar manner by following the procedure of Example 13.A.1, but substituting 3-endo-hydroxy-2-exo(3-hydroxy-oct-1-ynyl)bicyclo[3.2.0]heptan-6-one by corresponding alkyl bicycloheptanones listed in Preparation 5.C.3.a, the following representative compounds are prepared:

N-3-endo-hydroxy-2-exo-(3-hydroxy-6-ethyloct-1-yl)bicyclo[3.2.0]hept-6-ylidene]-aminooxyacetic acid;

N-3-endo-hydroxy-2-exo-(3-hydroxy-3-cyclopentylprop-1-yl)bicyclo[3.2.0]hept-6-ylidene]-aminooxyacetic acid;

N-3-endo-hydroxy-2-exo-(3-hydroxy-3-cyclohexylprop-1-yl)bicyclo[3.2.0]hept-6-ylidene]-aminooxyacetic acid;

N-3-endo-hydroxy-2-exo-(3-hydroxy-3-phenylprop-1-yl)-bicyclo[3.2.0]hept-6-ylidene]-aminooxyacetic acid;

N-3-endo-hydroxy-2-exo-(3-hydroxy-3-(4-chlorophenyl)-prop-oct-1-yl)-bicyclo[3.2.0]hept-6-ylidene]-aminooxyacetic acid;

N-3-endo-hydroxy-2-exo-(3-hydroxy-3-(2,4-dimethylphenyl)prop-1-yl)-bicyclo[3.2.0]hept-6-ylidene]-aminooxyacetic acid;

N-3-endo-hydroxy 2-exo-(3-hydroxy-4-phenylbut-1-yl)bicyclo[3.2.0]hept-6-ylidene]-aminooxyacetic acid;

N-3-endo-hydroxy-2-exo-(3-hydroxy-4-(4methoxyphenyl-but-1-yl)-bicyclo[3.2.0]hept-6-ylidene]aminooxyacetic acid;

N-3-endo-hydroxy-2-exo-(3-hydroxy-3-(3-trifluoromethylphenyl)prop-1-yl)-bicyclo[3.2.0]hept-6-ylidene]aminooxyacetic acid.

EXAMPLE 16

Alkynyl Aminooxyacetic Acid of Formula (2)

This example illustrates preparation of a compound of formula (2), namely N-[2-endo-hydroxy-3-exo(3αS-hydroxyoct-1-ynyl)bicyclo[3.2.0]hept-6-ylidene]aminooxyacetic acid.

In a manner analogous to that described in Example 13, but substituting octynyl bicycloheptanone (VII)(0.080 g) for ynone (VI) and using 0.033 g of NaOAc and 0.0525 g of carboxymethoxylamine hemihydrochloride, the crude oxyminoacetic acid is obtained. Purification by preparative layer chromatography furnishes the pure title compound as a glass exhibiting the anticipated spectral characteristics as well as a parent peak (C.I.M.S.) at m/e 324, $[\alpha]_D = -133°$ (methanol).

B. Similarly, by following the procedure of Example 13.A.1, but substituting for 2-endo-hydroxy-3-exo(3-hydroxy-oct-1-ynyl)bicyclo[3.2.0]heptan-6-one the corresponding alkynyl bicycloheptanone of Preparation 5.A.2.b, the following compounds are prepared, among others:

N-[2-endo-hydroxy-3-exo-(3-hydroxybut-1-ynyl)bicyclo[3.2.0]hept-6-ylidene]-aminooxyacetic acid;

N-[2-endo-hydroxy-3-exo-(3-hydroxypent-1-ynyl)bicyclo[3.2.0]hept-6-ylidene]-aminooxyacetic acid;

N-[2-endo-hydroxy-3-exo-(3-hydroxyhex-1-ynyl)bicyclo[3.2.0]hept-6-ylidene]-aminooxyacetic acid;

N-[2-endo-hydroxy-3-exo-(3-hydroxyhept-1-ynyl)bicyclo[-3.2.0]hept-6-ylidene]-aminooxyacetic acid;

N-[2-endo-hydroxy-3-exo-(3-hydroxynon-1-ynyl)bicyclo[3.2.0]hept-6-ylidene]-aminooxyacetic acid;

N-[2-endo-hydroxy-3-exo-(3-hydroxydec-1-ynyl)bicyclo[3.2.0]hept-6-ylidene]-aminooxyacetic acid, glass, C.I.M.S. exhibits a peak $MNH_4^+$ at m/e 369 and a peak $MH^+$ at m/e 352;

N-[2-endo-hydroxy-3-exo-(3-hydroxyundec-1-ynyl)-bicyclo[3.2.0]hept-6-ylidene]-aminooxyacetic acid;

N-[2-endo-hydroxy-3-exo-(3-hydroxydodec-1-ynyl)-bicyclo[3.2.0]hept-6-ylidene]-aminooxyacetic acid; C. In a similar manner by following the procedure of Example 13.A.1. but substituting 2-endo-hydroxy-3-exo(3-hydroxy-oct-1-ynyl)bicyclo[3.2.0]heptan-6-one by corresponding alkynyl bicycloheptanone isomer (B) chosen from those listed in the Preparation 5.A.3.b., the following representative compounds are prepared:

N-[2-endo-hydroxy-3-exo-(3-hydroxy-6-ethyloct-ynyl)-bicyclo[3.2.0]hept-6-ylidene]-aminooxyacetic acid;

N-[2-endo-hydroxy-3-exo-(3-hydroxy-3-cyclopentyl-prop-ynyl)-bicyclo[3.2.0]hept-6-ylidene]-aminooxyacetic acid, a glass whose C.I.M.S. contained an MH+ peak at m/e 322;

N-[2-endo-hydroxy-3-exo-(3-hydroxy-3-cyclohexyl-prop-1-ynyl)bicyclo[3.2.0]hept-6-ylidene]-aminooxyacetic acid, a glass whose C.I.M.S. contained an MH+ peak at m/e 336 and an MNH+ peak at m/e 353;

N-[2-endo-hydroxy-3-exo-(3-hydroxy-3-phenylprop-1-ynyl)bicyclo[3.2.0]hept-6-ylidene]-aminooxyacetic acid;

N-[2-endo-hydroxy-3-exo-(3-hydroxy-3-(4-chlorophenyl)prop-oct-1-ynyl)-bicyclo[3.2.0]hept-6-ylidene]aminooxyacetic acid;

N-[2-endo-hydroxy-3-exo-(3-hydroxy-3-(2,4-dimethylphenyl)prop-1-ynyl)-bicyclo[3.2.0]hept-6-ylidene]-aminooxyacetic acid;

N-[2-endo-hydroxy 3-exo-(3-hydroxy-4-phenylbut-1-ynyl)-bicyclo[3.2.0]hept-6-ylidene]-aminooxyacetic acid;

N-[2-endo-hydroxy-3-exo-(3-hydroxy-4-(4-methoxyphenylbut-1-ynyl)-bicyclo[3.2.0]hept-6-ylidene]-aminooxyacetic acid;

N-[2-endo-hydroxy-3-exo-(3-hydroxy-3-(3-trifluoromethylphenyl)prop-1-ynyl)-bicyclo[3.2.0]hept-6-ylidene]aminooxyacetic acid.

EXAMPLE 17

Alkenyl Aminooxyacetic Acid of Formula (2).

A. This example illustrates a method, according to the invention, of preparing the compound of the formula (2), N-[2-endo-hydroxy-3-exo-(3-hydroxy-oct-1-trans-enyl)bicyclo[3.2.0]hept-6-ylidene]aminooxyacetic acid. This compound is prepared by following the procedure of Example 13.A.1. but substituting 2-endo-hydroxy-3-exo-(3,αS-hydroxyoct-1-ynyl) bicyclo[3.2.0-]heptan-6-one (VIIIB) with 2-endo-hydroxy-3-exo-(3αS-hydroxy-oct-1-trans-enyl)bicyclo[3.2.0]heptan-6-one, according to the Preparation 5.B.1.b, a glass whose C.I.M.S. contained an MH+ peak at m/e 326.

B. Similarly, by following the procedure of Example 13.A.1, but substituting for 2-endo-hydroxy-3-exo(3-hydroxy-oct-1-ynyl)bicyclo[3.2.0]heptan-6-one the corresponding alkenyl bicycloheptanones isomer (B) according to Procedure 5.B.2.b, the following compounds are prepared:

N-[2-endo-hydroxy-3-exo-(3-hydroxybut-1-trans-enyl)-bicyclo[3.2.0]hept-6-ylidene]-aminooxyacetic acid;

N-[2-endo-hydroxy-3-exo-(3-hydroxypent-1-trans-enyl)bicyclo[3.2.0]hept-6-ylidene]-aminooxyacetic acid;

N-[2-endo-hydroxy-3-exo-(3-hydroxyhex-1-trans-enyl)-bicyclo[3.2.0]hept-6-ylidene]-aminooxyacetic acid;

N-[2-endo-hydroxy-3-exo-(3-hydroxyhept-1-trans-enyl)bicyclo[3.2.0]hept-6-ylidene]-aminooxyacetic acid;

N-[2-endo-hydroxy-3-exo-(3-hydroxynon-1-trans-enyl)-bicyclo[3.2.0]hept-6-ylidene]-aminooxyacetic acid;

N-[2-endo-hydroxy-3-exo-(3-hydroxydec-1-trans-enyl)-bicyclo[3.2.0]hept-6-ylidene]-aminooxyacetic acid;

N-[2-endo-hydroxy-3-exo-(3-hydroxyundec-1-trans-enyl)bicyclo-[3.2.0]hept-6-ylidene]-aminooxyacetic acid;

N-[2-endo-hydroxy-3-exo-(3-hydroxydodec-1-trans-enyl)bicyclo-[3.2.0]hept-6-ylidene]-aminooxyacetic acid;

C. In a similar manner by following the procedure of Example 13.A.1, but substituting for 2-endo-hydroxy-3-exo-(3-hydroxy-oct-1-ynyl)bicyclo[3.2.0]heptan-6-one the corresponding alkenyl bicycloheptanones chosen from those listed in the Preparation 5.B.3.b, the following representative compounds are prepared:

N-[2-endo-hydroxy-3-exo-(3-hydroxy-6-ethyloct-1-trans-enyl)bicyclo[3.2.0]hept-6-ylidene]-aminooxyacetic acid;

N-[2-endo-hydroxy-3-exo-(3-hydroxy-3-cyclopentyl-prop-1-trans-enyl)bicyclo[3.2.0]hept-6-ylidene]-aminooxyacetic acid, a glass whose C.I.M.S. contained an MH+ peak at m/e 324;

N-[2-endo-hydroxy-3-exo-(3-hydroxy-3-cyclohexyl-prop-1-trans-enyl)bicyclo[3.2.0]hept-6-ylidene]aminooxyacetic acid;

N-[2-endo-hydroxy-3-exo-(3-hydroxy-3-phenylprop-1-trans-enyl)bicyclo[3.2.0]hept-6-ylidene]-3-aminooxypropionic acid;

N-[2-endo-hydroxy-3-exo-(3-hydroxy-3-(4-chlorophenyl)prop-oct-1-trans-enyl)-bicyclo[3.2.0]hept-6-ylidene]aminooxyacetic acid;

N-[2-endo-hydroxy-3-exo-(3-hydroxy-3-(2,4-dimethylaminooxyacetic acid;

N-[2-endo-hydroxy 3-exo-(3-hydroxy-4-phenylbut-1-trans-enyl)-bicyclo[3.2.0]hept-6-ylidene]-amino- oxyacetic acid;

N-[2-endo-hydroxy-3-exo-(3-hydroxy-4-(4-methoxyphenylbut-1-trans-enyl)-bicyclo[3.2.0]hept-6-ylidene]aminooxyacetic acid;

N-[2-endo-hydroxy-3-exo-(3-hydroxy-3-(3-trifluoromethylphenyl)prop-1-trans-enyl)-bicyclo[3.2.0]hept-6-ylidene]-aminooxyacetic acid.

EXAMPLE 18

Alkyl Aminooxyacetic Acid of Formula (2).

A. This example illustrates a method, according to the invention, of preparing the compound of the formula (2), N-[2-endo-hydroxy-3-exo-(3-hydroxy-oct-1-yl)557bicyclo[ 3.2.0)hept-6-ylidene]-aminooxyacetic acid.

This compound is prepared by following the procedure of Example 13.A.1, but substituting 2-endo-hydroxy-3-exo(3-hydroxy-oct-1-ynyl)bicyclo[3.2.0-]heptan-6-one (VIIIB) with 2-endo-hydroxy-3-exo-(3-hydroxy-oct-1-yl)bicyclo[3.2.0]heptan-6-one according to Procedure 5.C.1.b, a glass whose C.I.M.S. contained an MH+ peak at m/e 328.

B. Similarly, by following the procedure of Example 13.A.1, but substituting for 2-endo-hydroxy-3-exo(3-hydroxy-oct-1-ynyl)bicyclo[3.2.0]heptan-6-one the corresponding alkyl bicycloheptanones chosen from those listed in Preparation 5.C.2.b, the following compounds are prepared:

N-[2-endo-hydroxy-3-exo-(3-hydroxybut-1-yl)bicyclo[3.2.0]hept-6-ylidene]-aminooxyacetic acid;

N-[2-endo-hydroxy-3-exo-(3-hydroxypent-1-yl)bicyclo[3.2.0]hept-6-ylidene]-aminooxyacetic acid;

N-[2-endo-hydroxy-3-exo-(3-hydroxyhex-1-yl)bicyclo[3.2.0]hept-6-ylidene]-aminooxyacetic acid;

N-[2-endo-hydroxy-3-exo-(3-hydroxyhept-1-yl)bicyclo[3.2.0]hept-6-ylidene]-aminooxyacetic acid;

N-[2-endo-hydroxy-3-exo-(3-hydroxynon-1-yl)bicyclo[3.2.0]hept-6-ylidene]-aminooxyacetic acid;

N-[2-endo-hydroxy-3-exo-(3-hydroxydec-1-yl)bicyclo[3.2.0]hept-6-ylidene]-aminooxyacetic acid, a glass whose C.I.M.S. contained an MH+ peak at m/e 356 and an MNH+ peak at m/e 373;

N-[2-endo-hydroxy-3-exo-(3-hydroxyundec-1-yl)bicyclo[3.2.0]hept-6-ylidene]-aminooxyacetic acid;

N-[2-endo-hydroxy-3-exo-(3-hydroxydodec-1-yl)bicyclo[3.2.0]hept-6-ylidene]-aminooxyacetic acid;

C. In a similar manner by following the procedure of Example 13.A.1, but substituting for 2-endo-hydroxy-3-exo-(3-hydroxy-oct-1-yl)bicyclo[3.2.0]heptan-6-one the corresponding alkyl bicycloheptanone listed in the Preparation 5.C.3.b, the following representative compounds are prepared:

N-[2-endo-hydroxy-3-exo-(3-hydroxy-6-ethyloct-1-yl)bicyclo[3.2.0]hept-6-ylidene]-aminooxyacetic acid;

N-[2-endo-hydroxy-3-exo-(3-hydroxy-3-cyclopentyl-prop-1-yl)bicyclo[3.2.0]hept-6-ylidene]-aminooxyacetic acid, a glass whose C.I.M.S. contained an MH+ peak at m/e 326;

N-[2-endo-hydroxy-3-exo-(3-hydroxy-3-cyclohexyl-prop-1-yl)bicyclo[3.2.0]hept-6-ylidene]-aminooxyacetic acid, a glass whose C.I.M.S. contained an MH+ peak at m/e 340 and an MNH+peak at m/e 357;

N-[2-endo-hydroxy-3-exo-(3-hydroxy-3-phenylprop-1-yl)bicyclo[3.2.0]hept-6-ylidene]-aminooxyacetic acid;

N-[2-endo-nydroxy-3-exo-(3-hydroxy-3-(4-chlorophenyl) prop-oct-1-yl)-bicyclo[3.2.0]hept-6-ylidene]aminooxyacetic acid;

N-[2-endo-hydroxy-3-exo-(3-hydroxy-3-(2,4-dimethyl phenyl)prop-1-yl)-bicyclo[3.2.0]hept-6-ylidene]-aminooxyacetic acid;

N-[2-endo-hydroxy 3-exo-(3-hydroxy-4-phenylbut-1-yl)-bicyclo[3.2.0]hept-6-ylidene]-aminooxyacetic acid;

N-[2-endo-hydroxy-3-exo-(3-hydroxy-3-(3-trifluoromethylphenyl)prop-1-yl)-bicyclo[3.2.0]hept-6-ylidene]aminooxyacetic acid;

N-[2-endo-hydroxy-3-exo-(3-hydroxy-4-(4-methoxyphenylbut-1-yl)-bicyclo[3.2.0]hept-6-ylidene]-aminooxyacetic acid.

EXAMPLE 19

Alkynyl, Alkenyl, or Alkyl Aminooxyvaleric Acid of Formula (1) or (2)

This example illustrates methods according to the invention, of preparing 5-aminooxyvaleric acid derivatives of alkynyl, alkyl and alkenyl bicycloheptanone isomers (A) and (B). These compounds are prepared following the procedures of Examples 1–3 (A-C) and 7–9 (A-C) and substituting 3-aminooxypropionic acid by 5-aminooxyvaleric acid from Preparation 7.

EXAMPLE 20

Preparation of Salt Derivatives from Acids

This example illustrates methods for preparing the pharmaceutically acceptable salts of the invention. The sodium salt derivative of the compound of formula (1) prepared in Example 1, for example, N-[3-endo-hydroxy-2-exo-(3-hydroxy-oct-1-ynyl)bicyclo[3.2.0-]hept-6-ylidene]-3-aminooxypropionic acid, is prepared by treating a methanolic solution of said acid with one molar equivalent of 1N aqueous sodium hydroxide solution at an ambient temperature. Evaporation of the solvents under reduced pressure furnishes a solid residue of the desired sodium salt.

The sodium salt derivatives of the other compounds prepared in Examples 1–18 are prepared similarly using the same procedure.

EXAMPLE 21

Preparation of Acid Derivatives from Salts

This example illustrates methods for preparing acid derivatives from salt derivatives of the compounds prepared in Examples 1–18.

The sodium salt of N-[2-endo-hydroxy-3-exo-(3-hydroxy-oct-1-yl)-bicyclo[3.2.0)hept-6-ylidene]-3-aminooxypropionic acid was dissolved in water or water soluble solvent (as defined above) and acidified with diluted HCl (1N) at 0° to 25° C. to pH 4. The organic material was extracted with suitable solvents, e.g., ethyl acetate, ether, methylene chloride. The organic solution was washed with water, brine dried over magnesium sulfate and evaporated to give N-[2-endo-hydroxy-3-exo-(3-hydroxy-oct-1-yl)-bicyclo[3.2.0)hept-6-ylidene]-3-aminooxypropionic acid.

Similarly, other salts of aminooxyacids of Examples 1–18 are converted to their corresponding free acids.

EXAMPLE 22

Preparation of Carboxylic Esters from Acids of Formula (2)

A. Methyl ester of N-[2-endo-hydroxy-3-exo-(3-hydroxyoct-1-ynyl)-bicyclo[3.2.0]hept-6-ylidene]-aminooxyacetic acid.

A solution of N-[2-endo-hydroxy-3-exo-(3-hydroxyoct-1-ynyl)-bicyclo[3.2.0]hept-6-ylidene]-aminooxyacetic acid prepared according to Example 16 (0.100 g) in 5 ml of ether is treated with an ethereal solution containing a molar excess of diazomethane. The yellow mixture is held at room temperature for 2 hours, then acetic acid is added dropwise until the remaining color is discharged. Solvent is removed by evaporation under reduced pressure, and the virtually pure residue so obtained is given a final purification by preparative layer chromatography to furnish the title compound.

B. In similar fashion but substituting higher diazoalkanes for the diazomethane employed in the preceeding example, the corresponding higher alkyl esters of the starting acid are prepared. The requisite diazoalkanes are known. They may be prepared, by conventional methods, e.g. as described in *Org. Reactions*, 8, 389–94, (1954).

Furthermore, by employing the procedure and diazoalkane reagents of this Example but substituting the other acid products of formula (2) prepared according to Examples 7–12 and 16–18 for the aminooxyacetic acid starting material utilized above, the corresponding alkyl esters of each oximinoalkanoic acid product of formula (2) are prepared.

EXAMPLE 23

Preparation of Carboxylic Esters Corresponding to the Novel Carboxylic Acid Products of this Invention of Formula (1)

By reacting the carboxylic acid products of formula (1), obtained following the procedure of Example 1-6 and 13-15 with diazoalkanes according to the method described in the preceeding Example, the alkyl esters corresponding to the formula (1) acid starting materials are prepared.

EXAMPLE 24

Preparation of Carboxylic Esters from Acids of Formula (1) or (2) by Reaction of Their Carboxylate Salts with Alkyl Halides Ethyl N-[2-endo-hydroxy-3-exo-(3-hydroxyoct-1-ynyl)-bicyclo[3.2.0]hept-6-ylidene]-3-aminooxypropionate.

The toxicity and explosion hazard engendered by the diazoalkanes makes them undesirable reagents for large scale esterifications. This Example describes an alternative mild esterification procedure (*Bull. Chem. Soc. Japan,* 51, 2401 (1978)) more suitable for manufacturing purposes. To a solution of N-[2-endo-hydroxy-3-exo-(3-hydroxyoct-1-ynyl)bicyclo-[3.2.0]hept-6-ylidene]-aminooxyacetic acid (0.200 g) in benzene (30 ml) are added 4 equiv. of 1,8-diazabicyclo[5.4.0]undec-7-ene (DBU), followed by dropwise addition to the stirred DBU-carboxylate complex, of ethyl iodide (1.5 equiv.). After stirring an additional 2 hours at room temperature the reaction mixture is evaporated to $\frac{1}{3}$ volume under reduced pressure. The concentrate is washed with 3 portions of dilute ice-cold aqueous HCl, twice with saturated brine, dried over $Na_2SO_4$, and evaporated to give a virtually pure residue of the desired ethyl ester. By following the above procedure but substituting other alkyl bromides or alkyl iodides for the ethyl iodide used therein, the corresponding alkyl esters derived from the acid starting material of formula (2) are prepared. When the esterifications proceed too slowly at ambient temperature (particularly when alkyl bromides are employed as alkylating agents) it is advantageous to conduct the esterification reaction at the boiling point of the reaction system (80° C.).

In similar fashion, by subjecting the acid products (formulas (1) and (2), respectively,) of our invention prepared as described in Examples 1-18 to the esterification procedure of the present Example employing the appropriate alkyl halide as an alkylating reagent, the corresponding esters derived from the free carboxylic acid products of formulas (1) and (2) are prepared.

EXAMPLE 25

Preparation of Free Carboxylic Acid Products, Structures (I) and (II), by Saponification of the Corresponding Esters This Example describes preparation of the carboxylic acids of our invention formula (1) or (2) by saponification of their corresponding alkyl esters. Saponification may be carried out employing a wide variety of organic and/or inorganic bases under conventional and well-known reaction conditions. The following procedure is given for illustrative purposes only and is not intended to be limiting in any sense.

A solution of the methyl ester (0.05 g) of a N-[3-endo-hydroxy-2-exo-(3-hydroxybut-1-yl)-bicyclo[3.2.0]-hept-6-ylidene]-3-aminooxypropionic acid prepared according to procedure of Example 22 or 24 in 3 ml of methanol is purged with argon and stirred under an argon atmosphere while 0.5 ml of in aqueous NaOH is added. Stirring is continued for 4 hours at ambient temperature, followed by evaporation of most of the solvent under reduced pressure. The concentrate is diluted with 10 ml of $H_2O$ and, after adjusting the pH to between 5.5 and 6.5, extracted with 3 portions of methylene chloride. The combined extracts are washed with saturated brine, dried over sodium sulfate, and evaporated under reduced pressure to afford the free carboxylic acid of structure corresponding to the carboxylate residue in the ester being hydrolyzed. Similarly, the other esters prepared from the novel oximino acids of our invention according to Examples 22-24 are saponified to furnish the corresponding free acids of formulas (1) and (2).

EXAMPLE 26

Preparation of Esters from Esters

This example illustrates methods for preparation of other esters from ester compounds prepared in Examples 1-18.

A small piece of sodium was added to a selected alcohol. After all the solid was digested, an alkoxide solution resulted. Methyl ester of N-[3-endo-hydroxy-2-exo-(3-hydroxybut-1-yl)-bicyclo[3.2.0]-hept-6-ylidene]-3-aminooxypropionic acid was dissolved in the ethyl alcohol and to this solution was added a drop of the alkoxide solution. After the reaction was complete (as determined by TLC), the solution was neutralized and evaporated to dryness. The residue was partitioned between ethyl acetate and water. The organic layer was washed with water, brine, and dried over magnesium sulfate. The solvent was removed under vacuum and the residue was an ethyl ester of the N-[3-endo-hydroxy-2-exo-(3-hydroxybut-1-yl)-bicyclo[3.2.0]-hept-6-ylidene]-3-aminooxypropionic acid.

EXAMPLE 27

In Vitro Human Platelet Aggregation Inhibition

Biological activity of the claimed compounds is tested by in vitro human platelet aggregation assay. This assay determines the effectiveness of the compounds in inhibiting the platelet aggregation The assay employs modified turbidimetric methods of Born (*J. Physiol.,* 67P (1962) and Evans et al, *J. Exp. Med.,* 128, 877P (1968), and it is based on the physiological response of the blood platelets to a certain stimuli. In normal circulating blood, platelets are carried along separately from each other and they do not adhere to undamaged endothelium. In response to any direct damage to the vascular wall, however, the blood platelets will start to aggregate. Thus, whenever there occurs an injury causing bleeding, rupture, cut or another type of damage to vascular wall, the collagen fibers in the wall become exposed and platelets immediately start to adhere to them and begin to form a platelet thrombi. Immediately thereafter, the platelets start to secrete large quantities of adenosine diphosphate (ADP) which, in turn activates the other platelets that adhere to the original platelets and eventually form the plug which closes the rupture of the vascular wall. In medical parlance the first process is called collagen-induced primary platelet aggregation, the second process is called ADP-mediated secondary platelet aggregation. This situation can be artificially simulated by natural platelet aggregation inducers such as collagen, ADP, or arachidonic acid to the human platelet-rich plasma.

Preparation of Human Platelets-Rich Plasma

The blood samples used for the assay are collected into sodium citrate anticoagulant of a final concentration of 0.38%. The platelet-rich plasma is collected after centrifugation at 200 rpm at room temperature. To determine whether the platelet-rich plasma needs dilution to obtain optimal optical density, citrated plasma containing $10^{-8}$–$10^{-9}$ platelets per milliliter is pipetted into a Spinco transparent plastic centrifuge tube. The tube is inserted into a Unicam SP 400 absorptiometer and the light at the wave-length of 600 m$\mu$ is passed through the tube. The dark current is set at infinity and the optical density of distilled water at zero. The plasma is stirred by a magnetic stirrer. If necessary, platelet-rich plasma is diluted with 0.154M sodium chloride to obtain appropriate optical density Platelet Aggregation Procedure Platelet-rich plasma of appropriate optical density is mixed with appropriate concentration of tested compounds to make up 1 ml of mixture of platelet-rich plasma and tested compound. The concentration of each tested compound varied from $1.0 \times 10^{-5}$ moles to $1.0 \times 10^{-9}$ moles. Each concentration is tested individually by number of repetitions varying from 1 to 6. Each sample mixture consisting of platelet-rich plasma and tested compound is incubated for about 3 to 5 minutes under constant stirring at 500 rpm at 30° C. Thereafter, a predetermined optimal concentration of platelet aggregation inducer is added to each sample mixture. Inducers which are used for testing may be chosen from:

1. Collagen Suspension Inducer

Collagen suspension is prepared by dissolving 2 g of commercial collagen (Sigma Chemical Company) in 100 ml of modified Tyrode's solution at 0° C. and homogenized in the Waring blender for a total of 5 minutes To remove coarse particle matter the mixture is centrifuged at 810 rpm for 10 minutes. The supernatant suspension is then diluted with modified Tyrode's solution to a concentration which produce maximum aggregation of the platelets being tested, but which, on further dilution, cause less than maximum aggregation.

2. Adenosine Diphosphate Inducer

Adenosine Diphosphate (ADP) is purchased from Sigma Chemical Company. ADP inducer solution of final concentration of 5 $\mu$mol is prepared by dissolving 214 mg of ADP in 1 ml of tris buffer (0.01M at pH 9 at 22° C.). Optimal amount of ADP inducer was found to be 5 $\mu$mol.

3. Arachidonic Acid Inducer

Arachidonic acid (Nu Chek Prep Co.) inducer solution is prepared by dissolving 150–300 $\mu$g of arachidonic acid in 1 ml of a mixture of 10% of ethanol and 90% of 65.6 mmol of sodium carbonate buffer to achieve concentration 0.5 to 1 mmol.

A tube with the mixture of platelet-rich plasma, tested compound and ADP inducer (5 $\mu$mol/10 $\mu$l) is inserted into the absorptiometer and optical density changes are recorded on chart. Aggregation of the platelets is determined from maximal optical density change. Maximal optical density of a mixture of platelet-rich plasma with inducer, but without the tested compounds, is taken as 100% of platelet aggregation. The maximal optical density of the sample mixture of platelet-rich plasma, ADP inducer and appropriate amount of tested compound is compared to the maximal optical density of the sample without tested compound and inhibitory effectiveness of tested compounds is calculated. For each sample the percentage of the platelet aggregation is calculated and if more than one measurement with the same concentration of the tested compounds are done, the final value is expressed as an average of all measurements with ±S.E. The inhibitory concentration is the effective concentration of tested compound which is able to prevent 50% of the platelet aggregation, where, without the tested compound, the platelet aggregation would have been 100%. PGE$_1$ has an IC$_{50}$ of $2$–$8 \times 10^{-8}$M.

The compounds of this invention were tested by this procedure and were found to be active inhibitors of platelet aggregation. (see Table I)

TABLE I

| Compound | ADP Inducer IC$_{50}$ (M) |
|---|---|
| 1. N—[2-endo-hydroxy-3-exo-(3$\alpha$S—hydroxyoct-1-ynyl)bicyclo-[3.2.0]hept-6-ylidene]aminooxyacetic acid | $1.86 \times 10^{-8}$ |
| 2. N—[2-endo-hydroxy-3-exo-(3$\alpha$S—hydroxyoct-1-trans-enyl)-bicyclo[3.2.0]hept-6-ylidene]-aminooxyacetic acid | $8.9 \times 10^{-8}$ |
| 3. N—[2-endo-hydroxy-3-exo-(3$\alpha\beta$S—hydroxyoct-1-yl)-bicyclo[3.2.0]hept-6-ylidene]-aminooxyacetic acid | $1.4 \times 10^{-6}$ |
| 4. N—[2-endo-hydroxy-3-exo-(3-hydroxy-3-cyclopentylprop-1-ynyl)bicyclo[3.2.0]hept-6-ylidene]aminooxyacetic acid | $1.25 \times 10^{-8}$ |
| 5. N—[2-endo-hydroxy-3-exo-3$\alpha$-hydroxy-3-cyclopentyl-prop-1-trans-enyl)bicyclo[3.2.0]-hept-6-ylidene]aminooxyacetic acid | $1.12 \times 10^{-8}$ |
| 6. N—[2-endo-hydroxy-3-exo-(3-hydroxy-3-cyclopentyl-prop-1-yl)bicyclo[3.2.0]-hept-6-ylidene]aminooxyacetic acid | $1.0 \times 10^{-6}$ |
| 7. N—[2-endo-hydroxy-3-exo-(3-hydroxy-3-cyclohexyl-prop-1-ynyl)bicyclo[3.2.0]-hept-6-ylidene]aminooxyacetic acid | $2.4 \times 10^{-8}$ |
| 8. N—[2-endo-hydroxy-3-exo-(3-hydroxy-3-cyclohexyl-prop-1-yl)bicyclo[3.2.0]-hept-6-ylidene]aminooxyacetic acid | $8.8 \times 10^{-8}$ |
| 9. N—[2-endo-hydroxy-3-exo-(3-hydroxydec-1-ynyl)bicyclo-[3.2.0]hept-6-ylidene]-aminooxyacetic acid | $3.2 \times 10^{-8}$ |
| 10. N—[2-endo-hydroxy-3-exo-(3-hydroxydec-1-yl)bicyclo-[3.2.0]hept-6-ylidene]-aminooxyacetic acid | $2.35 \times 10^{-70}$ |
| 11. N—[2-endo-hydroxy-3-exo-(3$\alpha\beta$S—hydroxyoct-1-ynyl)-bicyclo[3.2.0]hept-6-ylidene]-aminooxyacetic acid | $7.0 \times 10^{-8}$ |
| 12. N—[2-endo-hydroxy-3-exo-(3$\alpha$S—hydroxyoct-1-ynyl)-bicyclo[3.2.0]hept-6-ylidene]-3-aminooxypropionic acid | $3.1 \times 10^{-8}$ |
| 13. N—[2-endo-hydroxy-3-exo-(3$\alpha$S—hydroxyoct-1-trans-enyl)-bicyclo[3.2.0]hept-6-ylidene]- | $6.9 \times 10^{-9}$ |

TABLE I-continued

| | Compound | ADP Inducer IC$_{50}$ (M) |
|---|---|---|
| | 3-aminooxypropionic acid | |
| 14. | N—[2-endo-hydroxy-3-exo-(3αβS—hydroxyoct-1-yl)-bicyclo[3.2.0]hept-6-ylidene]-3-aminooxypropionic acid | $2.2 \times 10^{-6}$ |
| 15. | N—[2-endo-hydroxy-3-exo-(3-hydroxy-3-cyclopentylprop-1-ynyl)bicyclo[3.2.0]hept-6-ylidene]-3-aminooxypropionic acid | $3.1 \times 10^{-8}$ |
| 16. | N—[2-endo-hydroxy-3-exo-(3α-hydroxy-3-cyclopentylprop-1-trans-enyl)bicyclo[3.2.0]hept-6-ylidene]-3-aminooxypropionic acid | $1.05 \times 10^{-8}$ |
| 17. | N—[2-endo-hydroxy-3-exo-(3-hydroxy-3-cyclopentylprop-1-yl)bicyclo[3.2.0]hept-6-ylidene]-3-aminooxypropionic acid | $1.02 \times 10^{-6}$ |
| 18. | N—[2-endo-hydroxy-3-exo-(3-hydroxy-3-cyclohexylprop-1-ynyl)bicyclo[3.2.0]hept-6-ylidene]-3-aminooxypropionic acid | $8.4 \times 10^{-9}$ |
| 19. | N—[2-endo-hydroxy-3-exo-(3α-hydroxy-3-cyclohexylprop-1-trans-enyl)bicyclo[3.2.0]hept-6-ylidene]-3-aminooxypropionic acid | $8.1 \times 10^{-8}$ |
| 20. | N—[2-endo-hydroxy-3-exo-(3-hydroxy-3-cyclohexylprop-1-yl)bicyclo[3.2.0]hept-6-ylidene]-3-aminooxypropionic acid | $2.35 \times 10^{-6}$ |
| 21. | N—[2-endo-hydroxy-3-exo-(3-hydroxydec-1-ynyl)bicyclo[3.2.0]hept-6-ylidene]-3-aminooxypropionic acid | $1.17 \times 10^{-7}$ |
| 22. | N—[2-endo-hydroxy-3-exo-(3-hydroxydec-1-yl)bicyclo[3.2.0]hept-6-ylidene]-3-aminooxypropionic acid | $1.3 \times 10^{-6}$ |
| 23 | N—[2-endo-hydroxy-3-exo-(3-hydroxyoct-1-ynyl)bicyclo[3.2.0]hept-6-ylidene]-3-aminooxypropionic acid | $1.75 \times 10^{-7}$ |
| 24. | N—[2-endo-hydroxy-3-exo-(3αβS—hydroxyoct-1-ynyl)bicyclo[3.2.0]hept-6-ylidene]-3-aminooxypropionic acid | $4.3 \times 10^{-8}$ |
| 25. | N—[2-endo-hydroxy-3-exo-(3αβS—hydroxyoct-1-ynyl)bicyclo[3.2.0]hept-6-ylidene]-4-aminooxybutyric acid | $4.2 \times 10^{-7}$ |
| 26. | N—[3-endo-hydroxy-2-exo-(3αβS—hydroxyoct-1-ynyl)bicyclo[3.2.0]hept-6-ylidene]-3-aminooxypropionic acid | $2.1 \times 10^{-5}$ |
| 27. | N—[3-endo-hydroxy-2-exo-(3αβS—hydroxyoct-1-ynyl)bicyclo[3.2.0]hept-6-ylidene]-4-aminooxybutyric acid | $1.1 \times 10^{-6}$ |

EXAMPLE 27

Acute Toxicity of N-[2-endo-hydroxy-3-exo-(3-hydroxyoct-1-ynyl)bicyclo[3.2.0]hept-6-ylidene]-3-aminopropionic acid

Materials and Methods

Male Sim: (SW)$_f$BR mice weighing approximately 25 g were randomly assigned to treatment groups of 6 animals, caged together, and were given food and water ad libitum.

The test material was prepared as an aqueous solution or suspension in CMC vehicle (sodium carboxymethyl cellulose, 0.5 g; sodium chloride, 0.9 g; benzyl alcohol, 0.9 ml; Tween 80, 0.4 ml; and water to 100 ml). The test material and the control vehicle were administered once by the indicated route at a dose level of 10 ml per kg body weight.

Following administration of the test material on day 1, animals were observed daily and any deaths were recorded.

| | | RESULTS | | | |
|---|---|---|---|---|---|
| Test Material | Dose mg/kg | Route of Administration | No. of Mice | No. of Deaths | Days Observed |
| Vehicle Control | — | Intraperitoneal | 6 | 0 | 14 |
| Test Material | 120 | Intraperitoneal | 6 | 0 | 14 |

Based on the results shown in the above Table, N-[2-endo-hydroxy-3-exo-(3-hydroxyoct-1-ynyl)bicyclo-[3.2.0]hept-6-ylidene]-3-aminopropionic acid, when administered intraperitoneally to mice in a single dose, has an LD$_{50}$ of greater than 120 mg/kg. The other compounds of this invention exhibit similar toxicity.

What is claimed is:

1. A compound or its optical isomers chosen from those represented by the formulas

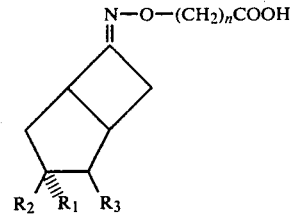

(1)

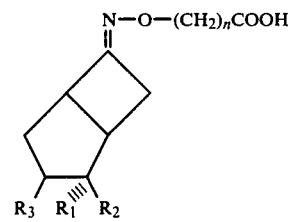

(2)

and the pharmaceutically acceptable non-toxic salts and esters thereof, wherein:

n is an integer from one to four;

R$_1$ is hydroxy;

R$_2$ is hydrogen; or

R$_1$ and R$_2$ together are an oxo group; and

R$_3$ is —A—CHOH—R$_4$ wherein

A is —CH$_2$—CH$_2$—; trans—CH=CH—; or —C≡C—; and

R$_4$ is linear or branched alkyl of one to twelve carbons, preferably 1–10 carbons, most preferably 3–8 carbons, cycloalkyl of three to eight carbons; phenyl optionally substituted with one or two identical substituents selected from the group consisting of lower alkyl, lower alkoxy, hydroxy, trifluoromethyl and halo; or phenyl-loweralkyl optionally substituted with one or two identical substituents selected from the group consisting of lower alkyl, lower alkoxy, hydroxy, trifluoromethyl, and halo.

2. The compound of claim 1 and the pharmaceutically acceptable non-toxic salts and esters thereof, wherein the compound is represented by formula (1).

3. The compound of claim 2 and the pharmaceutically acceptable non-toxic salts and esters thereof, wherein n is 1, 2 or 3.

4. The compound of claim 3 and the pharmaceutically acceptable, non-toxic salts and esters thereof, wherein n is 1.

5. The compound of claim 4 and the pharmaceutically acceptable non-toxic salts and esters thereof, wherein A is C≡C.

6. The compound of claim 5 wherein R$_1$ is OH; R$_2$ is H; and R$_4$ is 5 carbon linear alkyl, namely N-[3-endo-hydroxy-2-exo-(3-hydroxy-oct-1-ynyl)bicyclo[3.2.0]hept-6-ylidene]aminooxyacetic acid and the pharmaceutically acceptable non-toxic salts and esters thereof.

7. The compound of claim 3 and the pharmaceutically acceptable non-toxic salts and esters thereof, wherein n is 2.

8. The compound of claim 7 and the pharmaceutically acceptable non-toxic salts and esters thereof, wherein A is C≡C.

9. The compound of claim 8 wherein R$_1$ is OH; R$_2$ is H; and R$_4$ is 5 carbon linear alkyl, namely N-[3-endo-hydroxy-2-exo-(3-hydroxy-oct-1-ynyl)bicyclo[3.2.0]hept-6-ylidene]-3-aminooxypropionic acid and the pharmaceutically acceptable non-toxic salts and esters thereof.

10. The compound of claim 3 and the pharmaceutically acceptable non-toxic salts and esters thereof, wherein n is 3.

11. The compound of claim 10 and the pharmaceutically acceptable non-toxic salts and esters thereof, wherein A is C≡C.

12. The compound of claim 11 wherein R$_1$ is OH; R$_2$ is H; and R$_4$ is 5 carbon linear alkyl, namely, N-[3-endo-hydroxy-2-exo-(3-hydroxy-oct-1-ynyl)bicyclo[3.2.0]hept-6-ylidene]-4-aminooxybutyric acid and the pharmaceutically acceptable non-toxic salts and esters thereof.

13. The compound or its optical isomers of claim 1 and the pharmaceutically acceptable non-toxic salts and esters thereof, wherein the compound is represented by formula (2).

14. The compound or its optical isomers of claim 13 and the pharmaceutically acceptable non-toxic salts and esters thereof, wherein n is 1, 2 or 3.

15. The compound or its optical isomers of claim 14 and the pharmaceutically acceptable non-toxic salts and esters thereof, wherein n is 1.

16. The compound or its optical isomers of claim 15 and the pharmaceutically acceptable non-toxic salts and esters thereof, wherein A is C≡C.

17. The compound or its optical isomers of claim 16 wherein R$_1$ is OH; R$_2$ is H; and R$_4$ is 5 carbon linear alkyl, namely N-[2-endo-hydroxy-3-exo-(3-hydroxyoct-1-ynyl)bicyclo-[3.2.0]hept-6-ylidene]aminooxyacetic acid; N-[2-endo-hydroxy-3-exo-(3α$\beta$S-hydroxyoct-1-ynyl)bicyclo[3.2.0]hept-6-ylidene]aminooxyacetic acid; N-[2-endo-hydroxy-3-exo-(3αS-hydroxyoct-1-ynyl)-bicyclo[3.2.0]hept-6-ylidene]aminooxyacetic acid and the pharmaceutically acceptable non-toxic salts and esters thereof.

18. The compound of claim 16 wherein R$_1$ is OH; R$_2$ is H; and R$_4$ is a 7 carbon linear alkyl, namely N-[2-endo-hydroxy-3-exo-(3-hydroxydec-1-ynyl)bicyclo[3.2.0]hept-6-ylidene]aminooxyacetic acid or its optical isomers and the pharmaceutically acceptable non-toxic salts and esters thereof.

19. The compound of claim 16 wherein R$_1$ is OH; R$_2$ is H; and R$_4$ is a 5 carbon cyclic alkyl, namely N-[2-endo-hydroxy-3-exo-(3-hydroxy-3-cyclopentylprop-1-ynyl)bicyclo[3.2.0]hept-6-ylidene]aminooxyacetic acid or its optical isomers and the pharmaceutically acceptable non-toxic salts and esters thereof.

20. The compound of claim 16 wherein R$_1$ is OH; R$_2$ is H; and R$_4$ is a 6 carbon cyclic alkyl, namely N-[2-endo-hydroxy-3-exo-(3-hydroxy-3-cyclohexylprop-1-ynyl)bicyclo[3.2.0]hept-6-ylidene]aminooxyacetic acid or its optical isomers and the pharmaceutically acceptable non-toxic salts and esters thereof.

21. The compound or its optical isomers of claim 14 and the pharmaceutically acceptable non-toxic salts and esters thereof, wherein n is 2.

22. The compound or its optical isomers of claim 21 and the pharmaceutically acceptable non-toxic salts and esters thereof, wherein A is C≡C.

23. The compound or its optical isomers of claim 22 wherein R$_1$ is OH; R$_2$ is H; and R$_4$ is 5 carbon linear alkyl, namely, N-[2-endo-hydroxy-3-exo(3-hydroxy-oct-1-ynyl)bicyclo[3.2.0]hept-6-ylidene]-3-aminooxypropionic acid; N-[2-endo-hydroxy-3-exo-(3α$\beta$S-hydroxyoct-1-ynyl)bicyclo[3.2.0]hept-6-ylidene]-3-aminooxypropionic acid; N-[2-endo-hydroxy-3-exo-(3αS-hydroxyoct-1-ynyl)bicyclo[3.2.0]hept-6-ylidene]-3-aminooxypropionic acid and the pharmaceutically acceptable non-toxic salts and esters thereof 24. The compound of claim 22 wherein R$_1$ is OH; R$_2$ is H; and R$_4$ is a 7 carbon linear alkyl, namely N-[2-endo-hydroxy-3-exo-(3-hydroxydec-1-ynyl)bicyclo[3.2.0]hept-6-ylidene]-3-aminooxypropionic acid or its optical isomers and the pharmaceutically acceptable non-toxic salts and esters thereof.

25. The compound of claim 22 wherein R$_1$ is OH; R$_2$ is H; and R$_4$ is a 5 carbon cyclic alkyl, namely N-[2-endo-hydroxy-3-exo-(3-hydroxy-3-cyclopentylprop-1-ynyl)bicyclo[3.2.0]hept-6-ylidene]-3-aminooxypropionic acid or its optical isomers and the pharmaceutically acceptable non-toxic salts and esters thereof.

26. The compound of claim 22 wherein R$_1$ is OH; R$_2$ is H; and R$_4$ is a 6 carbon cyclic alkyl, namely N-[2-endo-hydroxy-3-exo-(3-hydroxy-3-cyclohexylprop-1-ynyl)bicyclo[3.2.0]hept-6-ylidene]-3-aminooxypropionic acid or its optical isomers and the pharmaceutically acceptable non-toxic salts and esters thereof.

27. The compound or its optical isomers of claim 14 and the pharmaceutically acceptable non-toxic salts and esters thereof, wherein n is 3.

28. The compound or its optical isomers of claim 27 and the pharmaceutically acceptable non-toxic salts and esters thereof, wherein A is C≡C.

29. The compound of claim 28 wherein $R_1$ is OH; $R_2$ is H; and $R_4$ is 5 carbon linear alkyl, namely, N-[2-endo-hydroxy-3-exo-(3-hydroxy-oct-1-ynyl)bicyclo[3.2.0]hept-6-ylidene]-4-aminooxybutyric acid or its optical isomers and the pharmaceutically acceptable non-toxic salts and esters thereof.

30. The compound or its optical isomers of claim 15 and the pharmaceutically acceptable non-toxic salts and esters thereof, wherein A is trans —CH=CH—.

31. The compound or its optical isomers of claim 30 wherein $R_1$ is OH; $R_2$ is H; and $R_4$ is a 5 carbon linear alkyl, namely N-[2-endo-hydroxy-3-exo-(3-hydroxyoct-1-trans-enyl)bicyclo[3.2.0]hept-6-ylidene]aminooxyacetic acid; N-[2-endo-hydroxy-3-exo-(3αS-hydroxyoct-1-trans-enyl)bicyclo[3.2.0]hept-6-ylidene]aminooxyacetic acid and the pharmaceutically acceptable non-toxic salts and esters thereof.

32. The compound or its optical isomers of claim 30 wherein $R_1$ is OH; $R_2$ is H; and $R_4$ is a 5 carbon cyclic alkyl, namely N-[2-endo-hydroxy-3-exo-(3-hydroxy-3-cyclopentylprop-1-trans-enyl)bicyclo[3.2.0]hept-6-ylidene]aminooxyacetic acid; N-[2-endo-hydroxy-3-exo-(3α-hydroxy-3-cyclopentylprop-1-trans-enyl)bicyclo[3.2.0]hept-6-ylidene]aminooxyacetic acid and the pharmaceutically acceptable non-toxic salts and esters thereof.

33. The compound of claim 30 wherein $R_1$ is OH; $R_2$ is H; and $R_4$ is a 6 carbon cyclic alkyl, namely N-[2-endo-hydroxy-3-exo-(3-hydroxy-3-cyclohexylprop1-trans-enyl)bicyclo[3.2.0]hept-6-ylidene]aminooxyacetic acid or its optical isomers and the pharmaceutically acceptable non-toxic salts and esters thereof.

34. The compound or its optical isomers of claim 21 and the pharmaceutically acceptable non-toxic salts and esters thereof, wherein A is trans —CH=CH—.

35. The compound or its optical isomers of claim 34 wherein $R_1$ is OH; $R_2$ is H; and $R_4$ is a 5 carbon linear alkyl, namely N-[2-endo-hydroxy-3-exo-(3-hydroxyoct-1-trans-enyl)bicyclo[3.2.0]hept-6-ylidene]-3-aminooxypropionic acid; N-[2-endo-hydroxy-3-exo-(3αS-hydroxyoct-1-trans-enyl)bicyclo[3.2.0]hept-6-ylidene]-3-aminooxypropionic acid and the pharmaceutically acceptable non-toxic salts and esters thereof.

36. The compound or its optical isomers of claim 34 wherein $R_1$ is OH; $R_2$ is H; and $R_4$ is a 5 carbon cyclic alkyl, namely N-[2-endo-hydroxy-3-exo-(3-hydroxy-3-cyclopentylprop-1-trans-enyl)bicyclo[3.2.0]hept-6-ylidene]-3-aminooxypropionic acid; N-[2-endo-hydroxy-3-exo-(3-hydroxy-3-cyclopentylprop-1-trans-enyl)bicyclo[3.2.0]hept-6-ylidene]-3-aminooxypropionic acid and the pharmaceutically acceptable non-toxic salts and esters thereof.

37. The compound or its optical isomers of claim 34 wherein $R_1$ is OH; $R_2$ is H; and $R_4$ is a 6 carbon cyclic alkyl, namely N-[2-endo-hydroxy-3-exo-(3-hydroxy-3-cyclohexylprop-1-trans-enyl)bicyclo[3.2.0]hept-6-ylidene]-3-aminooxypropionic acid; N-[2-endo-hydroxy-3-exo-(3α-hydroxy-3-cyclohexylprop-1-trans-enyl)bicyclo[3.2.0]hept-6-ylidene]-3-aminooxypropionic acid and the pharmaceutically acceptable non-toxic salts and esters thereof.

38. The compound or its optical isomers of claim 15 and the pharmaceutically acceptable non-toxic salts and esters thereof, wherein A is trans —CH$_2$—CH$_2$—.

39. The compound or its optical isomers of claim 38 wherein $R_1$ is OH; $R_2$ is H; and $R_4$ is a 5 carbon linear alkyl, namely N-[2-endo-hydroxy-3-exo-(3-hydroxyoct-1-yl)bicyclo[3.2.0]hept-6-ylidene]aminooxyacetic acid; N-[2-endo-hydroxy-3-exo-(3α$\beta$8S-hydroxyoct-1-yl)bicyclo[3.2.0]hept-6-ylidene]aminooxyacetic acid and the pharmaceutically acceptable non-toxic salts and esters thereof.

40. The compound of claim 38 wherein $R_1$ is OH; $R_2$ is H; and $R_4$ is a 5 carbon cyclic alkyl, namely N-[2-endo-hydroxy-3-exo-(3-hydroxy-3-cyclopentylprop-1-yl)bicyclo[3.2.0]hept-6-ylidene]aminooxyacetic acid or its optical isomers and the pharmaceutically acceptable non-toxic salts and esters thereof.

41. The compound of claim 38 wherein $R_1$ is OH; $R_2$ is H; and $R_4$ is a 6 carbon cyclic alkyl, namely N-[2-endo-hydroxy-3-exo-(3-hydroxy-3-cyclohexylprop-1-yl)bicyclo[3.2.0]hept-6-ylidene]aminooxyacetic acid or its optical isomers and the pharmaceutically acceptable non-toxic salts and esters thereof.

42. The compound of claim 38 wherein $R_1$ is OH; $R_2$ is H; and $R_4$ is a 7 carbon linear alkyl, namely N-[2-endo-hydroxy-3-exo-(3-hydroxydec-1-yl)bicyclo[3.2.0]hept-6-ylidene]aminooxyacetic acid or its optical isomers and the pharmaceutically acceptable non-toxic salts and esters thereof.

43. The compound or its optical isomers of claim 21 and the pharmaceutically acceptable non-toxic salts and esters thereof, wherein A is trans —CH$_2$—CH$_2$—.

44. The compound or its optical isomers of claim 43 wherein $R_1$ is OH; $R_2$ is H; and $R_4$ is a 5 carbon linear alkyl, namely N-[2-endo-hydroxy-3-exo-(3-hydroxyoct-1-yl)bicyclo[3.2.0]hept-6-ylidene]-3-aminooxypropionic acid; N-[2-endo-hydroxy-3-exo-(3α$\beta$S-hydroxyoct-1-trans-enyl)bicyclo[3.2.0]hept-6-ylidene]-3-aminooxypropionic acid and the pharmaceutically acceptable non-toxic salts and esters thereof.

45. The compound of claim 43 wherein $R_1$ is OH; $R_2$ is H; and $R_4$ is a 5 carbon cyclic alkyl, namely N-[2-endo-hydroxy-3-exo-(3-hydroxy-3-cyclopentylprop-1-yl)bicyclo[3.2.0]hept-6-ylidene]-3-aminooxyacetic acid or its optical isomers and the pharmaceutically acceptable non-toxic salts and esters thereof.

46. The compound of claim 43 wherein $R_1$ is OH; $R_2$ is H; and $R_4$ is a 6 carbon cyclic alkyl, namely N-[2-endo-hydroxy-3-exo-(3-hydroxy-3-cyclohexylprop-1-yl)bicyclo[3.2.0]hept-6-ylidene]-3-aminooxypropionic acid or its optical isomers and the pharmaceutically acceptable non-toxic salts and esters thereof.

47. The compound of claim 43 wherein $R_1$ is OH; $R_2$ is H; and $R_4$ is a 7 carbon linear alkyl, namely N-[2-endo-hydroxy-3-exo-(3-hydroxydec-1-yl)bicyclo[3.2.0]hept-6-ylidene]-3-aminooxypropionic acid or its optical isomers and the pharmaceutically acceptable non-toxic salts and esters thereof.

48. A pharmaceutical composition for preventing or treating cardiovascular disorders in mammals which comprises an effective dosage of a compound of claim 1 or a pharmaceutically acceptable non-toxic salt and ester thereof in admixture with at least one pharmaceutically acceptable excipient.

49. A method for preventing or treating cardiovascular disorders in mammals which method comprises administering to a subject in need of such treatment a therapeutically effective amount of a compound of claim 1 or a pharmaceutically acceptable non-toxic salt and ester thereof.

* * * * *